US007449543B2

(12) United States Patent
Bihain et al.

(10) Patent No.: US 7,449,543 B2
(45) Date of Patent: Nov. 11, 2008

(54) SCHIZOPHRENIA RELATED PROTEIN

(75) Inventors: Bernard Bihain, Cancale (FR); Barbara Bour, San Diego, CA (US); Lydie Bougueleret, Petit-Lancy (CH)

(73) Assignee: Serono Genetics Institute S.A., Evry (FR)

( * ) Notice: Subject to any disclaimer, the term of this patent is extended or adjusted under 35 U.S.C. 154(b) by 0 days.

(21) Appl. No.: 11/693,802

(22) Filed: Mar. 30, 2007

(65) Prior Publication Data

US 2008/0199883 A1      Aug. 21, 2008

Related U.S. Application Data

(60) Division of application No. 10/071,645, filed on Feb. 6, 2002, now Pat. No. 7,220,581, which is a continuation-in-part of application No. PCT/IB01/01891, filed on Jul. 26, 2001.

(60) Provisional application No. 60/223,482, filed on Aug. 7, 2000.

(51) Int. Cl.
*C07K 14/00* (2006.01)
*C07K 14/435* (2006.01)
*C12P 21/00* (2006.01)
*C07H 21/04* (2006.01)
*A61K 38/06* (2006.01)

(52) U.S. Cl. .......................... 530/300; 514/2; 536/23.5; 435/69.1

(58) Field of Classification Search ...................... None
See application file for complete search history.

(56) References Cited

U.S. PATENT DOCUMENTS 6,222,027 B1    4/2001 Kaser et al.
2004/0086973 A1  5/2004 Duecker

FOREIGN PATENT DOCUMENTS

WO    WO 02/16415 A2    2/2002

OTHER PUBLICATIONS

Celano, E. et al. "Selective Regulation of Presynaptic Calcium/Calmodulin-Dependent Protein Kinase II by Psychotropic Drugs", *Biol Psychiatry*, Mar. 1, 2003, pp. 442-449, vol. 53, No. 5.
Du, J. et al. "Focus on CaMKII: A Molecular Switch in the Pathophysiology and Treatment of Mood and Anxiety Disorders", *Int J Neuropsychopharmacology*, Sep. 2004, pp. 243-248, vol. 7, No. 3.
Consogno, E. et al. "Modifications in Brain CaM Kinase II After Long-term Treatment with Desmethylimipramine", *Neuropsychopharmacology*, Jan. 2001, pp. 21-30, vol. 24, No. 1.
Consogno, E. et al. "Long-term Treatment with S-Adenosylmethionine Induces Changes in Presynaptic CaM Kinase II and Synapsin I", *Biol Psychiatry*, Sep. 1, 2001, pp. 337-344, vol. 50, No. 5.
Xing, G. et al. "Decreased Prefrontal CaMKII α mRNA in Bipolar Illness", *NeuroReport*, Mar. 25, 2002, pp. 501-505, vol. 13, No. 4.
Post, R. M. et al. "Neurobiology of Bipolar Illness: Implications for Future Study and Therapeutics", *Ann Clin Psychiatry*, Jun. 2003, pp. 85-94, vol. 15, No. 2.
Chumakov, I. et al. "Genetic and Physiological Data Implicating the New Human Gene G72 and the Gene for D-Amino Acid Oxidase in Schizophrenia", *Proc Natl Acad Sci USA*, Oct. 15, 2002, pp. 13675-13680, vol. 99, No. 21.
Williams, M. "Genome-Based Drug Discovery: Prioritizing Disease-Susceptibility/Disease-Associated Genes as Novel Drug Targets for Schizophrenia", *Curr Opin Investig Drugs*, Jan. 2003, pp. 31-36, vol. 4, No. 1.
Hemmingsen, R. et al. "Cortical Brain Dysfunction in Early Schizophrenia: Secondary Pathogenetic Hierarchy of Neuroplasticity, Psychopathology and Social Impairment", *Acta Psychiatr Scand Suppl.*, 1999, pp. 80-88, vol. 395, Abstract only.
Lieberman, J. A. et al. "Neurochemical Sensitization in the Pathophysiology of Schizophrenia: Deficits and Dysfunction in Neuronal Regulation and Plasticity", *Neuropsychopharmacology*, Oct. 1997, pp. 205-229, vol. 17, No. 4.
Colbran, R. J. "Targeting of Calcium/Calmodulin-Dependent Protein Kinase II", *Biochem J.*, Feb. 15, 2004, pp. 1-16, vol. 378.
Hudmon, A. et al. "Structure-Function of the Multifunctional $Ca^{2+}$/Calmodulin-Dependent Protein Kinase II", *Biochem J.*, Jun. 15, 2002, pp. 593-611, vol. 364.
Molnar, M. et al. "mRNA Expression Patterns and Distribution of White Matter Neurons in Dorsolateral Prefrontal Cortex of Depressed Patients Differ from those in Schizophrenia Patients", *Biol Psychiatry*, Jan. 1, 2003, pp. 39-47, vol. 53, No. 1.
Wang, H. et al. "Inducible Protein Knockout Reveals Temporal Requirement of CaMKII Reactivation for Memory Consolidation in the Brain", *Proc Natl Acad Sci USA*, Apr. 1, 2003, pp. 4287-4292, vol. 100, No. 7.
Zhang, J. et al. "Molecular Cloning and Characterization of a Novel Calcium/Calmodulin-Dependent Protein Kinase II Inhibitor from Human Dendritic Cells", *Biochem Biophys Res Commun*, Jul. 13, 2001, pp. 229-234, vol. 285, No. 2.
Schumacher, J. et al. "Examination of G72 and D-Amino-Acid Oxidase as Genetic Risk Factors for Schizophrenia and Bipolar Affective Disorder", *Mol Psychiatry*, Feb. 2004, pp. 203-207, vol. 9, No. 2.
Wells, J. A. "Additivity of Mutational Effects in Proteins", *Biochemistry*, Sep. 18, 1990, pp. 8509-8517, vol. 29, No. 37.

(Continued)

*Primary Examiner*—Christine J. Saoud
*Assistant Examiner*—Jon M Lockard
(74) *Attorney, Agent, or Firm*—Saliwanchik, Lloyd & Saliwanchik

(57) ABSTRACT

The invention relates to polynucleotides of the PAPAP gene, polypeptides encoded by the PAPAP gene, and antibodies directed specifically against such polypeptides. The invention also concerns methods for the treatment or diagnosis of schizophrenia, bipolar disorder or related CNS disorder. The invention also concerns the interaction of PAPAP with schizophrenia candidate gene g34872.

16 Claims, No Drawings

OTHER PUBLICATIONS

Ngo, J. T. et al. "Computational Complexity, Protein Structure Prediction, and the Levinthal Paradox", In: *The Protein Folding Problem and Tertiary Structure Prediction*, Merz and Le Gran (Eds.), Birkhauser: Boston, 1994, pp. 433-506.

Cochran, S. M. et al. "Acute and Delayed Effects of Phencyclidine Upon mRNA Levels of Markers of Glutamatergic and GABAergic Neurotransmitter Function in the Rat Brain", *Synapse*, 2002, pp. 206-214, vol. 46.

Lisman, J. et al. "The Molecular Basis of CaMKII Function in Synaptic and Behavioural Memory", *Neuroscience*, Mar. 2002, pp. 175-190, vol. 3.

Hudmon, A. et al. "Neuronal $Ca^{2+}$/Calmodulin-Dependent Protein Kinase II: The Role of Structure and Autoregulation in Cellular Function", *Annu. Rev. Biochem.*, 2002, pp. 473-510, vol. 71.

Chang, B. et al. "Characterization of a calmodulin kinase II inhibitor protein in brain" *Proceedings of the National Academy of Sciences of the USA*, Sep. 1, 1998, pp. 10890-10895, vol. 95, No. 18.

Chang, B. et al. "Calcium/calmodulin-dependent protein kinase II inhibitor protein: localization of isoforms in rat brain" *Neuroscience*, 2001, pp. 767-777, vol. 102, No. 4.

GenBank Accession No. AF271156, Jun. 11, 2000, p. 1.

SEQUENCE LISTING

```
<160> NUMBER OF SEQ ID NOS: 6

<210> SEQ ID NO 1
<211> LENGTH: 1104
<212> TYPE: DNA
<213> ORGANISM: Homo sapiens
<220> FEATURE:
<221> NAME/KEY: CDS
<222> LOCATION: 87..346

<400> SEQUENCE: 1
ggcacgaggc agcgccgctg accctgtccg ccgcgggcgg ggacgcgggc ggaggaggcg      60
ccgcggcgga gccccggac gcgacc atg tgg gag gtg ctg ccc tac ggc gac      113
                             Met Trp Glu Val Leu Pro Tyr Gly Asp
                              1               5 gag aag ctg agc ccc tac ggc gac ggc ggc gac gtg ggc cag atc ttc      161
Glu Lys Leu Ser Pro Tyr Gly Asp Gly Gly Asp Val Gly Gln Ile Phe
 10              15                  20                  25 tcc tgc cgc ctg cag gac acc aac aac ttc ttc ggc gcc ggg cag aac      209
Ser Cys Arg Leu Gln Asp Thr Asn Asn Phe Phe Gly Ala Gly Gln Asn
             30                  35                  40 aag cgg ccg ccc aag ctg ggc cag atc ggc cgg agc aag cgg gtt gtt      257
Lys Arg Pro Pro Lys Leu Gly Gln Ile Gly Arg Ser Lys Arg Val Val
         45                  50                  55 att gaa gat gat agg att gat gac gtg ctg aaa aat atg acc gac aag      305
Ile Glu Asp Asp Arg Ile Asp Asp Val Leu Lys Asn Met Thr Asp Lys
     60                  65                  70 gca cct ctg gtg tct aac tcc cca aag aca atg agt taa gggagagaat      354
Ala Pro Leu Val Ser Asn Ser Pro Lys Thr Met Ser  *
 75                  80                  85 aggaacggcg gtaacagtta ttggcaaaaa gcatgaaaag agaaagcact ttgaaattta      414
ttactagctt gtacccacga tgaaatcaac aacctgtatc tggtatatgc ccggagacag      474
attaggcgaa ggaggaagag agagagaaga aaggcttggg ccctctacaa ataaaataaa      534
aaaaaaaaat ttaaataat aaaatcccta tatcccatat aagaataaaa gagtctcagt       594
gcagtattgg caaaattaaa tccatttctt tttaatacgg gaatattggc attatagatc      654 tggatttga ccacttaatg aagcggcacc ccaggtgttt tgaggtgttg gcattcttcg       714
ctgatttggc tgttcccaat gtttacatta tttaatcttg caaaaatggt tctgtgcact      774
tggatgtgaa atgctgtcca gttttatttt ttttatgttg ttatccttgg atgtacaaaa     834
aattcagaaa atgatctctg tagatattct gttttatttt ggtcatcttt agaagttatc      894
```

| aggaatgtgt ttaaaacaag aagagaactt ttctaaggaa tgatacatag aaaagatttt | 954 |
| attttaaaat gagttgtaaa gcttgtgttt ctttgttgct gcaagctatc tgcccaagtt | 1014 |
| aatgcaaatg dacacatttt ttatgtcaga aaaacacaca cacacacaca cacacacaca | 1074 |
| cacacacacg aaaaaaaaaa aaaaaaaaaa | 1104 |

<210> SEQ ID NO 2
<211> LENGTH: 85
<212> TYPE: PRT
<213> ORGANISM: Homo sapiens

<400> SEQUENCE: 2

```
Met Trp Glu Val Leu Pro Tyr Gly Asp Glu Lys Leu Ser Pro Tyr Gly
1               5                   10                  15

Asp Gly Gly Asp Val Gly Gln Ile Phe Ser Cys Arg Leu Gln Asp Thr
            20                  25                  30

Asn Asn Phe Phe Gly Ala Gly Gln Asn Lys Arg Pro Pro Lys Leu Gly
        35                  40                  45

Gln Ile Gly Arg Ser Lys Arg Val Val Ile Glu Asp Asp Arg Ile Asp
    50                  55                  60

Asp Val Leu Lys Asn Met Thr Asp Lys Ala Pro Leu Val Ser Asn Ser
65                  70                  75                  80

Pro Lys Thr Met Ser
                85
```

<210> SEQ ID NO 3
<211> LENGTH: 3189
<212> TYPE: DNA
<213> ORGANISM: Homo sapiens

<400> SEQUENCE: 3

| ccctcccctc ccctccgcc cctcgcagcc ccgccgctcg cagctcccag tctgcctccc | 60 |
| cgaaccggcg ccgccgcccg cactcgccgc aggaccggcc cgcccggctc cggggtgcg | 120 |
| ccctcctcgg tccgcgccc tccggctcg cagggacgtc tcctccctcc cggctcgcgg | 180 |
| cccgcccgg ccggccccc gcccagagcc ccagcgcgcc gaggatgtga gtcctgctcg | 240 |
| cctctggcg agcagcagcc actcgcgcgc ggagccggag cgcagcgcag cgcagccgcg | 300 |
| ggcgctctcc gggccgctcg cgcgagtgcc gcgctcttgc cctagcggcg tccccggcc | 360 |
| tctcgccggc gccaccgccg cagcagcccg cgggccgtcc ccggccggcc gccccggcc | 420 |
| ccagcgccgc tgaccctgtc cgccgcgggc ggggacgcgg tcggaggagg cgccgcggcg | 480 |
| gagcccccgg acgcgaccat gtcggaggtg ctgccctacg cgacgagaa gctgagcccc | 540 |
| tacggcgacg gcggcgacgt gggccagatc ttctcctgcc gcctgcagga caccaacaac | 600 |
| ttcttcggcg ccgggcagaa caagcggccc cccaagctgg gccagatcgg ccggagcaag | 660 |
| cggggtgagt tcgcggcccc cttgtctgac acccccttt tcccgcgccg cggcctgaac | 720 |
| aagggttgcg gaggtctccc acccgctgga gcccgttcag acctgacgga tcccttctt | 780 |
| gcagaattgg gggatcccgc actgcgggtc cggctgaagc gggtcgcagg aacgcgtccc | 840 |
| cctaagccgg atccccggct gggtcaccct gggggcgtgg cggcttctag cagcagctgg | 900 |
| gggtctccac ccgcgcggca aagtttgctt tttgatttgc gccccccacc cccgccttt | 960 |
| gcgcagtgta gtcacagctg cactcgctcc ataaccctgt ggggagggg gcccaaggac | 1020 |
| ccccagggga cggcgtgggg acctgcgtgg ggaggatccc attcctgcgg ggaaggctag | 1080 |

-continued

```
ggtgttcggg tcgcacgggc ttttcattgt tacttggctt gggagggggt ttgccaggcc    1140
tgggcgatcc gcgcgagagc tggaaaagcc ccagagaggc ggagacgcag agaggctccg    1200
agaggagctc cagagacgcg gggacaatga gggggaccga cggctgcaga gagagactga    1260
gacgcaggga tggaggggag ggggtacgct ggagaccgag ggtggcagag accgagacaa    1320
agctcccgag aggggagctg aagcgggaga gacagagccg aggacgcgcg tttggggagg    1380
acgcagaagc cgccgaaaca ataagggcga ccgacacctt agacagggag agacagagac    1440
ctcgatcggc tgccggccgt cgcgccgagg gacgatggag ggactgagaa aggcgaggct    1500
aagtcgagac ggtaagagag gccgaggtta cggcatgtgt ccctggcagg cagcgaaggg    1560
aggctctgac ctctgcggca gcggggagcg cggggcggcc gagtcagtcg ccagcggct    1620 gggagagggc gcgcaggagg gggcgcccgc ccaggccagg ccctaacccc cacccgctgc    1680
gcgtcgtggg aaccggtttt ggcgtcccct cctggttccg ctcatctccg cacctagcct    1740
tgcccaccgg agctgcgctc gggacttacc tggggtcccg agacccaaag actttggctc    1800
cctctcctat cccagctcca gacatttctg tctaaattag tgcgcctggt gcggggagga    1860
cgcgggccag tgcgcgccct ggctgcagca ggagcggctg ggttggcgcc ctctgtttcc    1920
ttttctcaga atggagctgg gacgcaggct ggaggataga gggtggtggg tggttcagag    1980
gaaagcaggg aagggacccc tgcagggac ggaggatgga gctgtttcac cgcgcagtga    2040
gccctgctcc ctcgccctct cctctcccga cctcccactc tgggcataac gggaaatgtc    2100
agagacctct ggctaggccc cagcgcgctc acctctcttt tcccccttt ttttgcagtt    2160 gttattgaag atgataggat tgatgacgtg ctgaaaaata tgaccgacaa ggcacctcct    2220
ggtgtctaac tcccccaaag acaatgagtt aagggagaga ataagaacgg cggtaacagt    2280
tattggcaaa aagcatgaaa agagaaagca ctttgaaatt tattactagc ttgctaccca    2340
cgatgaaatc aacaacctgt atctggtatc aggccgggag acagatgagg cgagaggagg    2400
aggaggagga ggagaaggct ctgggctcct ctgcaaaaat aaaaataaaa aaataaataa    2460
aattttaaaa ataataaaaa ttcactatat acacatataa agaaataaaa agaagtctca    2520
gttgcagcta tttgtcaaaa ttaatatcca tttcttttta tatacggtga atattgcgca    2580
attatagatc tggattttga accacttaat gaagcggcaa caccaggtgt tttgaggtgt    2640
tggcattctt cgctgatttg ctgttcccca atgtttacat tatttaatct tgcaaaaatg    2700
gttctgtgca cttggatgtg aaatgctgtc cagtttcatt ttttttatgt tgttatcctt    2760
ggatgtacaa aaaattcaga aaatgatctc tgtagatatt ctgttttatt ttggtcatct    2820
ttagaagtta tcaggaatgt gtttaaaaca agaagagaac ttttctaagg aatgatacat    2880
agaaaagatt ttatttaaa atgagttgta aagcttgtgt ttctttgttg ctgcaagcta    2940
tctgcccaag ttaatgcaaa tggacacatt ttttatgtca gaaaaacaca cacacacaca    3000
cacacacaca cacacacaca cgaaaaacaa agaaaaaaat gcttgagctt tttctaactt    3060
ccccttgcag tctgttgtgt gagcagcctg tttatttctc taatattatg tcagtttatt    3120
ctctttaatg gactgtaaaa aaatgtaatc acaagagtgc caaattcttg aaatgccaaa    3180
aggctttta                                                            3189
```

```
<210> SEQ ID NO 4
<211> LENGTH: 1779
<212> TYPE: DNA
<213> ORGANISM: Homo sapiens

<400> SEQUENCE: 4
```

```
atggagacag acacactcct gctatgggta ctgctgctct gggttccagg ttccactggt    60
gacgcggccc agccggccag gcgcgcgcgc cgtacgtacg aagcttacca gcctctagaa   120
cgaatgtgga cctgcaacta caaccagcaa aaagaccagt catgcaacca caaggaaata   180
acttctacca aagctgaaag aagatcttcc ggaatcatcc cagttgagga ggagaacccg   240
gacttctgga accgcgaggc agccgaggcc ctgggtgccg ccaagaagct gcagcctgca   300
cagacagccg ccaagaacct catcatcttc ctgggcgatg ggatgggggt gtctacggtg   360
acagctgcca ggatcctaaa agggcagaag aaggacaaac tggggcctga tacccctg    420
gccatggacc gcttcccata tgtggctctg tccaagacat acaatgtaga caaacatgtg   480
ccagacagtg gagccacagc cacggcctac ctgtgcgggg tcaagggcaa cttccagacc   540
attggcttga gtgcagccgc ccgctttaac cagtgcaaca cgacacgcgg caacgaggtc   600
atctccgtga tgaatcgggc caagaaagca gggaagtcag tgggagtggt aaccaccaca   660
cgagtgcagc acgcctcgcc agccggcacc tacgcccaca cggtgaaccg caactggtac   720
tcggacgccg acgtgcctgc ctcggcccgc caggaggggt gccaggacat cgctacgcag   780
ctcatctcca acatggacat tgacgtgatc ctaggtggag gccgaaagta catgtttccc   840
atgggaaccc cagaccctga gtacccagat gactacagcc aaggtgggac caggctggac   900
gggaagaatc tggtgcagga atggctggcg aagcgccagg gtgcccggta tgtgtggaac   960
cgcactgagc tcatgcaggc ttccctggac ccgtctgtga cccatctcat gggtctcttt  1020
gagcctggag acatgaaata cgagatccac cgagactcca cactggaccc ctccctgatg  1080
gagatgacag aggctgccct gcgcctgctg agcaggaacc cccgcggctt cttcctcttc  1140
gtggagggtg gtcgcatcga ccatggtcat catgaaagca gggcttaccg ggcactgact  1200
gagacgatca tgttcgacga cgccattgag agggcgggcc agctcaccag cgaggaggac  1260
acgctgagcc tcgtcactgc cgaccactcc cacgtcttct ccttcggagg ctaccccctg  1320
cgagggagct ccatcttcgg gctggcccct ggcaaggccc gggacaggaa ggcctacacg  1380
gtcctcctat acgaaacggt ccaggctat gtgctcaagg acggcgcccg gccggatgtt  1440
accgagagcg agagcgggag ccccgagtat cggcagcagt cagcagtgcc cctggacgaa  1500
gagacccacg caggcgagga cgtggcggtg ttcgcgcgcg gcccgcaggc gcacctggtt  1560
cacggcgtgc aggagcagac cttcatagcg cacgtcatgg ccttcgccgc tgcctggag  1620
ccctacaccg cctgcgacct ggcgcccccc gccggcacca ccgacgccgc gcacccgggt  1680
tatctcgagg aagcgctctc tctagaaggg cccgaacaaa aactcatctc agaagaggat  1740
ctgaatagcg ccgtcgacca tcatcatcat catcattga                         1779
```

<210> SEQ ID NO 5
<211> LENGTH: 90
<212> TYPE: DNA
<213> ORGANISM: Homo sapiens

<400> SEQUENCE: 5

```
cag cct cta gaa cga atg tgg acc tgc aac tac aac cag caa aaa gac    48
Gln Pro Leu Glu Arg Met Trp Thr Cys Asn Tyr Asn Gln Gln Lys Asp
1               5                   10                  15 cag tca tgc aac cac aag gaa ata act tct acc aaa gct gaa             90
Gln Ser Cys Asn His Lys Glu Ile Thr Ser Thr Lys Ala Glu
            20                  25                  30
```

<210> SEQ ID NO 6

<211> LENGTH: 592
<212> TYPE: PRT
<213> ORGANISM: Homo sapiens

<400> SEQUENCE: 6

| Met | Glu | Thr | Asp | Thr | Leu | Leu | Leu | Trp | Val | Leu | Leu | Trp | Val | Pro |
|---|---|---|---|---|---|---|---|---|---|---|---|---|---|---|
| 1 | | | | 5 | | | | | 10 | | | | | 15 |

| Gly | Ser | Thr | Gly | Asp | Ala | Ala | Gln | Pro | Ala | Arg | Arg | Ala | Arg | Arg | Thr |
|---|---|---|---|---|---|---|---|---|---|---|---|---|---|---|---|
| | | | 20 | | | | | 25 | | | | | 30 | | |

| Tyr | Glu | Ala | Tyr | Gln | Pro | Leu | Glu | Arg | Met | Trp | Thr | Cys | Asn | Tyr | Asn |
|---|---|---|---|---|---|---|---|---|---|---|---|---|---|---|---|
| | | 35 | | | | | 40 | | | | | 45 | | | |

| Gln | Gln | Lys | Asp | Gln | Ser | Cys | Asn | His | Lys | Glu | Ile | Thr | Ser | Thr | Lys |
|---|---|---|---|---|---|---|---|---|---|---|---|---|---|---|---|
| | 50 | | | | | 55 | | | | | 60 | | | | |

| Ala | Glu | Arg | Arg | Ser | Ser | Gly | Ile | Ile | Pro | Val | Glu | Glu | Asn | Pro |
|---|---|---|---|---|---|---|---|---|---|---|---|---|---|---|
| 65 | | | | | 70 | | | | | 75 | | | | 80 |

| Asp | Phe | Trp | Asn | Arg | Glu | Ala | Ala | Glu | Ala | Leu | Gly | Ala | Ala | Lys | Lys |
|---|---|---|---|---|---|---|---|---|---|---|---|---|---|---|---|
| | | | | 85 | | | | | 90 | | | | | 95 | |

| Leu | Gln | Pro | Ala | Gln | Thr | Ala | Ala | Lys | Asn | Leu | Ile | Ile | Phe | Leu | Gly |
|---|---|---|---|---|---|---|---|---|---|---|---|---|---|---|---|
| | | | 100 | | | | | 105 | | | | | 110 | | |

| Asp | Gly | Met | Gly | Val | Ser | Thr | Val | Thr | Ala | Ala | Arg | Ile | Leu | Lys | Gly |
|---|---|---|---|---|---|---|---|---|---|---|---|---|---|---|---|
| | | | 115 | | | | | 120 | | | | | 125 | | |

| Gln | Lys | Lys | Asp | Lys | Leu | Gly | Pro | Glu | Ile | Pro | Leu | Ala | Met | Asp | Arg |
|---|---|---|---|---|---|---|---|---|---|---|---|---|---|---|---|
| | 130 | | | | | 135 | | | | | 140 | | | | |

| Phe | Pro | Tyr | Val | Ala | Leu | Ser | Lys | Thr | Tyr | Asn | Val | Asp | Lys | His | Val |
|---|---|---|---|---|---|---|---|---|---|---|---|---|---|---|---|
| 145 | | | | | 150 | | | | | 155 | | | | | 160 |

| Pro | Asp | Ser | Gly | Ala | Thr | Ala | Thr | Ala | Tyr | Leu | Cys | Gly | Val | Lys | Gly |
|---|---|---|---|---|---|---|---|---|---|---|---|---|---|---|---|
| | | | | 165 | | | | | 170 | | | | | 175 | |

| Asn | Phe | Gln | Thr | Ile | Gly | Leu | Ser | Ala | Ala | Ala | Arg | Phe | Asn | Gln | Cys |
|---|---|---|---|---|---|---|---|---|---|---|---|---|---|---|---|
| | | | 180 | | | | | 185 | | | | | 190 | | |

| Asn | Thr | Thr | Arg | Gly | Asn | Glu | Val | Ile | Ser | Val | Met | Asn | Arg | Ala | Lys |
|---|---|---|---|---|---|---|---|---|---|---|---|---|---|---|---|
| | | 195 | | | | | 200 | | | | | 205 | | | |

| Lys | Ala | Gly | Lys | Ser | Val | Gly | Val | Val | Thr | Thr | Thr | Arg | Val | Gln | His |
|---|---|---|---|---|---|---|---|---|---|---|---|---|---|---|---|
| | 210 | | | | | 215 | | | | | 220 | | | | |

| Ala | Ser | Pro | Ala | Gly | Thr | Tyr | Ala | His | Thr | Val | Asn | Arg | Asn | Trp | Tyr |
|---|---|---|---|---|---|---|---|---|---|---|---|---|---|---|---|
| 225 | | | | | 230 | | | | | 235 | | | | | 240 |

| Ser | Asp | Ala | Asp | Val | Pro | Ala | Ser | Ala | Arg | Gln | Glu | Gly | Cys | Gln | Asp |
|---|---|---|---|---|---|---|---|---|---|---|---|---|---|---|---|
| | | | | 245 | | | | | 250 | | | | | 255 | |

| Ile | Ala | Thr | Gln | Leu | Ile | Ser | Asn | Met | Asp | Ile | Asp | Val | Ile | Leu | Gly |
|---|---|---|---|---|---|---|---|---|---|---|---|---|---|---|---|
| | | | 260 | | | | | 265 | | | | | 270 | | |

| Gly | Gly | Arg | Lys | Tyr | Met | Phe | Pro | Met | Gly | Thr | Pro | Asp | Pro | Glu | Tyr |
|---|---|---|---|---|---|---|---|---|---|---|---|---|---|---|---|
| | | 275 | | | | | 280 | | | | | 285 | | | |

| Pro | Asp | Asp | Tyr | Ser | Gln | Gly | Gly | Thr | Arg | Leu | Asp | Gly | Lys | Asn | Leu |
|---|---|---|---|---|---|---|---|---|---|---|---|---|---|---|---|
| | 290 | | | | | 295 | | | | | 300 | | | | |

| Val | Gln | Glu | Trp | Leu | Ala | Lys | Arg | Gln | Gly | Ala | Arg | Tyr | Val | Trp | Asn |
|---|---|---|---|---|---|---|---|---|---|---|---|---|---|---|---|
| 305 | | | | | 310 | | | | | 315 | | | | | 320 |

| Arg | Thr | Glu | Leu | Met | Gln | Ala | Ser | Leu | Asp | Pro | Ser | Val | Thr | His | Leu |
|---|---|---|---|---|---|---|---|---|---|---|---|---|---|---|---|
| | | | | 325 | | | | | 330 | | | | | 335 | |

| Met | Gly | Leu | Phe | Glu | Pro | Gly | Asp | Met | Lys | Tyr | Glu | Ile | His | Arg | Asp |
|---|---|---|---|---|---|---|---|---|---|---|---|---|---|---|---|
| | | | 340 | | | | | 345 | | | | | 350 | | |

| Ser | Thr | Leu | Asp | Pro | Ser | Leu | Met | Glu | Met | Thr | Glu | Ala | Ala | Leu | Arg |
|---|---|---|---|---|---|---|---|---|---|---|---|---|---|---|---|
| | | 355 | | | | | 360 | | | | | 365 | | | |

| Leu | Leu | Ser | Arg | Asn | Pro | Arg | Gly | Phe | Phe | Leu | Phe | Val | Glu | Gly | Gly |
|---|---|---|---|---|---|---|---|---|---|---|---|---|---|---|---|
| | 370 | | | | | 375 | | | | | 380 | | | | |

| Arg | Ile | Asp | His | Gly | His | His | Glu | Ser | Arg | Ala | Tyr | Arg | Ala | Leu | Thr |
|---|---|---|---|---|---|---|---|---|---|---|---|---|---|---|---|

```
                                -continued
385                 390                 395                 400
Glu Thr Ile Met Phe Asp Asp Ala Ile Glu Arg Ala Gly Gln Leu Thr
                    405                 410                 415

Ser Glu Glu Asp Thr Leu Ser Leu Val Thr Ala Asp His Ser His Val
            420                 425                 430

Phe Ser Phe Gly Gly Tyr Pro Leu Arg Gly Ser Ser Ile Phe Gly Leu
        435                 440                 445

Ala Pro Gly Lys Ala Arg Asp Arg Lys Ala Tyr Thr Val Leu Leu Tyr
    450                 455                 460

Gly Asn Gly Pro Gly Tyr Val Leu Lys Asp Gly Ala Arg Pro Asp Val
465                 470                 475                 480

Thr Glu Ser Glu Ser Gly Ser Pro Glu Tyr Arg Gln Gln Ser Ala Val
                485                 490                 495

Pro Leu Asp Glu Glu Thr His Ala Gly Glu Asp Val Ala Val Phe Ala
                500                 505                 510

Arg Gly Pro Gln Ala His Leu Val His Gly Val Gln Glu Gln Thr Phe
            515                 520                 525

Ile Ala His Val Met Ala Phe Ala Ala Cys Leu Glu Pro Tyr Thr Ala
        530                 535                 540

Cys Asp Leu Ala Pro Pro Ala Gly Thr Thr Asp Ala Ala His Pro Gly
545                 550                 555                 560

Tyr Leu Glu Glu Ala Leu Ser Leu Glu Gly Pro Glu Gln Lys Leu Ile
                565                 570                 575

Ser Glu Glu Asp Leu Asn Ser Ala Val Asp His His His His His His
                580                 585                 590
```

SCHIZOPHRENIA RELATED PROTEIN

CROSS REFERENCE TO RELATED APPLICATIONS

This application is a divisional of U.S. patent application Ser. No. 10/071,645, filed filed Feb. 6, 2002, now U.S. Pat. No. 7,220,581, which is a continuation-in-part of PCT application PCT/IB01/01891, filed Jul. 26, 2001, which claims priority to U.S. provisional application No. 60/223,482, now abandoned, filed Aug. 7, 2000, all of which are herein incorporated by reference in their entireties.

FIELD OF THE INVENTION

The present invention is directed to polynucleotides of the PAPAP gene, polypeptides encoded by the PAPAP gene, and antibodies directed specifically against such polypeptides. The invention also concerns methods for the treatment or diagnosis of schizophrenia, bipolar disorder or related CNS disorders. The invention also concerns the interaction of PAPAP with schizophrenia candidate gene g34872.

BACKGROUND OF THE INVENTION

Advances in the technological armamentarium available to basic and clinical investigators have enabled increasingly sophisticated studies of brain and nervous system function in health and disease. Numerous hypotheses both neurobiological and pharmacological have been advanced with respect to the neurochemical and genetic mechanisms involved in central nervous system (CNS) disorders, including psychiatric disorders and neurodegenerative diseases. However, CNS disorders have complex and poorly understood etiologies, as well as symptoms that are overlapping, poorly characterized, and difficult to measure. As a result future treatment regimes and drug development efforts will be required to be more sophisticated and focused on multigenic causes, and will need new assays to segment disease populations, and provide more accurate diagnostic and prognostic infon-nation on patients suffering from CNS disorders.

CNS disorders can encompass a wide range of disorders, and a correspondingly wide range of genetic factors. Examples of CNS disorders include neurodegenerative disorders, psychotic disorders, mood disorders, autism, substance dependence and alcoholism, mental retardation, and other psychiatric diseases including cognitive, anxiety, eating, impulse-control, and personality disorders. Disorders can be defined using the Diagnosis and Statistical Manual of Mental Disorders fourth edition (DSM-IV) classification.

Even when considering just a small subset of CNS disorders, it is evident from the lack of adequate treatment for and understanding of the molecular basis of the psychotic disorders schizophrenia and bipolar disorder that new targets for therapeutic invention and improved methods of treatment are needed. For both schizophrenia and bipolar disorder, all the known molecules used for the treatment of schizophrenia have side effects and act only against the symptoms of the disease. There is a strong need for new molecules without associated side effects and directed against targets which are involved in the causal mechanisms of schizophrenia and bipolar disorder. Therefore, tools facilitating the discovery and characterization of these targets are necessary and useful.

The aggregation of schizophrenia and bipolar disorder in families, the evidence from twin and adoption studies, and the lack of variation in incidence worldwide, indicate that schizophrenia and bipolar disorder are primarily genetic conditions, although environmental risk factors are also involved at some level as necessary, sufficient, or interactive causes. For example, schizophrenia occurs in 1% of the general population. But, if there is one grandparent with schizophrenia, the risk of getting the illness increases to about 3%; one parent with Schizophrenia, to about 10%. When both parents have schizophrenia, the risk rises to approximately 40%.

Identification of Schizophrenia Susceptibility Gene on Chromosome 13q31-q33

The identification of genes involved in a particular trait such as a specific central nervous system disorder, like schizophrenia, can be carried out through two main strategies currently used for genetic mapping: linkage analysis and association studies. Linkage analysis requires the study of families with multiple affected individuals and is now useful in the detection of mono- or oligogenic inherited traits. Conversely, association studies examine the frequency of marker alleles in unrelated trait (T+) individuals compared with trait negative (T−) controls, and are generally employed in the detection of polygenic inheritance.

Genetic link or "linkage" is based on an analysis of which of two neighboring sequences on a chromosome contains the least recombinations by crossing-over during meiosis. To do this, chromosomal markers, like microsatellite markers, have been localized with precision on the genome. Genetic link analysis calculates the probabilities of recombinations on the target gene with the chromosomal markers used, according to the genealogical tree, the transmission of the disease, and the transmission of the markers. Thus, if a particular allele of a given marker is transmitted with the disease more often than chance would have it (recombination level between 0 and 0.5), it is possible to deduce that the target gene in question is found in the neighborhood of the marker. Using this technique, it has been possible to localize several genes demonstrating a genetic predisposition of familial cancers. In order to be able to be included in a genetic link study, the families affected by a hereditary form of the disease must satisfy the "informativeness" criteria: several affected subjects (and whose constitutional DNA is available) per generation, and at best having a large number of siblings.

Results of previous linkage studies supported the hypothesis that chromosome 13 was likely to harbor a schizophrenia susceptibility locus on 13q32 (Blouin J L et al., 1998, Nature Genetics, 20:70-73; Lin M W et al., 1997, Hum. Genet., 99(3): 417-420). These observations suggesting the presence of a schizophrenia locus on the chromosome 13q32 locus had been obtained by carrying out linkage studies. Linkage analysis had been successfully applied to map simple genetic traits that show clear Mendelian inheritance patterns and which have a high penetrance, but this method suffers from a variety of drawbacks. First, linkage analysis is limited by its reliance on the choice of a genetic model suitable for each studied trait. Furthermore, the resolution attainable using linkage analysis is limited, and complementary studies are required to refine the analysis of the typical 20 Mb regions initially identified through this method. In addition, linkage analysis has proven difficult when applied to complex genetic traits, such as those due to the combined action of multiple genes and/or environmental factors. In such cases, too great an effort and cost are needed to recruit the adequate number of affected families required for applying linkage analysis to these situations. Finally, linkage analysis cannot be applied to the study of traits for which no large informative families are available.

More recently, instead of using linkage studies, a novel schizophrenia and bipolar disorder related gene referred to as the g34872 gene located on the chromosome 13q31-q33 locus was identified using an alternative method of conducting association studies. This alternative method involved generating biallelic markers (primarily single nucleotide polymorphisms) in the region of interest, identifying markers in linkage disequilibrium with schizophrenia, and conducting association studies in unrelated schizophrenia and bipolar disorder case and control populations.

In summary, a BAC contig covering the candidate genomic region was constructed using 27 public STSs localised in the chromosome 13q31-q33 region to screen a 7 genome equivalent proprietary BAC library. From these materials, new STSs were generated allowing construction of a dense physical map of the region. In total, 275 STSs allowed identification of 255 BACs that were all sized and mapped by in situ chromosomal hybridisation for verification. New biallelic markers were generated by partial sequencing of insert ends from subclones of some of the BAC inserts localized to the human chromosome 13q31-q33 region. In a first phase of the analysis, a first set of 34 biallelic markers on 9 different BACs across the chromosome 13q31-q33 candidate locus were analysed in schizophrenic cases and controls, thereby identifying a subregion showing an association with schizophrenia. Following this first analysis, further biallelic markers were generated as described above in order to provide a very high density map of the target region. A minimal set of 35 BACs was identified and fully sequenced which resulted in several contigs including a contig of over 900 kb comprising sequences of the target region.

These biallelic markers were used in association studies in order to refine a particular subregion of interest, which contained a candidate schizophrenia gene, g34872. The biallelic markers were genotyped in several studies carried out in different populations to confirm the association with the subregion. Association studies were first performed on two different screening samples of schizophrenia cases and controls from a French Canadian population comprising 139 cases and 141 controls, and 215 cases and 241 controls, respectively, as well on bipolar disorder cases and controls from an Argentinian population. The results obtained after several studies using this population indicated a genomic region of about 150 kb showing a significant association with schizophrenia. This association was then confirmed in separate studies using cases and controls from a U.S. schizophrenia population, as well as in further samples from the Argentinian and French Canadian populations.

The approximately 150 kb genomic region associated with schizophrenia was found to contain the candidate gene g34872. In addition to characterizing the intron-exon structure of the g34872 gene, a range of mRNA splicing variants including tissue specific mRNA splicing variants were identified, and the existence of the mRNA was demonstrated. Subsequently, a peptide fragment derived from the g34872 polypeptide product, the amino acid sequence of which is shown in SEQ ID NO: 5, caused a decrease in locomotor movement frequency, and an increase in stereotypy when injected intraperitoneally in mice. Further discussion of the identification of the g34872 gene is provided in copending U.S. patent application Ser. No. 09/539,333 titled "Schizophrenia associated genes, proteins and biallelic markers" and copending International Patent Application No. PCT/IB00/00435, both filed 30 Mar. 2000 and incorporated herein by reference in their entireties.

Calcium/calmodulin-dependent kinase II (CaM-KII) is a widely distributed protein kinase that is particularly abundant in neuronal tissues. This kinase phosphorylates a large number of substrates, including transcription factors, ion channels, enzymes, and other proteins. In the nervous system, CaM-KII plays a role in glutaminergic receptor activity and also influences neuronal activities including synaptic plasticity, long-term potentiation, learning, memory, and other aspects of behavior. Animals deficient for this kinase exhibit various behavioral abnormalities, including a decreased fear response and an increase in defensive aggression, and also show decreased serotonin release (Chen et al. (1994) Science 266:291-294). Overexpression of CaM-KII in transgenic mice leads to defects in learning and memory, and displayed defects in long-term potentiation (Rotenberg et al. (1996) Cell 87:1351-1361; Cho et al. (1998) Science 279:867-869). CaM-KII has been localized within the nervous system to post-synaptic glutaminergic synapses (Liu and Jones (1996) PNAS 93:7332-7336).

CaM-KII is also involved in a number of cellular processes beyond those controlling neuronal function, in particular those involving the cell cycle. For example, CaM-KII is required for the initiation of centrosome duplication in *Xenopus* egg extracts (Matsumoro and Maller (2002) Science 295:499-502). In addition, cell-cycle dependent changes in organelle transport have been shown to be mediated by CaM-kII phosphorylation of Myosin-V (Karcher et al. (2001) Science 293:1317-1320).

There is a strong need to identify genes involved in schizophrenia and bipolar disorder. There is also a need to identify genes involved in the g34872 pathway and genes whose products functionally interact with the g34872 gene products. These genes may provide new intervention points in the treatment of schizophrenia or bipolar disorder and allow further study and characterization of the g34872 gene and related biological pathway. The knowledge of these genes and the related biological pathways involved in schizophrenia will allow researchers to understand the etiology of schizophrenia and bipolar disorder and will lead to drugs and medications which are directed against the cause of the diseases. There is also a great need for new methods for detecting a susceptibility to schizophrenia and bipolar disorder, as well as for preventing or following up the development of the disease. Diagnostic tools could also prove extremely useful. Indeed, early identification of subjects at risk of developing schizophrenia would enable early and/or prophylactic treatment to be administered. Moreover, accurate assessments of the eventual efficacy of a medicament as well as the patent's eventual tolerance to it may enable clinicians to enhance the benefit/risk ratio of schizophrenia and bipolar disorder treatment regimes.

The present invention thus relates to a novel gene and protein which interacts with a g34872 peptide. The inventors have cloned said novel gene, referred to as the PAPAP gene, and demonstrate that the PAPAP gene product interacts with the g34872 peptide. Knowledge of a g34872 binding partner permits the development of medicaments for the treatment of CNS disease mediated by g34872 and/or PAPAP, and allows the study of g34872 by providing means for the detection of PAPAP, g34872 and g34872-PAPAP complexes or interactions.

SUMMARY OF THE INVENTION

The present invention pertains to nucleic acid molecules comprising the genomic sequence of a novel human gene which encodes a PAPAP protein. The PAPAP genomic sequence comprises regulatory sequence located upstream (5'-end) and downstream (3'-end) of the transcribed portion of said gene, these regulatory sequences being also part of the invention.

The invention also deals with the complete cDNA sequence encoding the PAPAP protein, as well as with PAPAP polypeptides and antibodies specifically recognizing the PAPAP polyepeptide. Also included is a PAPAP-g34872 complex free of protein with which it is naturally associated, as well as antibodies specifically recognizing said complex.

Oligonucleotide probes or primers hybridizing specifically with a PAPAP genomic or cDNA sequence are also part of the present invention, as well as DNA amplification and detection methods using said primers and probes.

A further object of the invention consists of recombinant vectors comprising any of the nucleic acid sequences described above, and in particular of recombinant vectors comprising a PAPAP regulatory sequence or a sequence encoding a PAPAP protein, as well as of cell hosts and transgenic non human animals comprising said nucleic acid sequences or recombinant vectors.

The invention is also directed to methods for the screening of substances or molecules that inhibit the expression of PAPAP, as well as with methods for the screening of substances or molecules that interact with a PAPAP polypeptide, that modulate the activity of a PAPAP polypeptide or that disrupt, prevent, destabilize or enhance binding and/or interactions of the PAPAP and g34872 peptides and/or proteins.

Finally, the invention is directed to use of the PAPAP polypeptide, antibodies thereto, and agonists and antagonists of PAPAP activity in the treatment of CNS and other disorders.

Brief Description of the Sequences Provided in the Sequence Listing

SEQ ID NO: 1 contains a cDNA sequence of PAPAP.

SEQ ID NO: 2 contains the amino acid sequence encoded by the cDNA of SEQ ID NO: 1.

SEQ ID NO: 3 contains a genomic DNA sequence of PAPAP.

SEQ ID NO: 4 contains a DNA sequence encoding a g34872 peptide-alkaline phosphatase fusion protein described in example 1.

SEQ ID NO: 5 contains a DNA sequence encoding a g34872 peptide used to identify and clone the PAPAP gene, as described in example 1.

SEQ ID NO: 6 contains the amino acid sequence encoded by the DNA of SEQ ID NO: 4.

DETAILED DESCRIPTION

Identification of the PAPAP Gene Located on Chromosome 1p35-p36

The inventors have used an expression cloning method to identify the PAPAP protein, as described further herein in Example 1. Briefly, the inventors created an in-frame fusion of a cDNA sequence encoding a peptide fragment of a g34872 peptide with the C-terminus of secreted alkaline phosphatase (AP) in a vector containing a secretion signal sequence located upstream of the insert which directed the fusion protein to be secreted into the media, where media containing the fusion protein can be collected, assayed for AP activity, and used in an in situ receptor/ligand assay. The inventors then conducted the in situ receptor/ligand assay. cDNAs from a human brain cDNA library were cloned into an expression vector and transfected into COS-1 cells. The secreted AP fusion protein was used as a probe to clone PAPAP by incubating the cells with g34872 peptide-AP fusion protein-containing medium. When a positive clone was detected, the assay was repeated using smaller pools of cDNAs until a single clone was identified.

The present invention thus concerns polynucleotides and polypeptides related to the PAPAP gene. Oligonucleotide probes and primers hybridizing specifically with a genomic or a cDNA sequence of PAPAP are also part of the invention. A further object of the invention consists of recombinant vectors comprising any of the nucleic acid sequences described in the present invention, and in particular recombinant vectors comprising a regulatory region of PAPAP or a sequence encoding the PAPAP protein, as well as cell hosts comprising said nucleic acid sequences or recombinant vectors. The invention also encompasses methods of screening of molecules which inhibit the expression of the PAPAP gene, which modulate the activity of the PAPAP protein, or that disrupt, prevent, destabilize or enhance binding and/or interactions of the PAPAP and g34872 peptides and/or proteins. The invention also deals with antibodies directed specifically against such polypeptides that are useful as diagnostic reagents.

The identified PAPAP gene and protein can be used in the design of assays for the diagnosis of schizophrenia or bipolar disorder, and for the design of assays for the reliable detection of genetic susceptibility to schizophrenia, bipolar disorder and related disorders. PAPAP nucleic acids and polypeptides as well as antibodies directed to said polypeptides can be used in the treatment of these and other disorders. The PAPAP gene and protein and antibodies thereto can also be used the design of drug screening protocols to provide an accurate and efficient evaluation of the therapeutic and side-effect potential of new or already existing medicament or treatment regime. Furthermore, PAPAP nucleic acids and polypeptides can be used for research in the study of g34872 and PAPAP and their involvement in CNS disease, as well as into the role of CaM-KII in neurons and other cells as well as in various human diseases.

DEFINITIONS

Before describing the invention in greater detail, the following definitions are set forth to illustrate and define the meaning and scope of the terms used to describe the invention herein.

The terms "PAPAP gene", when used herein, encompasses genomic, mRNA and cDNA sequences encoding the PAPAP protein, including the untranslated regulatory regions of the genomic DNA.

The term "heterologous protein", when used herein, is intended to designate any protein or polypeptide other than the PAPAP protein. More particularly, the heterologous protein is a compound which can be used as a marker in further experiments with a PAPAP regulatory region.

The term "isolated" requires that the material be removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that the vector or composition is not part of its natural environment.

For example, a naturally-occurring polynucleotide present in a living animal is not isolated, but the same polynucleotide, separated from some or all of the coexisting materials in the natural system, is isolated. Specifically excluded from the definition of "isolated" are: naturally-occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified polynucleotide makes up less than 5% of the number of nucleic acid inserts in the vector molecules. Further specifically excluded are whole cell genomic DNA or whole cell RNA preparations (including said whole cell preparations which are mechanically sheared or enzymaticly digested). Further specifically excluded are the above whole cell preparations as either an in vitro preparation or as a heterogeneous mixture separated by electrophoresis (including blot transfers of the same) wherein the polynucleotide of the invention has not further been separated from the heterologous polynucleotides in the electrophoresis medium (e.g., further separating by excising a single band from a heterogeneous band population in an agarose gel or nylon blot).

As used herein, the term "purified" does not require absolute purity; rather, it is intended as a relative definition. Purification of starting material or natural material is at least one order of magnitude, preferably two or three orders, and more preferably four or five orders of magnitude is expressly contemplated. As an example, purification from 0.1% concentration to 10% concentration is two orders of magnitude.

To illustrate, individual cDNA clones isolated from a cDNA library have been conventionally purified to electrophoretic homogeneity. The sequences obtained from these clones could not be obtained directly either from the library or from total human DNA. The cDNA clones are not naturally occurring as such, but rather are obtained via manipulation of a partially purified naturally occurring substance (messenger RNA). The conversion of mRNA into a cDNA library involves the creation of a synthetic substance (cDNA) and pure individual cDNA clones can be isolated from the synthetic library by clonal selection. Thus, creating a cDNA library from messenger RNA and subsequently isolating individual clones from that library results in an approximately $10^4$-$10^6$ fold purification of the native message.

The term "purified" is further used herein to describe a polypeptide or polynucleotide of the invention which has been separated from other compounds including, but not limited to, polypeptides or polynucleotides, carbohydrates, lipids, etc. The term "purified" may be used to specify the separation of monomeric polypeptides of the invention from oligomeric forms such as homo- or hetero-dimers, trimers, etc. The term "purified" may also be used to specify the separation of covalently closed polynucleotides from linear polynucleotides. A polynucleotide is substantially pure when at least about 50%, preferably 60 to 75% of a sample exhibits a single polynucleotide sequence and conformation (linear versus covalently close). A substantially pure polypeptide or polynucleotide typically comprises about 50%, preferably 60 to 90% weight/weight of a polypeptide or polynucleotide sample, respectively, more usually about 95%, and preferably is over about 99% pure. Polypeptide and polynucleotide purity, or homogeneity, is indicated by a number of means well known in the art, such as agarose or polyacrylamide gel electrophoresis of a sample, followed by visualizing a single band upon staining the gel. For certain purposes higher resolution can be provided by using HPLC or other means well known in the art. As an alternative embodiment, purification of the polypeptides and polynucleotides of the present invention may be expressed as "at least" a percent purity relative to heterologous polypeptides and polynucleotides (DNA, RNA or both). As a preferred embodiment, the polypeptides and polynucleotides of the present invention are at least; 10%, 20%, 30%, 40%, 50%, 60%, 70%, 80%, 90%, 95%, 96%, 96%, 98%, 99%, or 100% pure relative to heterologous polypeptides and polynucleotides, respectively. As a further preferred embodiment the polypeptides and polynucleotides have a purity ranging from any number, to the thousandth position, between 90% and 100% (e.g., a polypeptide or polynucleotide at least 99.995% pure) relative to either heterologous polypeptides or polynucleotides, respectively, or as a weight/weight ratio relative to all compounds and molecules other than those existing in the carrier. Each number representing a percent purity, to the thousandth position, may be claimed as individual species of purity.

The term "polypeptide" refers to a polymer of amino acids without regard to the length of the polymer; thus, peptides, oligopeptides, and proteins are included within the definition of polypeptide. This term also does not specify or exclude post-expression modifications of polypeptides, for example, polypeptides which include the covalent attachment of glycosyl groups, acetyl groups, phosphate groups, lipid groups and the like are expressly encompassed by the term polypeptide. Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring.

The term "recombinant polypeptide" is used herein to refer to polypeptides that have been artificially designed and which comprise at least two polypeptide sequences that are not found as contiguous polypeptide sequences in their initial natural environment, or to refer to polypeptides which have been expressed from a recombinant polynucleotide.

The term "purified polypeptide" is used herein to describe a polypeptide of the invention which has been separated from other compounds including, but not limited to nucleic acids, lipids, carbohydrates and other proteins. A polypeptide is substantially pure when at least about 50%, preferably 60 to 75% of a sample exhibits a single polypeptide sequence. A substantially pure polypeptide typically comprises about 50%, preferably 60 to 90% weight/weight of a protein sample, more usually about 95%, and preferably is over about 99% pure. Polypeptide purity or homogeneity is indicated by a number of means well known in the art, such as polyacrylamide gel electrophoresis of a sample, followed by visualizing a single polypeptide band upon staining the gel. For certain purposes higher resolution can be provided by using HPLC or other means well known in the art.

As used herein, the term "non-human animal" refers to any non-human vertebrate, birds and more usually mammals, preferably primates, farm animals such as swine, goats, sheep, donkeys, and horses, rabbits or rodents, more preferably rats or mice. As used herein, the term "animal" is used to refer to any vertebrate, preferable a mammal. Both the terms "animal" and "mammal" expressly embrace human subjects unless preceded with the term "non-human".

As used herein, the term "antibody" refers to a polypeptide or group of polypeptides which are comprised of at least one binding domain, where an antibody binding domain is formed from the folding of variable domains of an antibody molecule to form three-dimensional binding spaces with an internal surface shape and charge distribution complementary to the features of an antigenic determinant of an antigen, which allows an immunological reaction with the antigen. Antibodies include recombinant proteins comprising the binding domains, as wells as fragments, including Fab, Fab', F(ab)$_2$, and F(ab')$_2$ fragments.

As used herein, an "antigenic determinant" is the portion of an antigen molecule, in this case a PAPAP polypeptide, that determines the specificity of the antigen-antibody reaction. An "epitope" refers to an antigenic determinant of a polypeptide. An epitope can comprise as few as 3 amino acids in a spatial conformation which is unique to the epitope. Generally an epitope comprises at least 6 such amino acids, and more usually at least 8-10 such amino acids. Methods for determining the amino acids which make up an epitope include x-ray crystallography, 2-dimensional nuclear magnetic resonance, and epitope mapping e.g. the Pepscan method described by Geysen et al. 1984; PCT Publication No. WO 84/03564; and PCT Publication No. WO 84/03506.

Throughout the present specification, the expression "nucleotide sequence" may be employed to designate indifferently a polynucleotide or a nucleic acid. More precisely, the expression "nucleotide sequence" encompasses the nucleic material itself and is thus not restricted to the sequence information (i.e. the succession of letters chosen among the four base letters) that biochemically characterizes a specific DNA or RNA molecule.

As used interchangeably herein, the terms "nucleic acids", "oligonucleotides", and "polynucleotides" include RNA, DNA, or RNA/DNA hybrid sequences of more than one nucleotide in either single chain or duplex form. The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although the term "nucleotide" is also used herein to encompass "modified nucleotides" which comprise at least one modifications (a) an alternative linking group, (b) an analogous form of purine, (c) an analogous form of pyrimidine, or (d) an analogous sugar, for examples of analogous linking groups, purine, pyrimidines, and sugars see for example PCT publication No. WO 95/04064. The polynucleotide sequences of the invention may be prepared by any known method, including synthetic, recombinant, ex vivo generation, or a combination thereof, as well as utilizing any purification methods known in the art.

A sequence which is "operably linked" to a regulatory sequence such as a promoter means that said regulatory element is in the correct location and orientation in relation to the nucleic acid to control RNA polymerase initiation and expression of the nucleic acid of interest. As used herein, the term "operably linked" refers to a linkage of polynucleotide elements in a functional relationship. For instance, a promoter or enhancer is operably linked to a coding sequence if it affects the transcription of the coding sequence.

The terms "trait" and "phenotype" are used interchangeably herein and refer to any visible, detectable or otherwise measurable property of an organism such as symptoms of, or susceptibility to a disease for example. Typically the terms "trait" or "phenotype" are used herein to refer to symptoms of, or susceptibility to a disease, a beneficial response to or side effects related to a treatment. Preferably, said trait can be, without to be limited to, cancers, developmental diseases, and neurological diseases.

The term "allele" is used herein to refer to variants of a nucleotide sequence. A biallelic polymorphism has two forms. Diploid organisms may be homozygous or heterozygous for an allelic form.

The term "genotype" as used herein refers the identity of the alleles present in an individual or a sample. In the context of the present invention, a genotype preferably refers to the description of the biallelic marker alleles present in an individual or a sample. The term "genotyping" a sample or an individual for a biallelic marker involves determining the specific allele or the specific nucleotide carried by an individual at a biallelic marker.

The term "mutation" as used herein refers to a difference in DNA sequence between or among different genomes or individuals which has a frequency below 1%.

The term "polymorphism" as used herein refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. A single nucleotide polymorphism is the replacement of one nucleotide by another nucleotide at the polymorphic site. Deletion of a single nucleotide or insertion of a single nucleotide also gives rise to single nucleotide polymorphisms. In the context of the present invention, "single nucleotide polymorphism" preferably refers to a single nucleotide substitution. Typically, between different individuals, the polymorphic site may be occupied by two different nucleotides. The terms "biallelic polymorphism" and "biallelic marker" are used interchangeably herein to refer to a single nucleotide polymorphism having two alleles at a fairly high frequency in the population. A "biallelic marker allele" refers to the nucleotide variants present at a biallelic marker site.

The term "upstream" is used herein to refer to a location which is toward the 5' end of the polynucleotide from a specific reference point.

The terms "base paired" and "Watson & Crick base paired" are used interchangeably herein to refer to nucleotides which can be hydrogen bonded to one another be virtue of their sequence identities in a manner like that found in double-helical DNA with thymine or uracil residues linked to adenine residues by two hydrogen bonds and cytosine and guanine residues linked by three hydrogen bonds (See Stryer, L., *Biochemistry*, $4^{th}$ edition, 1995).

The terms "complementary" or "complement thereof" are used herein to refer to the sequences of polynucleotides which is capable of forming Watson & Crick base pairing with another specified polynucleotide throughout the entirety of the complementary region. For the purpose of the present invention, a first polynucleotide is deemed to be complementary to a second polynucleotide when each base in the first polynucleotide is paired with its complementary base. Complementary bases are, generally, A and T (or A and U), or C and G.

"Complement" is used herein as a synonym from "complementary polynucleotide", "complementary nucleic acid" and "complementary nucleotide sequence". These terms are applied to pairs of polynucleotides based solely upon their sequences and not any particular set of conditions under which the two polynucleotides would actually bind.

Variants and Fragments

1—Polynucleotides

The invention also relates to variants and fragments of the polynucleotides described herein, particularly of a PAPAP gene containing one or more biallelic markers according to the invention.

Variants of polynucleotides, as the term is used herein, are polynucleotides that differ from a reference polynucleotide. A variant of a polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms. Generally, differences are limited so that the nucleotide sequences of the reference and the variant are closely similar overall and, in many regions, identical.

Variants of polynucleotides according to the invention include, without being limited to, nucleotide sequences which are at least 95% identical to a polynucleotide of SEQ ID NOs: 1 or 3 or to any polynucleotide fragment of at least 12 consecutive nucleotides of a polynucleotide of SEQ ID NOs: 1 or 3, and preferably at least 99% identical, more particularly at least 99.5% identical, and most preferably at least 99.8% identical to a polynucleotide of SEQ ID NOs: 1 or 3 or to any polynucleotide fragment of at least 12 consecutive nucleotides of a polynucleotide of SEQ ID NOs: 1 or 3.

Nucleotide changes present in a variant polynucleotide may be silent, which means that they do not alter the amino acids encoded by the polynucleotide. However, nucleotide changes may also result in amino acid substitutions, additions, deletions, fusions and truncations in the polypeptide encoded by the reference sequence. The substitutions, deletions or additions may involve one or more nucleotides. The variants may be altered in coding or non-coding regions or both. Alterations in the coding regions may produce conservative or non-conservative amino acid substitutions, deletions or additions.

In the context of the present invention, particularly preferred embodiments are those in which the polynucleotides encode polypeptides which retain substantially the same biological function or activity as the mature PAPAP protein, or those in which the polynucleotides encode polypeptides which maintain or increase a particular biological activity, while reducing a second biological activity A polynucleotide fragment is a polynucleotide having a sequence that is entirely the same as part but not all of a given nucleotide sequence, preferably the nucleotide sequence of a PAPAP gene, and variants thereof. The fragment can be a portion of an intron or an exon of a PAPAP gene. It can also be a portion of the regulatory regions of PAPAP.

Such fragments may be "free-standing", i.e. not part of or fused to other polynucleotides, or they may be comprised within a single larger polynucleotide of which they form a part or region. Indeed, several of these fragments may be present within a single larger polynucleotide.

Optionally, such fragments may consist of, or consist essentially of a contiguous span of at least 8, 10, 12, 15, 18, 20, 25, 35, 40, 50, 70, 80, 100, 250, 500 or 1000 nucleotides in length.

2—Polypeptides

The invention also relates to variants, fragments, analogs and derivatives of the polypeptides described herein, including mutated PAPAP proteins.

The variant may be 1) one in which one or more of the amino acid residues are substituted with a conserved or non-conserved amino acid residue and such substituted amino acid residue may or may not be one encoded by the genetic code, or 2) one in which one or more of the amino acid residues includes a substituent group, or 3) one in which the mutated PAPAP is fused with another compound, such as a compound to increase the half-life of the polypeptide (for example, polyethylene glycol), or 4) one in which the additional amino acids are fused to the mutated PAPAP, such as a leader or secretory sequence or a sequence which is employed for purification of the mutated PAPAP or a preprotein sequence. Such variants are deemed to be within the scope of those skilled in the art.

A polypeptide fragment is a polypeptide having a sequence that entirely is the same as part but not all of a given polypeptide sequence, preferably a polypeptide encoded by a PAPAP gene and variants thereof.

In the case of an amino acid substitution in the amino acid sequence of a polypeptide according to the invention, one or several amino acids can be replaced by "equivalent" amino acids. The expression "equivalent" amino acid is used herein to designate any amino acid that may be substituted for one of the amino acids having similar properties, such that one skilled in the art of peptide chemistry would expect the secondary structure and hydropathic nature of the polypeptide to be substantially unchanged. Generally, the following groups of amino acids represent equivalent changes: (1) Ala, Pro, Gly, Glu, Asp, Gln, Asn, Ser, Thr; (2) Cys, Ser, Tyr, Thr; (3) Val, Ile, Leu, Met, Ala, Phe; (4) Lys, Arg, H is; (5) Phe, Tyr, Trp, His.

A specific embodiment of a modified PAPAP peptide molecule of interest according to the present invention, includes, but is not limited to, a peptide molecule which is resistant to proteolysis, is a peptide in which the —CONH— peptide bond is modified and replaced by a (CH2NH) reduced bond, a (NHCO) retro inverso bond, a (CH2-O) methylene-oxy bond, a (CH2-S) thiomethylene bond, a (CH2CH2) carba bond, a (CO—CH$_2$) cetomethylene bond, a (CHOH—CH2) hydroxyethylene bond), a (N—N) bound, a E-alcene bond or also a —CH=CH— bond. The invention also encompasses a huma PAPAP polypeptide or a fragment or a variant thereof in which at least one peptide bond has been modified as described above.

Such fragments may be "free-standing", i.e. not part of or fused to other polypeptides, or they may be comprised within a single larger polypeptide of which they form a part or region. However, several fragments may be comprised within a single larger polypeptide.

As representative examples of polypeptide fragments of the invention, there may be mentioned those which have from about 5, 6, 7, 8, 9 or 10 to 15, 10 to 20, 15 to 40, or 30 to 55 amino acids long. Preferred are those fragments containing at least one amino acid mutation in the PAPAP protein.

Identity Between Nucleic Acids or Polypeptides

The terms "percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Homology is evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988; Altschul et al., 1990; Thompson et al., 1994; Higgins et al., 1996; Altschul et al., 1990; Altschul et al., 1993). In a particularly preferred embodiment, protein and nucleic acid sequence homologies are evaluated using the Basic Local Alignment Search Tool ("BLAST") which is well known in the art (see, e.g., Karlin and Altschul, 1990; Altschul et al., 1990, 1993, 1997). In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., 1992; Henikoff and Henikoff 1993). Less preferably, the PAM or PAM250 matrices may also be used (see, e.g., Schwartz and Dayhoff, eds., 1978). The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (see, e.g., Karlin and Altschul, 1990).

The BLAST programs may be used with the default parameters or with modified parameters provided by the user.

Stringent Hybridization Conditions

For the purpose of defining such a hybridizing nucleic acid according to the invention, the stringent hybridization conditions are the followings:

the hybridization step is realized at 65° C. in the presence of 6×SSC buffer, 5×Denhardt's solution, 0,5% SDS and 100 µg/ml of salmon sperm DNA.

The hybridization step is followed by four washing steps:
two washings during 5 min, preferably at 65° C. in a 2×SSC and 0.1% SDS buffer;
one washing during 30 min, preferably at 65° C. in a 2×SSC and 0.1% SDS buffer,
one washing during 10 min, preferably at 65° C. in a 0.1×SSC and 0.1% SDS buffer, these hybridization conditions being suitable for a nucleic acid molecule of about 20 nucleotides in length. There is no need to say that the hybridization conditions described above are to be adapted according to the length of the desired nucleic acid, following techniques well known to the one skilled in the art. The suitable hybridization conditions may for example be adapted according to the teachings disclosed in the book of Hames and Higgins (1985).

Genomic Sequences of the PAPAP Gene

The present invention concerns the genomic sequence of PAPAP. The present invention encompasses the PAPAP gene, or PAPAP genomic sequences consisting of, consisting essentially of, or comprising the sequence of SEQ ID NO: 3, a sequence complementary thereto, as well as fragments and variants thereof. These polynucleotides may be purified, isolated, or recombinant.

PAPAP nucleic acids include isolated, purified, or recombinant polynucleotides comprising, consisting essentially of, or consisting of a contiguous span of at least 12, 15, 18, 20, 25, 30, 35, 40, 50, 60, 70, 80, 90, 100, 150, 200, 500, or 1000 nucleotides of SEQ ID NO: 3 or the complements thereof. PAPAP nucleic acids may also include isolated, purified, or recombinant polynucleotides comprising, consisting essentially of, or consisting of a contiguous span of at least 12, 15, 18, 20, 25, 30, 35, 40, 50, 60, 70, 80, 90, 100, 150, 200, 500, or 1000 nucleotides selected from the group of nucleotide positions 1 to 3038, 1 to 421, 422 to 557, 2158 to 2218 and 2620 to 3039 of SEQ ID NO: 3, or the complements thereof. The invention also encompasses a purified, isolated, or recombinant polynucleotide comprising a nucleotide sequence having at least 70, 75, 80, 85, 90, or 95% nucleotide identity with a nucleotide sequence of SEQ ID NO: 3 or a complementary sequence thereto or a fragment thereof. The nucleotide differences as regards to the nucleotide sequence of SEQ ID NO: 3 may be generally randomly distributed throughout the entire nucleic acid. Nevertheless, preferred nucleic acids are those wherein the nucleotide differences as regards to the nucleotide sequence of SEQ ID NO: 3 are predominantly located outside the coding sequences contained in the exons. These nucleic acids, as well as their fragments and variants, may be used as oligonucleotide primers or probes in order to detect the presence of a copy of the PAPAP gene in a test sample, or alternatively in order to amplify a target nucleotide sequence within the PAPAP sequences. Another object of the invention consists of a purified, isolated, or recombinant nucleic acid that hybridizes with the nucleotide sequence of SEQ ID NO: 3 or a complementary sequence thereto or a variant thereof, under stringent hybridization conditions as defined above.

While this section is entitled "Genomic Sequences of PAPAP," it should be noted that nucleic acid fragments of any size and sequence may also be comprised by the polynucleotides described in this section, flanking the genomic sequences of PAPAP on either side or between two or more such genomic sequences.

PAPAP cDNA Sequences

The expression of the PAPAP gene has been shown to lead to the production of at least one mRNA species, the nucleic acid sequence of which is set forth in SEQ ID NO: 1.

Another object of the invention is a purified, isolated, or recombinant nucleic acid comprising the nucleotide sequence of SEQ ID NO: 1, complementary sequences thereto, as well as allelic variants, and fragments thereof. Moreover, preferred polynucleotides of the invention include purified, isolated, or recombinant PAPAP cDNAs consisting of, consisting essentially of, or comprising the sequence of SEQ ID NO: 1. Particularly preferred nucleic acids of the invention include isolated, purified, or recombinant polynucleotides comprising, consisting essentially of, or consisting of a contiguous span of at least 12, 15, 18, 20, 25, 30, 35, 40, 50, 60, 70, 80, 90, 100, 150, 200, 500, or 1000 nucleotides of SEQ ID NO: 1 or the complements thereof. Nucleic acids of the invention also include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID NO: 1 or the complements thereof, wherein said contiguous span comprises at least 1, 2, 3, 5, or 10 of the following nucleotide positions of SEQ ID NO: 1: 1 to 140, 141 to 460, 460 to 690, 87 to 346 and 691 to 1104. Additional preferred embodiments of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID NO: 1 or the complements thereof, wherein said contiguous span comprises a biallelic marker.

The invention also pertains to a purified or isolated nucleic acid comprising a polynucleotide having at least 95% nucleotide identity with a polynucleotide of SEQ ID NO: 1, advantageously 99% nucleotide identity, preferably 99.5% nucleotide identity and most preferably 99.8% nucleotide identity with a polynucleotide of SEQ ID NO: 1, or a sequence complementary thereto or a biologically active fragment thereof.

Another object of the invention relates to purified, isolated or recombinant nucleic acids comprising a polynucleotide that hybridizes, under the stringent hybridization conditions defined herein, with a polynucleotide of SEQ ID NO: 1, or a sequence complementary thereto or a variant thereof or a biologically active fragment thereof.

The cDNA of SEQ ID NO: 1 includes a 5'-UTR region starting from the nucleotide at position 1 and ending at the nucleotide in position 86 of SEQ ID NO: 1. The cDNA of SEQ ID NO: 1 includes a 3'-UTR region starting from the nucleotide at position 347 and ending at the nucleotide at position 1104 of SEQ ID NO: 1. The polyadenylation signal starts from the nucleotide at position 1085 and ends at the nucleotide in position 1104 of SEQ ID NO: 1.

Consequently, the invention concerns a purified, isolated, and recombinant nucleic acid comprising a nucleotide sequence of the 5'UTR of the PAPAP cDNA, a sequence complementary thereto, or an allelic variant thereof. The invention also concerns a purified, isolated, and recombinant nucleic acid comprising a nucleotide sequence of the 3'UTR of the PAPAP cDNA, a sequence complementary thereto, or an allelic variant thereof.

While this section is entitled "PAPAP cDNA Sequences," it should be noted that nucleic acid fragments of any size and sequence may also be comprised by the polynucleotides described in this section, flanking the genomic sequences of PAPAP on either side or between two or more such genomic sequences.

Coding Regions

The PAPAP open reading frame is contained in the corresponding mRNA of SEQ ID NO: 1. More precisely, the effective PAPAP coding sequence (CDS) includes the region between nucleotide position 87 (first nucleotide of the ATG codon) and nucleotide position 346 (end nucleotide of the TGA codon) of SEQ ID NO: 1. The present invention also embodies isolated, purified, and recombinant polynucleotides which encode a polypeptides comprising a contiguous span of at least 6 amino acids, preferably at least 8 or 10 amino acids, more preferably at least 12, 15, 20, 25, 30, 40, 50, or 100 amino acids of SEQ ID NO: 2.

The above disclosed polynucleotide that contains the coding sequence of the PAPAP gene may be expressed in a desired host cell or a desired host organism, when this polynucleotide is placed under the control of suitable expression signals. The expression signals may be either the expression signals contained in the regulatory regions in the PAPAP gene of the invention or in contrast the signals may be exogenous regulatory nucleic sequences. Such a polynucleotide, when placed under the suitable expression signals, may also be inserted in a vector for its expression and/or amplification.

Regulatory Sequences Of PAPAP

As mentioned, the genomic sequence of the PAPAP gene contains regulatory sequences in the non-coding 5'-flanking region and in the non-coding 3'-flanking region that border the PAPAP coding region containing the three exons of this gene.

Polynucleotides derived from the 5' and 3' regulatory regions are useful in order to detect the presence of at least a copy of a nucleotide sequence of SEQ ID NO: 3 or a fragment thereof in a test sample.

The promoter activity of the 5' regulatory regions contained in PAPAP can be assessed as described below.

In order to identify the relevant biologically active polynucleotide fragments or variants of SEQ ID NO: 3, one of skill in the art will refer to the book of Sambrook et al. (Sambrook, 1989) which describes the use of a recombinant vector carrying a marker gene (i.e. beta galactosidase, chloramphenicol acetyl transferase, etc.) the expression of which will be detected when placed under the control of a biologically active polynucleotide fragments or variants of SEQ ID NO: 3. Genomic sequences located upstream of the first exon of the PAPAP gene are cloned into a suitable promoter reporter vector, such as the pSEAP-Basic, pSEAP-Enhancer, pβgal-Basic, pβgal-Enhancer, or pEGFP-1 Promoter Reporter vectors available from Clontech, or pGL2-basic or pGL3-basic promoterless luciferase reporter gene vector from Promega. Briefly, each of these promoter reporter vectors include multiple cloning sites positioned upstream of a reporter gene encoding a readily assayable protein such as secreted alkaline phosphatase, luciferase, β galactosidase, or green fluorescent protein. The sequences upstream the PAPAP coding region are inserted into the cloning sites upstream of the reporter gene in both orientations and introduced into an appropriate host cell. The level of reporter protein is assayed and compared to the level obtained from a vector which lacks an insert in the cloning site. The presence of an elevated expression level in the vector containing the insert with respect to the control vector indicates the presence of a promoter in the insert. If necessary, the upstream sequences can be cloned into vectors which contain an enhancer for increasing transcription levels from weak promoter sequences. A significant level of expression above that observed with the vector lacking an insert indicates that a promoter sequence is present in the inserted upstream sequence.

Promoter sequence within the upstream genomic DNA may be further defined by constructing nested 5' and/or 3' deletions in the upstream DNA using conventional techniques such as Exonuclease III or appropriate restriction endonuclease digestion. The resulting deletion fragments can be inserted into the promoter reporter vector to determine whether the deletion has reduced or obliterated promoter activity, such as described, for example, by Coles et al. (1998), the disclosure of which is incorporated herein by reference in its entirety. In this way, the boundaries of the promoters may be defined. If desired, potential individual regulatory sites within the promoter may be identified using site directed mutagenesis or linker scanning to obliterate potential transcription factor binding sites within the promoter individually or in combination. The effects of these mutations on transcription levels may be determined by inserting the mutations into cloning sites in promoter reporter vectors. This type of assay is well-known to those skilled in the art and is described in WO 97/17359, U.S. Pat. No. 5,374,544; EP 582 796; U.S. Pat. No. 5,698,389; U.S. Pat. No.

5,643,746; U.S. Pat. No. 5,502,176; and U.S. Pat. No. 5,266,488; the disclosures of which are incorporated by reference herein in their entirety.

The strength and the specificity of the promoter of the PAPAP gene can be assessed through the expression levels of a detectable polynucleotide operably linked to the PAPAP promoter in different types of cells and tissues. The detectable polynucleotide may be either a polynucleotide that specifically hybridizes with a predefined oligonucleotide probe, or a polynucleotide encoding a detectable protein, including a PAPAP polypeptide or a fragment or a variant thereof. This type of assay is well-known to those skilled in the art and is described in U.S. Pat. No. 5,502,176; and U.S. Pat. No. 5,266,488; the disclosures of which are incorporated by reference herein in their entirety. Some of the methods are discussed in more detail below.

Polynucleotides carrying the regulatory elements located at the 5' end and at the 3' end of the PAPAP coding region may be advantageously used to control the transcriptional and translational activity of an heterologous polynucleotide of interest.

Thus, the present invention also concerns a purified or isolated nucleic acid comprising a polynucleotide which is selected from the group consisting of the 5' and 3' regulatory regions, or a sequence complementary thereto or a biologically active fragment or variant thereof. In one aspect, the "5' regulatory region" comprises the nucleotide sequence located between positions 1 and 421 of SEQ ID NO: 3. In one aspect, the "3' regulatory region" comprises the nucleotide sequence located between positions 3040 and 3189 of SEQ ID NO: 3.

The invention also pertains to a purified or isolated nucleic acid comprising a polynucleotide having at least 95% nucleotide identity with a polynucleotide selected from the group consisting of the 5' and 3' regulatory regions, advantageously 99% nucleotide identity, preferably 99.5% nucleotide identity and most preferably 99.8% nucleotide identity with a polynucleotide selected from the group consisting of the 5' and 3' regulatory regions, or a sequence complementary thereto or a variant thereof or a biologically active fragment thereof.

Another object of the invention consists of purified, isolated or recombinant nucleic acids comprising a polynucleotide that hybridizes, under the stringent hybridization conditions defined herein, with a polynucleotide selected from the group consisting of the nucleotide sequences of the 5'- and 3'-regulatory regions, or a sequence complementary thereto or a variant thereof or a biologically active fragment thereof.

Preferred fragments of the 5' regulatory region have a length of about 1500 or 1000 nucleotides, preferably of about 500 nucleotides, more preferably about 400 nucleotides, even more preferably 300 nucleotides and most preferably about 200 nucleotides.

Preferred fragments of the 3' regulatory region are at least 50, 100, 150, 200, 300 or 400 bases in length.

"Biologically active" polynucleotide derivatives of SEQ ID NO: 3 are polynucleotides comprising or alternatively consisting in a fragment of said polynucleotide which is functional as a regulatory region for expressing a recombinant polypeptide or a recombinant polynucleotide in a recombinant cell host. It could act either as an enhancer or as a repressor.

For the purpose of the invention, a nucleic acid or polynucleotide is "functional" as a regulatory region for expressing a recombinant polypeptide or a recombinant polynucleotide if said regulatory polynucleotide contains nucleotide sequences which contain transcriptional and translational regulatory information, and such sequences are "operably linked" to nucleotide sequences which encode the desired polypeptide or the desired polynucleotide.

The regulatory polynucleotides of the invention may be prepared from the nucleotide sequence of SEQ ID NO: 3 by cleavage using suitable restriction enzymes, as described for example in Sambrook et al. (1989). The regulatory polynucleotides may also be prepared by digestion of SEQ ID NO: 3 by an exonuclease enzyme, such as Bal31 (Wabiko et al., 1986). These regulatory polynucleotides can also be prepared by nucleic acid chemical synthesis, as described elsewhere in the specification.

The regulatory polynucleotides according to the invention may be part of a recombinant expression vector that may be used to express a coding sequence in a desired host cell or host organism. The recombinant expression vectors according to the invention are described elsewhere in the specification.

A preferred 5'-regulatory polynucleotide of the invention includes the 5'-untranslated region (5'-UTR) of the PAPAP cDNA, or a biologically active fragment or variant thereof.

A preferred 3'-regulatory polynucleotide of the invention includes the 3'-untranslated region (3'-UTR) of the PAPAP cDNA, or a biologically active fragment or variant thereof.

A further object of the invention consists of a purified or isolated nucleic acid comprising:

a) a nucleic acid comprising a regulatory nucleotide sequence selected from the group consisting of:
  (i) a nucleotide sequence comprising a polynucleotide of the 5' regulatory region or a complementary sequence thereto;
  (ii) a nucleotide sequence comprising a polynucleotide having at least 95% of nucleotide identity with the nucleotide sequence of the 5' regulatory region or a complementary sequence thereto;
  (iii) a nucleotide sequence comprising a polynucleotide that hybridizes under stringent hybridization conditions with the nucleotide sequence of the 5' regulatory region or a complementary sequence thereto; and
  (iv) a biologically active fragment or variant of the polynucleotides in (i), (ii) and (iii);

b) a polynucleotide encoding a desired polypeptide or a nucleic acid of interest, operably linked to the nucleic acid defined in (a) above;

c) Optionally, a nucleic acid comprising a 3'-regulatory polynucleotide, preferably a 3'-regulatory polynucleotide of the PAPAP gene.

In a specific embodiment of the nucleic acid defined above, said nucleic acid includes the 5'-untranslated region (5'-UTR) of the PAPAP cDNA, or a biologically active fragment or variant thereof.

In a second specific embodiment of the nucleic acid defined above, said nucleic acid includes the 3'-untranslated region (3'-UTR) of the PAPAP cDNA, or a biologically active fragment or variant thereof.

The regulatory polynucleotide of the 5' regulatory region, or its biologically active fragments or variants, is operably linked at the 5'-end of the polynucleotide encoding the desired polypeptide or polynucleotide.

The regulatory polynucleotide of the 3' regulatory region, or its biologically active fragments or variants, is advantageously operably linked at the 3'-end of the polynucleotide encoding the desired polypeptide or polynucleotide.

The desired polypeptide encoded by the above-described nucleic acid may be of various nature or origin, encompassing proteins of prokaryotic or eukaryotic origin. Among the polypeptides expressed under the control of a PAPAP regulatory region include bacterial, fungal or viral antigens. Also encompassed are eukaryotic proteins such as intracellular proteins, like "house keeping" proteins, membrane-bound proteins, like receptors, and secreted proteins like endogenous mediators such as cytokines. The desired polypeptide may be the PAPAP protein, especially the protein of the amino acid sequence of SEQ ID NO: 2, or a fragment or a variant thereof.

The desired nucleic acids encoded by the above-described polynucleotide, usually an RNA molecule, may be complementary to a desired coding polynucleotide, for example to the PAPAP coding sequence, and thus useful as an antisense polynucleotide.

Such a polynucleotide may be included in a recombinant expression vector in order to express the desired polypeptide or the desired nucleic acid in host cell or in a host organism. Suitable recombinant vectors that contain a polynucleotide such as described herein are disclosed elsewhere in the specification.

Polynucleotide Constructs

The terms "polynucleotide construct" and "recombinant polynucleotide" are used interchangeably herein to refer to linear or circular, purified or isolated polynucleotides that have been artificially designed and which comprise at least two nucleotide sequences that are not found as contiguous nucleotide sequences in their initial natural environment.

DNA Construct that Enables Directing Temporal and Spatial PAPAP Gene Expression in Recombinant Cell Hosts and in Transgenic Animals In order to study the physiological and phenotypic consequences of a lack of synthesis of the PAPAP protein, both at the cell level and at the multi cellular organism level, the invention also encompasses DNA constructs and recombinant vectors enabling a conditional expression of a specific allele of the PAPAP genomic sequence or cDNA and also of a copy of this genomic sequence or cDNA harboring substitutions, deletions, or additions of one or more bases as regards to the PAPAP nucleotide sequence of SEQ ID NOs: 1 and 3, or a fragment thereof, these base substitutions, deletions or additions being located either in an exon, an intron or a regulatory sequence, but preferably in the 5'-regulatory sequence or in an exon of the PAPAP genomic sequence or within the PAPAP cDNA of SEQ ID NO: 1. In a preferred embodiment, the PAPAP sentience comprises a biallelic marker.

The present invention embodies recombinant vectors comprising any one of the polynucleotides described in the present invention. More particularly, the polynucleotide constructs according to the present invention can comprise any of the polynucleotides described in the "Genomic Sequences Of The PAPAP Gene" section, the "PAPAP cDNA Sequences" section, the "Coding Regions" section, and the "Oligonucleotide Probes And Primers" section.

A first preferred DNA construct is based on the tetracycline resistance operon tet from *E. coli* transposon Tn10 for controlling the PAPAP gene expression, such as described by Gossen et al. (1992, 1995) and Furth et al. (1994). Such a DNA construct contains seven tet operator sequences from Tn10 (tetop) that are fused to either a minimal promoter or a 5'-regulatory sequence of the PAPAP gene, said minimal promoter or said PAPAP regulatory sequence being operably linlked to a polynucleotide of interest that codes either for a sense or an antisense oligonucleotide or for a polypeptide, including a PAPAP polypeptide or a peptide fragment thereof. This DNA construct is functional as a conditional expression system for the nucleotide sequence of interest when the same cell also comprises a nucleotide sequence coding for either the wild type (tTA) or the mutant (rTA) repressor fused to the activating domain of viral protein VP 16 of herpes simplex virus, placed under the control of a promoter, such as the HCMVIE1 enhancer/promoter or the MMTV-LTR. Indeed, a preferred DNA construct of the invention comprise both the polynucleotide containing the tet operator sequences and the polynucleotide containing a sequence coding for the tTA or the rTA repressor.

In a specific embodiment, the conditional expression DNA construct contains the sequence encoding the mutant tetracycline repressor rTA, the expression of the polynucleotide of interest is silent in the absence of tetracycline and induced in its presence.

DNA Constructs Allowing Homologous Recombination: Replacement Vectors

A second preferred DNA construct will comprise, from 5'-end to 3'-end: (a) a first nucleotide sequence that is comprised in the PAPAP genomic sequence; (b) a nucleotide sequence comprising a positive selection marker, such as the marker for neomycine resistance (neo); and (c) a second nucleotide sequence that is comprised in the PAPAP genomic sequence, and is located on the genome downstream the first PAPAP nucleotide sequence (a).

In a preferred embodiment, this DNA construct also comprises a negative selection marker located upstream the nucleotide sequence (a) or downstream the nucleotide sequence (c). Preferably, the negative selection marker comprises the thymidine kinase (tk) gene (Thomas et al., 1986), the hygromycine beta gene (Te Riele et al., 1990), the hprt gene (Van der Lugt et al., 1991; Reid et al., 1990) or the Diphteria toxin A fragment (Dt-A) gene (Nada et al., 1993; Yagi et al. 1990). Preferably, the positive selection marker is located within a PAPAP exon sequence so as to interrupt the sequence encoding a PAPAP protein. These replacement vectors are described, for example, by Thomas et al. (1986; 1987), Mansour et al. (1988) and Koller et al. (1992).

The first and second nucleotide sequences (a) and (c) may be indifferently located within a PAPAP regulatory sequence, an intronic sequence, an exon sequence or a sequence containing both regulatory and/or intronic and/or exon sequences. The size of the nucleotide sequences (a) and (c) ranges from 1 to 50 kb, preferably from 1 to 10 kb, more preferably from 2 to 6 kb and most preferably from 2 to 4 kb.

DNA Constructs Allowing Homologous Recombination: Cre-LoxP System.

These new DNA constructs make use of the site specific recombination system of the P1 phage. The P1 phage possesses a recombinase called Cre which interacts specifically with a 34 base pairs loxP site. The loxP site is composed of two palindromic sequences of 13 bp separated by a 8 bp conserved sequence (Hoess et al., 1986). The recombination by the Cre enzyme between two loxP sites having an identical orientation leads to the deletion of the DNA fragment.

The Cre-loxP system used in combination with a homologous recombination technique has been first described by Gu et al. (1993, 1994). Briefly, a nucleotide sequence of interest to be inserted in a targeted location of the genome harbors at least two loxP sites in the same orientation and located at the respective ends of a nucleotide sequence to be excised from the recombinant genome. The excision event requires the presence of the recombinase (Cre) enzyme within the nucleus of the recombinant cell host. The recombinase enzyme may be brought at the desired time either by (a) incubating the recombinant cell hosts in a culture medium containing this enzyme, by injecting the Cre enzyme directly into the desired cell, such as described by Araki et al. (1995), or by lipofection of the enzyme into the cells, such as described by Baubonis et al. (1993); (b) transfecting the cell host with a vector comprising the Cre coding sequence operably linked to a promoter functional in the recombinant cell host, which promoter being optionally inducible, said vector being introduced in the recombinant cell host, such as described by Gu et al. (1993) and Sauer et al. (1988); (c) introducing in the genome of the cell host a polynucleotide comprising the Cre coding sequence operably linked to a promoter functional in the recombinant cell host, which promoter is optionally inducible, and said polynucleotide being inserted in the genome of the cell host either by a random insertion event or an homologous recombination event, such as described by Gu et al. (1994).

In a specific embodiment, the vector containing the sequence to be inserted in the PAPAP gene by homologous recombination is constructed in such a way that selectable markers are flanked by loxP sites of the same orientation, it is possible, by treatment by the Cre enzyme, to eliminate the selectable markers while leaving the PAPAP sequences of interest that have been inserted by an homologous recombination event. Again, two selectable markers are needed: a positive selection marker to select for the recombination event and a negative selection marker to select for the homologous recombination event. Vectors and methods using the Cre-loxP system are described by Zou et al. (1994).

Thus, a third preferred DNA construct of the invention comprises, from 5'-end to 3'-end: (a) a first nucleotide sequence that is comprised in the PAPAP genomic sequence; (b) a nucleotide sequence comprising a polynucleotide encoding a positive selection marker, said nucleotide sequence comprising additionally two sequences defining a site recognized by a recombinase, such as a loxP site, the two sites being placed in the same orientation; and (c) a second nucleotide sequence that is comprised in the PAPAP genomic sequence, and is located on the genome downstream of the first PAPAP nucleotide sequence (a).

The sequences defining a site recognized by a recombinase, such as a loxP site, are preferably located within the nucleotide sequence (b) at suitable locations bordering the nucleotide sequence for which the conditional excision is sought. In one specific embodiment, two loxP sites are located at each side of the positive selection marker sequence, in order to allow its excision at a desired time after the occurrence of the homologous recombination event.

In a preferred embodiment of a method using the third DNA construct described above, the excision of the polynucleotide fragment bordered by the two sites recognized by a recombinase, preferably two loxP sites, is performed at a desired time, due to the presence within the genome of the recombinant host cell of a sequence encoding the Cre enzyme operably linked to a promoter sequence, preferably an inducible promoter, more preferably a tissue-specific promoter sequence and most preferably a promoter sequence which is both inducible and tissue-specific, such as described by Gu et al. (1994).

The presence of the Cre enzyme within the genome of the recombinant cell host may result from the breeding of two transgenic animals, the first transgenic animal bearing the PAPAP-derived sequence of interest containing the loxP sites as described above and the second transgenic animal bearing the Cre coding sequence operably linked to a suitable promoter sequence, such as described by Gu et al. (1994).

Spatio-temporal control of the Cre enzyme expression may also be achieved with an adenovirus based vector that contains the Cre gene thus allowing infection of cells, or in vivo infection of organs, for delivery of the Cre enzyme, such as described by Anton and Graham (1995) and Kanegae et al. (1995).

The DNA constructs described above may be used to introduce a desired nucleotide sequence of the invention, preferably a PAPAP genomic sequence or a PAPAP cDNA sequence, and most preferably an altered copy of a PAPAP genomic or cDNA sequence, within a predetermined location of the targeted genome, leading either to the generation of an altered copy of a targeted gene (knock-out homologous recombination) or to the replacement of a copy of the targeted gene by another copy sufficiently homologous to allow an homologous recombination event to occur (knock-in homologous recombination). In a specific embodiment, the DNA constructs described above may be used to introduce a PAPAP genomic sequence or a PAPAP cDNA sequence comprising at least one biallelic marker.

Nuclear Antisense DNA Constructs

Other compositions containing a vector of the invention comprising an oligonucleotide fragment of the nucleic sequence SEQ ID NO: cDNA, preferably a fragment including the start codon of the PAPAP gene, as an antisense tool that inhibits the expression of the corresponding PAPAP gene. Preferred methods using antisense polynucleotide according to the present invention are the procedures described by Sczakiel et al. (1995) or those described in PCT Application No WO 95/24223, the disclosures of which are incorporated by reference herein in their entirety.

Preferably, the antisense tools are chosen among the polynucleotides (15-200 bp long) that are complementary to the 5' end of the PAPAP mRNA. In one embodiment, a combination of different antisense polynucleotides complementary to different parts of the desired targeted gene are used.

Preferred antisense polynucleotides according to the present invention are complementary to a sequence of the mRNAs of PAPAP that contains either the translation initiation codon ATG or a splicing site. Further preferred antisense polynucleotides according to the invention are complementary of the splicing site of the PAPAP mRNA.

Preferably, the antisense polynucleotides of the invention have a 3' polyadenylation signal that has been replaced with a self-cleaving ribozyme sequence, such that RNA polymerase II transcripts are produced without poly(A) at their 3' ends, these antisense polynucleotides being incapable of export from the nucleus, such as described by Liu et al. (1994). In a preferred embodiment, these PAPAP antisense polynucleotides also comprise, within the ribozyme cassette, a histone stem-loop structure to stabilize cleaved transcripts against 3'-5' exonucleolytic degradation, such as the structure described by Eckner et al. (1991).

Olilonucleotide Probes And Primers Polynucleotides derived from the PAPAP gene are useful in order to detect the presence of at least a copy of a nucleotide sequence of SEQ ID NO: 1 or 3, or a fragment, complement, or variant thereof in a test sample. Such methods are useful, e.g., in the diagnosis of disorders resulting from or associated with an alteration in PAPAP gene expression, as well as to confirm PAPAP gene expression in cells or samples in which PAPAP expression has been induced, e.g., for experimental or therapeutic purposes.

Particularly preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID NO: 3 or the complements thereof. Probes and primers also include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID NO: 3 or the complements thereof, wherein said contiguous span comprises at least one of the following nucleotide positions of SEQ ID NO: 3: 1 to 3038, 1 to 421, 422 to 557, 2158 to 2218 and 2620 to 3039. Additional preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID NO: 1 or the complements thereof. Further preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID NO: 1 or the complements thereof, wherein said contiguous span comprises at least one of the following nucleotide positions of SEQ ID NO: 1: 1 to 140, 141 to 460, 460 to 690, 87 to 346 and 691 to 1104.

Thus, the invention also relates to nucleic acid probes characterized in that they hybridize specifically, under the stringent hybridization conditions defined above, with a nucleic acid selected from the group consisting of the nucleotide sequences of SEQ ID NOs: 1 and 3, or a variant thereof or a sequence complementary thereto.

In one embodiment the invention encompasses isolated, purified, and recombinant polynucleotides consisting of, or consisting essentially of a contiguous span of 8 to 50 nucleotides of any one of SEQ ID NOs: 1, 3 and the complement thereof, wherein said span includes a PAPAP-related biallelic marker in said sequence or a biallelic marker in linkage disequilibrium with PAPAP; optionally, wherein said contiguous span is 18 to 35 nucleotides in length and said biallelic marker is within 4 nucleotides of the center of said polynucleotide; optionally, wherein said polynucleotide consists of said contiguous span and said contiguous span is 25 nucleotides in length and said biallelic marker is at the center of said polynucleotide; optionally, wherein the 3' end of said contiguous span is present at the 3' end of said polynucleotide; and optionally, wherein the 3' end of said contiguous span is located at the 3' end of said polynucleotide and said biallelic marker is present at the 3' end of said polynucleotide.

In another embodiment the invention encompasses isolated, purified and recombinant polynucleotides comprising, consisting of, or consisting essentially of a contiguous span of 8 to 50 nucleotides of SEQ ID NOs: 1, 3, or the complements thereof, wherein the 3' end of said contiguous span is located at the 3' end of said polynucleotide, and wherein the 3' end of said polynucleotide is located within 20 nucleotides upstream of a PAPAP-related biallelic marker in said sequence or a biallelic marker in linkage disequilibrium therewith.

In an additional embodiment, the invention encompasses polynucleotides for use in hybridization assays, sequencing assays, and enzyme-based mismatch detection assays for determining the identity of the nucleotide at a PAPAP-related biallelic marker in SEQ ID NOs: 1, 3, or the complements thereof, as well as polynucleotides for use in amplifying segments of nucleotides comprising a PAPAP-related biallelic marker in SEQ ID NOs: 1, 3, or the complements thereof.

The invention concerns the use of the polynucleotides according to the invention for determining the identity of the nucleotide at a PAPAP-related biallelic marker, preferably in hybridization assay, sequencing assay, microsequencing assay, or an enzyme-based mismatch detection assay and in amplifying segments of nucleotides comprising a PAPAP-related biallelic marker.

A probe or a primer according to the invention has between 8 and 1000 nucleotides in length, or is specified to be at least 12, 15, 18, 20, 25, 35, 40, 50, 60, 70, 80, 100, 250, 500 or 1000 nucleotides in length. More particularly, the length of these probes and primers can range from 8, 10, 15, 20, or 30 to 100 nucleotides, preferably from 10 to 50, more preferably from 15 to 30 nucleotides. Shorter probes and primers tend to lack specificity for a target nucleic acid sequence and generally require cooler temperatures to form sufficiently stable hybrid complexes with the template. Longer probes and primers are expensive to produce and can sometimes self-hybridize to form hairpin structures. The appropriate length for primers and probes under a particular set of assay conditions may be empirically determined by one of skill in the art.

The formation of stable hybrids depends on the melting temperature (Tm) of the DNA. The Tm depends on the length of the primer or probe, the ionic strength of the solution and the G+C content. The higher the G+C content of the primer or probe, the higher is the melting temperature because G:C pairs are held by three H bonds whereas A:T pairs have only two. The GC content in the probes of the invention usually ranges between 10 and 75%, preferably between 35 and 60%, and more preferably between 40 and 55%.

The primers and probes can be prepared by any suitable method, including, for example, cloning and restriction of appropriate sequences and direct chemical synthesis by a method such as the phosphodiester method of Narang et al. (1979), the phosphodiester method of Brown et al. (1979), the diethylphosphoramidite method of Beaucage et al. (1981) and the solid support method described in EP 0 707 592.

Detection probes are generally nucleic acid sequences or uncharged nucleic acid analogs such as, for example peptide nucleic acids which are disclosed in International Patent Application WO 92/20702, morpholino analogs which are described in U.S. Pat. Nos. 5,185,444; 5,034,506 and 5,142,047. The probe may have to be rendered "non-extendable" in that additional dNTPs cannot be added to the probe. In and of themselves analogs usually are non-extendable and nucleic acid probes can be rendered non-extendable by modifying the 3' end of the probe such that the hydroxyl group is no longer capable of participating in elongation. For example, the 3' end of the probe can be functionalized with the capture or detection label to thereby consume or otherwise block the hydroxyl group. Alternatively, the 3' hydroxyl group simply can be cleaved, replaced or modified, U.S. patent application Ser. No. 07/049,061 filed Apr. 19, 1993 describes modifications, which can be used to render a probe non-extendable.

Any of the polynucleotides of the present invention can be labeled, if desired, by incorporating any label known in the art to be detectable by spectroscopic, photochemical, biochemical, immunochemical, or chemical means. For example, useful labels include radioactive substances (including, $^{32}$P, $^{35}$S, $^{3}$H, $^{125}$I), fluorescent dyes (including, 5-bromodesoxyuridin, fluorescein, acetylaminofluorene, digoxigenin) or biotin. Preferably, polynucleotides are labeled at their 3' and 5' ends. Examples of non-radioactive labeling of nucleic acid fragments are described in the French patent No. FR-7810975 or by Urdea et al. (1988) or Sanchez-Pescador et al. (1988). In addition, the probes according to the present invention may have structural characteristics such that they allow the signal amplification, such structural characteristics being, for example, branched DNA probes as those described by Urdea et al. in 1991 or in European patent No. EP 0 225 807 (Chiron).

A label can also be used to capture the primer, so as to facilitate the immobilization of either the primer or a primer extension product, such as amplified DNA, on a solid support. A capture label is attached to the primers or probes and can be a specific binding member which forms a binding pair with the solid's phase reagent's specific binding member (e.g. biotin and streptavidin) Therefore depending upon the type of label carried by a polynucleotide or a probe, it may be employed to capture or to detect the target DNA. Further, it will be understood that the polynucleotides, primers or probes provided herein, may, themselves, serve as the capture label. For example, in the case where a solid phase reagent's binding member is a nucleic acid sequence, it may be selected such that it binds a complementary portion of a primer or probe to thereby immobilize the primer or probe to the solid phase. In cases where a polynucleotide probe itself serves as the binding member, those skilled in the art will recognize that the probe will contain a sequence or "tail" that is not complementary to the target. In the case where a polynucleotide primer itself serves as the capture label, at least a portion of the primer will be free to hybridize with a nucleic acid on a solid phase. DNA Labeling techniques are well known to the skilled technician.

The probes of the present invention are useful for a number of purposes. They can be notably used in Southern hybridization to genomic DNA. The probes can also be used to detect PCR amplification products. They may also be used to detect mismatches in the PAPAP gene or mRNA using other techniques.

Any of the polynucleotides, primers and probes of the present invention can be conveniently immobilized on a solid support. Solid supports are known to those skilled in the art and include the walls of wells of a reaction tray, test tubes, polystyrene beads, magnetic beads, nitrocellulose strips, membranes, microparticles such as latex particles, sheep (or other animal) red blood cells, duracytes and others. The solid support is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and duracytes are all suitable examples. Suitable methods for immobilizing nucleic acids on solid phases include ionic, hydrophobic, covalent interactions and the like. A solid support, as used herein, refers to any material which is insoluble, or can be made insoluble by a subsequent reaction. The solid support can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid support and which has the ability to immobilize the capture reagent through a specific binding reaction. The receptor molecule enables the indirect binding of the capture reagent to a solid support material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, Duracytes® and other configurations known to those of ordinary skill in the art. The polynucleotides of the invention can be attached to or immobilized on a solid support individually or in groups of at least 2, 5, 8, 10, 12, 15, 20, or 25 distinct polynucleotides of the invention to a single solid support. In addition, polynucleotides other than those of the invention may be attached to the same solid support as one or more polynucleotides of the invention.

Consequently, the invention also comprises a method for detecting the presence of a nucleic acid comprising a nucleotide of SEQ ID NOs: 1 or 3, a fragment or a variant thereof and a complementary sequence thereto in a sample, said method comprising the following steps of:

a) bringing into contact a nucleic acid probe or a plurality of nucleic acid probes which can hybridize with a nucleotide sequence included in a nucleic acid of SEQ ID NOs: 1 or 3, a fragment or a variant thereof and a complementary sequence thereto and the sample to be assayed; and b) detecting the hybrid complex formed between the probe and a nucleic acid in the sample.

The invention further concerns a kit for detecting the presence of a nucleic acid comprising a nucleotide sequence of SEQ ID NOs: 1 or 3, a fragment or a variant thereof and a complementary sequence thereto in a sample, said kit comprising:

a) a nucleic acid probe or a plurality of nucleic acid probes which can hybridize with a nucleotide sequence included in a nucleic acid of SEQ ID NOs: 1 or 3, a fragment or a variant thereof and a complementary sequence thereto; and b) optionally, the reagents necessary for performing the hybridization reaction.

In a first preferred embodiment of this detection method and kit, said nucleic acid probe or the plurality of nucleic acid probes are labeled with a detectable molecule. In a second preferred embodiment of said method and kit, said nucleic acid probe or the plurality of nucleic acid probes has been immobilized on a substrate.

Oligonucleotide Arrays

A substrate comprising a plurality of oligonucleotide primers or probes of the invention may be used either for detecting or amplifying targeted sequences in the PAPAP gene and may also be used for detecting mutations in the coding or in the non-coding sequences of the PAPAP gene.

Any polynucleotide provided herein may be attached in overlapping areas or at random locations on the solid support. Alternatively the polynucleotides of the invention may be attached in an ordered array wherein each polynucleotide is attached to a distinct region of the solid support which does not overlap with the attachment site of any other polynucleotide. Preferably, such an ordered array of polynucleotides is designed to be "addressable" where the distinct locations are recorded and can be accessed as part of an assay procedure. Addressable polynucleotide arrays typically comprise a plurality of different oligonucleotide probes that are coupled to a surface of a substrate in different known locations. The knowledge of the precise location of each polynucleotides location makes these "addressable" arrays particularly useful in hybridization assays. Any addressable array technology known in the art can be employed with the polynucleotides of the invention. One particular embodiment of these polynucleotide arrays is known as the Genechips™, and has been generally described in U.S. Pat. No. 5,143,854; PCT publications WO 90/15070 and 92/10092. These arrays may generally be produced using mechanical synthesis methods or light directed synthesis methods which incorporate a combination of photolithographic methods and solid phase oligonucleotide synthesis (Fodor et al., 1991). The immobilization of arrays of oligonucleotides on solid supports has been rendered possible by the development of a technology generally identified as "Very Large Scale Immobilized Polymer Synthesis" (VLSIPS™) in which, typically, probes are immobilized in a high density array on a solid surface of a chip. Examples of VLSIPS™ technologies are provided in U.S. Pat. Nos. 5,143,854; and 5,412,087 and in PCT Publications WO 90/15070, WO 92/10092 and WO 95/11995, which describe methods for forming oligonucleotide arrays through techniques such as light-directed synthesis techniques. In designing strategies aimed at providing arrays of nucleotides immobilized on solid supports, further presentation strategies were developed to order and display the oligonucleotide arrays on the chips in an attempt to maximize hybridization patterns and sequence information. Examples of such presentation strategies are disclosed in PCT Publications WO 94/12305, WO 94/11530, WO 97/29212 and WO 97/31256, the disclosures of which are incorporated herein by reference in their entireties.

In another embodiment of the oligonucleotide arrays of the invention, an oligonucleotide probe matrix may advantageously be used to detect mutations occurring in the PAPAP gene and preferably in its regulatory region. For this particular purpose, probes are specifically designed to have a nucleotide sequence allowing their hybridization to the genes that carry known mutations (either by deletion, insertion or substitution of one or several nucleotides). By known mutations, it is meant, mutations on the PAPAP gene that have been identified according, for example to the technique used by Huang et al. (1996) or Samson et al. (1996).

Another technique that is used to detect mutations in the PAPAP gene is the use of a high-density DNA array. Each oligonucleotide probe constituting a unit element of the high density DNA array is designed to match a specific subsequence of the PAPAP genomic DNA or cDNA. Thus, an array consisting of oligonucleotides complementary to subsequences of the target gene sequence is used to determine the identity of the target sequence with the wild gene sequence, measure its amount, and detect differences between the target sequence and the reference wild gene sequence of the PAPAP gene. In one such design, termed 4 L tiled array, is implemented a set of four probes (A, C, G, T), preferably 15-nucleotide oligomers. In each set of four probes, the perfect complement will hybridize more strongly than mismatched probes. Consequently, a nucleic acid target of length L is scanned for mutations with a tiled array containing 4 L probes, the whole probe set containing all the possible mutations in the known wild reference sequence. The hybridization signals of the 15-mer probe set tiled array are perturbed by a single base change in the target sequence. As a consequence, there is a characteristic loss of signal or a "footprint" for the probes flanking a mutation position. This technique is described in Chee et al. (1996).

Consequently, the invention concerns an array of nucleic acid molecules comprising at least one polynucleotide described above as probes and primers. Preferably, the invention concerns an array of nucleic acid comprising at least two polynucleotides described above as probes and primers.

PAPAP Proteins and Polypeptide Fragments:

The term "PAPAP polypeptides" is used herein to embrace all of the proteins and polypeptides of the present invention. Also forming part of the invention are polypeptides encoded by the polynucleotides of the invention, as well as fusion polypeptides comprising such polypeptides. The invention embodies PAPAP proteins from humans, including isolated or purified PAPAP proteins consisting of, consisting essentially of, or comprising the sequence of SEQ ID NO: 2.

As described herein, the PAPAP protein interacts with the g34872 protein or peptide, a genetic susceptibility factor for schizophrenia, bipolar disorder, and related CNS disorders. PAPAP is also a specific inhibitor of calcium/calmodulin kinase II (CaM-KII), a protein kinase involved in glutaminergic synaptic transmission, long term potentiation, learning, memory, and other neuronal activities, as well as a variety of cellular functions, such as cell cycle-related functions. As such, in one embodiment, a "biologically active" PAPAP protein, fragment, variant, or derivative refers to a PAPAP polypeptide having any detectable activity related to any of these processes.

The invention concerns the polypeptide encoded by a nucleotide sequence of SEQ ID NO: 1 or 3, or a complementary sequence thereto or a fragment thereof.

The present invention embodies isolated, purified, and recombinant polypeptides comprising a contiguous span of at least 6 amino acids, preferably at least 8 to 10 amino acids, more preferably at least 12, 15, 20, 25, 30, 40, 50, or 100 amino acids of SEQ ID NO: 2. In other preferred embodiments the contiguous stretch of amino acids comprises the site of a mutation or functional mutation, including a deletion, addition, swap or truncation of the amino acids in the PAPAP protein sequence.

The invention also encompasses purified, isolated, or recombinant polypeptides comprising an amino acid sequence having at least 70, 75, 80, 85, 90, 95, 98 or 99% amino acid identity with the amino acid sequence of SEQ ID NO: 2 or a fragment thereof. The variant polypeptides are included in the present invention regardless of whether they have their normal biological activity. This is because even where a particular polypeptide molecule does not have biological activity, one of skill in the art would still know how to use the polypeptide, for instance, as a vaccine or to generate antibodies. Other uses of the polypeptides of the present invention that do not have PAPAP activity include, inter alia, as epitope tags, in epitope mapping, and as molecular weight markers on SDS-PAGE gels or on molecular sieve gel filtration columns using methods known to those of skill in the art. As described below, the polypeptides of the present invention can also be used to raise polyclonal and monoclonal antibodies, which are useful in assays for detecting PAPAP protein expression or as agonists and antagonists capable of enhancing or inhibiting PAPAP protein function. Further, such polypeptides can be used in the yeast two-hybrid system to "capture" PAPAP protein binding proteins, which are also candidate agonists and antagonists according to the present invention.

In other embodiments, the present invention also concerns complexes formed by PAPAP and g34872 polypeptides. Thus the invention comprises a purified, isolated, or recombinantly produced complex of at least one PAPAP polypeptide and at least one g34872 polypeptide, wherein said PAPAP polypeptide comprises at least 6 amino acids, preferably at least 8 to 10 amino acids, more preferably at least 12, 15, 20, 25, 30, 40, 50, or 100 amino acids of SEQ ID NO: 2. In a preferred embodiment, said g34872 polypeptide comprises at least 6 amino acids, preferably at least 8 to 10 amino acids of SEQ ID NO: 5. Analogous complexes between PAPAP and CaM-II kinases are also encompassed by the present invention.

Additionally, as suggested by further analysis of the PAPAP polypeptide structure, the PAPAP polypeptide of the invention may comprise an N-glycosylation site (ASP) at amino acid positions 69-72 (amino acids NNTD). Furthermore, the PAPAP polypeptide of the invention may comprise a protein kinase C phosphorylation site at amino acid positions 26-28 (SCR), 53-55 (SKR), 71-73 (TDK) and 80-82 (SPK). Additionally, the PAPAP polypeptide of may comprise a N-myristoylation site at amino acid positions 18-23 (GGDZGQ), 22-27 (GQIFSC) and 37-42 (GAGQNK). Other structural aspects include ASP & GLU racemase motifs at amino acid positions 8 to 16 and 9 to 16 (amino acids D—PYG).

In addition to its association with schizophrenia and bipolar disorder through interaction with g34872, the PAPAP polypeptide also shares sequence homology with the brain-specific calcium/calmodulin dependent protein kinase II inhibitor (CaM-KIIN) (see, e.g., GenBank accession number AF271156.1). CaM-KII is expressed most strongly in the frontal cortex, hippocampus, and inferios colliculus, consistent with a role in learning and memory, as well as with its playing a role in schizophrenia and bipolar disorder. Accordingly, in one embodiment, the present invention provides a method of inhibiting CaM-KII in a cell or an individual, the method comprising administering to the cell or the individual a compound that increases PAPAP levels or activity in the cell or individual. Such compounds may include PAPAP polynucleotides, polypeptides, or any other agents that cause an increase in PAPAP expression or activity. Alternatively, the present invention provides a method of increasing CaM-KII activity in a cell or an individual, the method comprising administering to the cell or the individual a compound that decreases PAPAP levels or activity in the cell or individual. Such a compound may include antisense, antibodies, ribozymes, dominant negative forms, or any other compound that inhibits PAPAP expression or activity. Any cell type can be used in such methods, preferably neurons, glial cells, or other cells within the nervous system. Such methods can be performed on any animal, preferably mammals, and most preferably humans.

In another aspect, PAPAP may act as a molecular chaperone; for example, PAPAP may enhance or prevent the interaction or binding of g34872 and a g34872 receptor. In another aspect, PAPAP may interact functionally in a signaling pathway involving g34872. PAPAP proteins are preferably isolated from human or mammalian tissue samples or expressed from human or mammalian genes.

The PAPAP polypeptides of the invention can be made using routine expression methods known in the art. The polynucleotide encoding the desired polypeptide, is ligated into an expression vector suitable for any convenient host. Both eukaryotic and prokaryotic host systems are used in forming recombinant polypeptides, and a summary of some of the more common systems. The polypeptide is then isolated from lysed cells or from the culture medium and purified to the extent needed for its intended use. Purification is by any technique known in the art, for example, differential extraction, salt fractionation, chromatography, centrifugation, and the like. See, for example, Methods in Enzymology for a variety of methods for purifying proteins.

In addition, shorter protein fragments are produced by chemical synthesis. Alternatively the proteins of the invention is extracted from cells or tissues of humans or non-human animals. Methods for purifying proteins are known in the art, and include the use of detergents or chaotropic agents to disrupt particles followed by differential extraction and separation of the polypeptides by ion exchange chromatography, affinity chromatography, sedimentation according to density, and gel electrophoresis.

Any PAPAP cDNA, including SEQ ID NO: 1, can be used to express PAPAP proteins and polypeptides. The nucleic acid encoding the PAPAP protein or polypeptide to be expressed is operably linked to a promoter in an expression vector using conventional cloning technology. The PAPAP insert in the expression vector may comprise the full coding sequence for the PAPAP protein or a portion thereof. For example, the PAPAP derived insert may encode a polypeptide comprising at least 10 consecutive amino acids of the PAPAP protein of SEQ ID NO: 2.

The expression vector is any of the mammalian, yeast, insect or bacterial expression systems known in the art. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). If desired, to enhance expression and facilitate proper protein folding, the codon context and codon pairing of the sequence is optimized for the particular expression organism in which the expression vector is introduced, as explained by Hatfield, et al., U.S. Pat. No. 5,082,767, the disclosure of which is incorporated by reference herein in its entirety.

In one embodiment, the entire coding sequence of the PAPAP cDNA through the poly A signal of the cDNA is operably linked to a promoter in the expression vector. Alternatively, if the nucleic acid encoding a portion of the PAPAP protein lacks a methionine to serve as the initiation site, an initiating methionine can be introduced next to the first codon of the nucleic acid using conventional techniques. Similarly, if the insert from the PAPAP cDNA lacks a poly A signal, this sequence can be added to the construct by, for example, splicing out the Poly A signal from pSG5 (Stratagene) using BglI and SalI restriction endonuclease enzymes and incorporating it into the mammalian expression vector pXT1 (Stratagene). pXT1 contains the LTRs and a portion of the gag gene from Moloney Murine Leukemia Virus. The position of the LTRs in the construct allows efficient stable transfection. The vector includes the Herpes Simplex Thymidine Kinase promoter and the selectable neomycin gene. The nucleic acid encoding the PAPAP protein or a portion thereof is obtained by PCR from a bacterial vector containing the PAPAP cDNA of SEQ ID NO: 2 using oligonucleotide primers complementary to the PAPAP cDNA or portion thereof and containing restriction endonuclease sequences for Pst I incorporated into the 5' primer and BglII at the 5' end of the corresponding cDNA 3' primer, taking care to ensure that the sequence encoding the PAPAP protein or a portion thereof is positioned properly with respect to the poly A signal. The purified fragment obtained from the resulting PCR reaction is digested with PstI, blunt ended with an exonuclease, digested with BglII, purified and ligated to pXT1, now containing a poly A signal and digested with BglII.

The ligated product is transfected into mouse NIH 3T3 cells using Lipofectin (Life Technologies, Inc., Grand Island, N.Y.) under conditions outlined in the product specification. Positive transfectants are selected after growing the transfected cells in 600 ug/ml G418 (Sigma, St. Louis, Mo.).

The above procedures may also be used to express a mutant PAPAP protein responsible for a detectable phenotype or a portion thereof.

The expressed protein is purified using conventional purification techniques such as ammonium sulfate precipitation or chromatographic separation based on size or charge. The protein encoded by the nucleic acid insert may also be purified using standard immunochromatography techniques. In such procedures, a solution containing the expressed PAPAP protein or portion thereof, such as a cell extract, is applied to a column having antibodies against the PAPAP protein or portion thereof is attached to the chromatography matrix. The expressed protein is allowed to bind the immunochromatography column. Thereafter, the column is washed to remove non-specifically bound proteins. The specifically bound expressed protein is then released from the column and recovered using standard techniques.

To confirm expression of the PAPAP protein or a portion thereof, the proteins expressed from host cells containing an expression vector containing an insert encoding the PAPAP protein or a portion thereof can be compared to the proteins expressed in host cells containing the expression vector without an insert. The presence of a band in samples from cells containing the expression vector with an insert which is absent in samples from cells containing the expression vector without an insert indicates that the PAPAP protein or a portion thereof is being expressed. Generally, the band will have the mobility expected for the PAPAP protein or portion thereof. However, the band may have a mobility different than that expected as a result of modifications such as glycosylation, ubiquitination, or enzymatic cleavage.

Antibodies capable of specifically recognizing the expressed PAPAP protein or a portion thereof are described below.

If antibody production is not possible, the nucleic acids encoding the PAPAP protein or a portion thereof is incorporated into expression vectors designed for use in purification schemes employing chimeric polypeptides. In such strategies the nucleic acid encoding the PAPAP protein or a portion thereof is inserted in frame with the gene encoding the other half of the chimera. The other half of the chimera is □-globin or a nickel binding polypeptide encoding sequence. A chromatography matrix having antibody to □-globin or nickel attached thereto is then used to purify the chimeric protein. Protease cleavage sites is engineered between the □-globin gene or the nickel binding polypeptide and the PAPAP protein or portion thereof. Thus, the two polypeptides of the chimera is separated from one another by protease digestion.

One useful expression vector for generating □-globin chimeric proteins is pSG5 (Stratagene), which encodes rabbit □-globin. Intron II of the rabbit □-globin gene facilitates splicing of the expressed transcript, and the polyadenylation signal incorporated into the construct increases the level of expression. These techniques are well known to those skilled in the art of molecular biology. Standard methods are published in methods texts such as Davis et al., (1986) and many of the methods are available from Stratagene, Life Technologies, Inc., or Promega. Polypeptide may additionally be produced from the construct using in vitro translation systems such as the In vitro Express™ Translation Kit (Stratagene).

Antibodies that Bind PAPAP Polypeptides of the Invention

Any PAPAP polypeptide or whole protein may be used to generate antibodies capable of specifically or selectively binding to an expressed PAPAP protein or fragments thereof as described.

One antibody composition of the invention is capable of specifically binding, or specifically binds, to the PAPAP protein of SEQ ID NO: 2. For an antibody composition to specifically bind to PAPAP, it must demonstrate at least a 5%, 10%, 15%, 20%, 25%, 50%, or 100% greater binding affinity for a full length first variant of the PAPAP protein than for a full length second variant of the PAPAP protein in an ELISA, RIA, or other antibody-based binding assay.

In a preferred embodiment, the invention concerns antibody compositions, either polyclonal or monoclonal, that selectively binds to an epitope-containing a polypeptide comprising a contiguous span of at least 6 amino acids, preferably at least 8 to 10 amino acids, more preferably at least 12, 15, 20, 25, 30, 40, 50, or 100 amino acids of SEQ ID NO: 2.

In other embodiments, the present invention comprises antibody compositions, either polyclonal or monoclonal, that selectively binds to a complex of PAPAP and g34872 polypeptides, wherein said PAPAP polypeptide comprises at least 6 amino acids, preferably at least 8 to 10 amino acids, more preferably at least 12, 15, 20, 25, 30, 40, 50, or 100 amino acids of SEQ ID NO: 2. In a preferred embodiment, said g34872 polypeptide comprises at least 6 amino acids, preferably at least 8 to 10 amino acids of SEQ ID NO: 5. In another embodiment, the present invention provides antibody compositions that selectively binds to a complex of PAPAP and CaM-KII.

An epitope can comprise as few as 3 amino acids in a spatial conformation, which is unique to the epitope. Generally an epitope consists of at least 6 such amino acids, and more often at least 8-10 such amino acids. In preferred embodiment, antigenic epitopes comprise a number of amino acids that is any integer between 3 and 50. Fragments which function as epitopes may be produced by any conventional means. Epitopes can be determined by a Jameson-Wolf antigenic analysis, for example, performed using the computer program PROTEAN, using default parameters (Version 4.0 Windows, DNASTAR, Inc., 1228 South Park Street Madison, Wis.

Predicted antigenic epitopes are shown below. It is pointed out that the immunogenic epitope list describe only amino acid residues comprising epitopes predicted to have the highest degree of immunogenicity by a particular algorithm. Polypeptides of the present invention that are not specifically described as immunogenic are not considered non-antigenic. This is because they may still be antigenic in vivo but merely not recognized as such by the particular algorithm used. Alternatively, the polypeptides are probably antigenic in vitro using methods such a phage display. Thus, listed below are the amino acid residues comprising only preferred epitopes, not a complete list. In fact, all fragments of the polypeptides of the present invention, at least 6 amino acids residues in length, are included in the present invention as being useful as antigenic epitope. Moreover, listed below are only the critical residues of the epitopes determined by the Jameson-Wolf analysis. Thus, additional flanking residues on either the N-terminal, C-terminal, or both N- and C-terminal ends may be added to the sequences listed to generate an epitope-bearing portion at least 6 residues in length. Amino acid residues comprising other immunogenic epitopes may be determined by algorithms similar to the Jameson-Wolf analysis or by in vivo testing for an antigenic response using the methods described herein or those known in the art.

The epitope-bearing fragments of the present invention preferably comprises 6 to 50 amino acids (i.e. any integer between 6 and 50, inclusive) of a polypeptide of the present invention. Also, included in the present invention are antigenic fragments between the integers of 6 and the full length PAPAP sequence.

Preferred PAPAP Immunogenic Enitopes:
Gly 8 to Lys-11
Asp-31 to Asn-33
Gln-40 to Leu-47
Gly-51 to Lys-54
Glu-59 to Arg-62; and
Ser-80 to Thr-83

The invention also concerns a purified or isolated antibody capable of specifically binding to a mutated PAPAP protein or to a fragment or variant thereof comprising an epitope of the mutated PAPAP protein. In another preferred embodiment, the present invention concerns an antibody capable of binding to a polypeptide comprising at least 10 consecutive amino acids of a PAPAP protein and including at least one of the amino acids which can be encoded by the trait causing mutations.

Non-human animals or mammals, whether wild-type or transgenic, which express a different species of PAPAP than the one to which antibody binding is desired, and animals which do not express PAPAP (i.e. a PAPAP knock out animal as described herein) are particularly useful for preparing antibodies. PAPAP knock out animals will recognize all or most of the exposed regions of a PAPAP protein as foreign antigens, and therefore produce antibodies with a wider array of PAPAP epitopes. Moreover, smaller polypeptides with only 10 to 30 amino acids may be useful in obtaining specific binding to any one of the PAPAP proteins. In addition, the humoral immune system of animals which produce a species of PAPAP that resembles the antigenic sequence will preferentially recognize the differences between the animal's native PAPAP species and the antigen sequence, and produce antibodies to these unique sites in the antigen sequence. Such a technique will be particularly useful in obtaining antibodies that specifically bind to any one of the PAPAP proteins.

Antibody preparations prepared according to either protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

The antibodies of the invention may be labeled by any one of the radioactive, fluorescent or enzymatic labels known in the art.

Consequently, the invention is also directed to a method of binding an anti-PAPAP antibody to a PAPAP polypeptide, or of detecting specifically the presence of a PAPAP polypeptide according to the invention in a biological sample, said method comprising the following steps:

a) bringing into contact the biological sample with a polyclonal or monoclonal antibody that specifically binds a PAPAP polypeptide comprising an amino acid sequence of SEQ ID NO: 2, or to a peptide fragment or variant thereof; and b) detecting the antigen-antibody complex formed.

The invention also concerns a diagnostic kit for detecting in vitro the presence of a PAPAP polypeptide according to the present invention in a biological sample, wherein said kit comprises:

a) a polyclonal or monoclonal antibody that specifically binds a PAPAP polypeptide comprising an amino acid sequence of SEQ ID NO: 2, or to a peptide fragment or variant thereof, optionally labeled;

b) a reagent allowing the detection of the antigen-antibody complexes formed, said reagent carrying optionally a label, or being able to be recognized itself by a labeled reagent, more particularly in the case when the above-mentioned monoclonal or polyclonal antibody is not labeled by itself.

The present invention thus relates to antibodies and T-cell antigen receptors (TCR), which specifically bind the polypeptides, and more specifically, the epitopes of the polyepeptides of the present invention, including but not limited to IgG (including IgG1; IgG2, IgG3, and IgG4), IgA (including IgA1 and IgA2), IgD, IgE, or IgM, and IgY. In a preferred embodiment the antibodies are human antigen binding antibody fragments of the present invention include, but are not limited to, Fab, Fab' F(ab)2 and F(ab')2, Fd, single-chain Fvs (scFv), single-chain antibodies, disulfide-linked Fvs (sdFv) and fragments comprising either a $V_L$ or $V_H$ domain. The antibodies may be from any animal origin including birds and mammals. Preferably, the antibodies are human, murine, rabbit, goat, guinea pig, camel, horse, or chicken.

Antigen-binding antibody fragments, including single-chain antibodies, may comprise the variable region(s) alone or in combination with the entire or partial of the following: hinge region, $CH_1$, $CH_2$, and CH3 domains. Also included in the invention are any combinations of variable region(s) and hinge region, $CH_1$, $CH_2$, and CH3 domains. The present invention further includes chimeric, humanized, and human monoclonal and polyclonal antibodies, which specifically bind the polypeptides of the present invention. The present invention further includes antibodies that are anti-idiotypic to the antibodies of the present invention.

The antibodies of the present invention may be monospecific, bispecific, trispecific or have greater multispecificity. Multispecific antibodies may be specific for different epitopes of a polypeptide of the present invention or may be specific for both a polypeptide of the present invention as well as for heterologous compositions, such as a heterologous polypeptide or solid support material. See, e.g., WO 93/17715; WO 92/08802; WO 91/00360; WO 92/05793; Tutt, A. et al. (1991) J. Immunol. 147:60-69; U.S. Pat. Nos. 5,573,920, 4,474,893, 5,601,819, 4,714,681, 4,925,648; Kostelny, S. A. et al. (1992) J. Immunol. 148:1547-1553.

Antibodies of the present invention may be described or specified in terms of the epitope(s) or epitope-bearing portion(s) of a polypeptide of the present invention, which are recognized or specifically bound by the antibody. In the case of proteins of the present invention secreted proteins, the antibodies may specifically bind a full-length protein encoded by a nucleic acid of the present invention, a mature protein (i.e., the protein generated by cleavage of the signal peptide) encoded by a nucleic acid of the present invention, a signal peptide encoded by a nucleic acid of the present invention, or any other polypeptide of the present invention. Therefore, the epitope(s) or epitope bearing polypeptide portion(s) may be specified as described herein, e.g., by N-terminal and C-terminal positions, by size in contiguous amino acid residues, or otherwise described herein (including the sequence listing). Antibodies which specifically bind any epitope or polypeptide of the present invention may also be excluded as individual species. Therefore, the present invention includes antibodies that specifically bind specified polypeptides of the present invention, and allows for the exclusion of the same.

Antibodies of the present invention may also be described or specified in terms of their cross-reactivity. Antibodies that do not specifically bind any other analog, ortholog, or homolog of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies, which only bind polypeptides encoded by polynucleotides, which hybridize to a polynucleotide of the present invention under stringent hybridization conditions (as described herein). Antibodies of the present invention may also be described or specified in terms of their binding affinity. Preferred binding affinities include those with a dissociation constant or Kd less than $5 \times 10^{-6}$M, $10^{-6}$ M, $5 \times 10^{-7}$M, $10^{-7}$M, $5 \times 10^{-8}$M, $10^{-8}$M, $5 \times 10^{-9}$M, $10^{-9}$M, $5 \times 10^{-10}$M, $10^{-10}$M, $5 \times 10^{-11}$M, $10^{-11}$M, $5 \times 10^{1-2}$M, $10^{-12}$M, $5 \times 10^{-13}$M, $10^{-13}$M, $5 \times 10^{-14}$M, $10^{-14}$M, $5 \times 10^{-15}$M, and $10^{-15}$M.

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples. See, e.g., Harlow et al., ANTIBODIES: A LABORATORY MANUAL, (Cold Spring Harbor Laboratory Press, 2nd ed. 1988) (incorporated by reference in the entirety).

The antibodies of the present invention may be used either alone or in combination with other compositions. The antibodies may further be recombinantly fused to a heterologous polypeptide at the N- or C-terminus or chemically conjugated (including covalent and non-covalent conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

The antibodies of the present invention may be prepared by any suitable method known in the art. For example, a polypeptide of the present invention or an antigenic fragment thereof can be administered to an animal in order to induce the production of sera containing polyclonal antibodies. The term "monoclonal antibody" is not limited to antibodies produced through hybridoma technology. The term "antibody" refers to a polypeptide or group of polypeptides which are comprised of at least one binding domain, where a binding domain is formed from the folding of variable domains of an antibody molecule to form three-dimensional binding spaces with an internal surface shape and charge distribution complementary to the features of an antigenic determinant of an antigen., which allows an immunological reaction with the antigen. The term "monoclonal antibody" refers to an antibody that is derived from a single clone, including eukaryotic, prokaryotic, or phage clone, and not the method by which it is produced. Monoclonal antibodies can be prepared using a wide variety of techniques known in the art including the use of hybridoma, recombinant, and phage display technology.

Hybridoma techniques include those known in the art (See, e.g., Harlow et al. (1998); Hammerling, et al. (1981) (said references incorporated by reference in their entireties). Fab and F(ab')2 fragments may be produced, for example, from hybridoma-produced antibodies by proteolytic cleavage, using enzymes such as papain (to produce Fab fragments) or pepsin (to produce F(ab')2 fragments).

Alternatively, antibodies of the present invention can be produced through the application of recombinant DNA technology or through synthetic chemistry using methods known in the art. For example, the antibodies of the present invention can be prepared using various phage display methods known in the art. In phage display methods, functional antibody domains are displayed on the surface of a phage particle, which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman U. et al. (1995); Ames, R. S. et al. (1995); Kettleborough, C. A. et al. (1994); Persic, L. et al. (1997); Burton, D. R. et al. (1994); PCT/GB91/01134; WO 90/02809; WO 91/10737; WO 92/01047; WO 92/18619; WO 93/11236; WO 95/15982; WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743 (said references incorporated by reference in their entireties).

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' F(ab)2 and F(ab')2 fragments can also be employed using methods known in the art such as those disclosed in WO 92/22324; Mullinax, R. L. et al. (1992); and Sawai, H. et al. (1995); and Better, M. et al. (1988) (said references incorporated by reference in their entireties).

Examples of techniques which can be used to produce single-chain Fvs and antibodies include those described in U.S. Pat. Nos. 4,946,778 and 5,258,498; Huston et al. (1991); Shu, L. et al. (1993); and Skerra, A. et al. (1988). For some uses, including in vivo use of antibodies in humans and in vitro detection assays, it may be preferable to use chimeric, humanized, or human antibodies. Methods for producing chimeric antibodies are known in the art. See e.g., Morrison (1985); Oi et al., (1986); Gillies, S. D. et al. (1989); and U.S. Pat. No. 5,807,715. Antibodies can be humanized using a variety of techniques including CDR-grafting (EP 0 239 400; WO 91/09967; U.S. Pat. Nos. 5,530,101; and 5,585,089), veneering or resurfacing (EP 0 592 106; EP 0 519 596; Padlan E. A., (1991); Studnicka G. M. et al. (1994); Roguska M. A. et al. (1994), and chain shuffling (U.S. Pat. No. 5,565,332). Human antibodies can be made by a variety of methods known in the art including phage display methods described above. See also, U.S. Pat. Nos. 4,444,887, 4,716,111, 5,545, 806, and 5,814,318; WO 98/46645; WO 98/50433; WO 98/24893; WO 96/34096; WO 96/33735; and WO 91/10741 (said references incorporated by reference in their entireties).

Further included in the present invention are antibodies recombinantly fused or chemically conjugated (including both covalently and non-covalently conjugations) to a polypeptide of the present invention. The antibodies may be specific for antigens other than polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al. supra and WO 93/21232; EP 0 439 095; Naramura, M. et al. (1994); U.S. Pat. No. 5,474,981; Gillies, S. O. et al. (1992); Fell, H. P. et al. (1991) (said references incorporated by reference in their entireties).

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the hinge region, CH1 domain, CH2 domain, and CH3 domain or any combination of whole domains or portions thereof. The polypeptides of the present invention may be fused or conjugated to the above antibody portions to increase the in vivo half-life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art.

See e.g., U.S. Pat. Nos. 5,336,603, 5,622,929, 5,359,046, 5,349,053, 5,447,851, 5,112,946; EP 0 307 434, EP 0 367 166; WO 96/04388, WO 91/06570; Ashkenazi, A. et al. (1991); Zheng, X. X. et al. (1995); and Vil, H. et al. (1992) (said references incorporated by reference in their entireties).

The invention further relates to antibodies that act as agonists or antagonists of the polypeptides of the present invention. For example, the present invention includes antibodies that disrupt the receptor/ligand interactions with the polypeptides of the invention either partially or fully. Included are both receptor-specific antibodies and ligand-specific antibodies. Included are receptor-specific antibodies, which do not prevent ligand binding but prevent receptor activation. Receptor activation (i.e., signaling) may be determined by techniques described herein or otherwise known in the art. Also included are receptor-specific antibodies which both prevent ligand binding and receptor activation. Likewise, included are neutralizing antibodies that bind the ligand and prevent binding of the ligand to the receptor, as well as antibodies that bind the ligand, thereby preventing receptor activation, but which do not prevent the ligand from binding the receptor. Further included are antibodies that activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097; Deng, B. et al. (1998); Chen, Z. et al. (1998); Harrop, J. A. et al. (1998); Zhu, Z. et al. (1998); Yoon, D. Y. et al. (1998); Prat, M. et al. (1998); Pitard, V. et al. (1997); Liautard, J. et al. (1997); Carlson, N. G. et al. (1997); Taryman, R. E. et al. (1995); Muller, Y. A. et al. (1998); Bartunek, P. et al. (1996) (said references incorporated by reference in their entireties).

As discussed above, antibodies of the polypeptides of the invention can, in turn, be utilized to generate anti-idiotypic antibodies that "mimic" polypeptides of the invention using techniques well known to those skilled in the art. See, e.g. Greenspan and Bona, (1989); Nissinoff, (1991). For example, antibodies which bind to and competitively inhibit polypeptide multimerization or binding of a polypeptide of the invention to ligand can be used to generate anti-idiotypes that "mimic" the polypeptide multimerization or binding domain and, as a consequence, bind to and neutralize polypeptide or its ligand. Such neutralization anti-idiotypic antibodies can be used to bind a polypeptide of the invention or to bind its ligands/receptors, and therby block its biological activity.

Recombinant Vectors

The term "vector" is used herein to designate either a circular or a linear DNA or RNA molecule, which is either double-stranded or single-stranded, and which comprise at least one polynucleotide of interest that is sought to be transferred in a cell host or in a unicellular or multicellular host organism.

The present invention encompasses a family of recombinant vectors that comprise a regulatory polynucleotide derived from the PAPAP genomic sequence, and/or a coding polynucleotide from either the PAPAP genomic sequence or the cDNA sequence.

Generally, a recombinant vector of the invention may comprise any of the polynucleotides described herein, including regulatory sequences, coding sequences and polynucleotide constructs, as well as any PAPAP primer or probe as defined above. More particularly, the recombinant vectors of the present invention can comprise any of the polynucleotides described in the "Genomic Sequences Of The PAPAP Gene" section, the "PAPAP cDNA Sequences" section, the "Coding Regions" section, the "Polynucleotide constructs" section, and the "Oligonucleotide Probes And Primers" section.

In a first preferred embodiment, a recombinant vector of the invention is used to amplify the inserted polynucleotide derived from a PAPAP genomic sequence of SEQ ID NO: 3 or a PAPAP cDNA, for example the cDNA of SEQ ID NO: 1 in a suitable cell host, this polynucleotide being amplified at every time that the recombinant vector replicates.

A second preferred embodiment of the recombinant vectors according to the invention comprises expression vectors comprising either a regulatory polynucleotide or a coding nucleic acid of the invention, or both. Within certain embodiments, expression vectors are employed to express the PAPAP polypeptide which can be then purified and, for example be used in ligand screening assays or as an immunogen in order to raise specific antibodies directed against the PAPAP protein. In other embodiments, the expression vectors are used for constructing transgenic animals and also for gene therapy. Expression requires that appropriate signals are provided in the vectors, said signals including various regulatory elements, such as enhancers/promoters from both viral and mammalian sources that drive expression of the genes of interest in host cells. Dominant drug selection markers for establishing permanent, stable cell clones expressing the products are generally included in the expression vectors of the invention, as they are elements that link expression of the drug selection markers to expression of the polypeptide.

More particularly, the present invention relates to expression vectors which include nucleic acids encoding a PAPAP protein, preferably the PAPAP protein of the amino acid sequence of SEQ ID NO: 2 or variants or fragments thereof.

The invention also provides recombinant vectors, and methods of using the vectors, whose presence in a cell causes an increase in PAPAP gene expression. For example, a vector may comprise sequences from the 5' regulatory region of PAPAP as well as heterologous promoter or enhancer sequences, so that the presence of the vector in a cell causes the introduction of the heterologous promoter or enhancer sequence by homologous recombination into the 5' regulatory region of PAPAP. In this way, PAPAP can be placed under the control of regulatory elements that control its expression in any desirable way, e.g. constitutively, in a tissue specific way, or inducibly by one or more endogenous or exogenous factors.

The invention also pertains to a recombinant expression vector useful for the expression of the PAPAP coding sequence, wherein said vector comprises a nucleic acid of SEQ ID NO: 1.

Some of the elements which can be found in the vectors of the present invention are described in further detail in the following sections.

1. General Features of the Expression Vectors of the Invention

A recombinant vector according to the invention comprises, but is not limited to, a YAC (Yeast Artificial Chromosome), a BAC (Bacterial Artificial Chromosome), a phage, a phagemid, a cosmid, a plasmid or even a linear DNA molecule which may comprise a chromosomal, non-chromosomal, semi-synthetic and synthetic DNA. Such a recombinant vector can comprise a transcriptional unit comprising an assembly of:

(1) a genetic element or elements having a regulatory role in gene expression, for example promoters or enhancers.

Enhancers are cis-acting elements of DNA, usually from about 10 to 300 bp in length that act on the promoter to increase the transcription.

(2) a structural or coding sequence which is transcribed into mRNA and eventually translated into a polypeptide, said structural or coding sequence being operably linked to the regulatory elements described in (1); and (3) appropriate transcription initiation and termination sequences. Structural units intended for use in yeast or eukaryotic expression systems preferably include a leader sequence enabling extracellular secretion of translated protein by a host cell. Alternatively, when a recombinant protein is expressed without a leader or transport sequence, it may include a N-terminal residue. This residue may or may not be subsequently cleaved from the expressed recombinant protein to provide a final product.

Generally, recombinant expression vectors will include origins of replication, selectable markers permitting transformation of the host cell, and a promoter derived from a highly expressed gene to direct transcription of a downstream structural sequence. The heterologous structural sequence is assembled in appropriate phase with translation initiation and termination sequences, and preferably a leader sequence capable of directing secretion of the translated protein into the periplasmic space or the extracellular medium. In a specific embodiment wherein the vector is adapted for transfecting and expressing desired sequences in mammalian host cells, preferred vectors will comprise an origin of replication in the desired host, a suitable promoter and enhancer, and also any necessary ribosome binding sites, polyadenylation signal, splice donor and acceptor sites, transcriptional termination sequences, and 5'-flanking non-transcribed sequences. DNA sequences derived from the SV40 viral genome, for example SV40 origin, early promoter, enhancer, splice and polyadenylation signals may be used to provide the required non-transcribed genetic elements.

The in vivo expression of a PAPAP polypeptide of SEQ ID NO: 2 or fragments or variants thereof may be useful in order to correct a genetic defect related to the expression of the native gene in a host organism or to the production of a biologically inactive PAPAP protein.

Consequently, the present invention also comprises recombinant expression vectors mainly designed for the in vivo production of the PAPAP polypeptide of SEQ ID NO: 2 or fragments or variants thereof by the introduction of the appropriate genetic material in the organism of the patient to be treated. This genetic material may be introduced in vitro in a cell that has been previously extracted from the organism, the modified cell being subsequently reintroduced in the said organism, directly in vivo into the appropriate tissue.

2. Regulatory Elements

Promoters

The suitable promoter regions used in the expression vectors according to the present invention are chosen taking into account the cell host in which the heterologous gene has to be expressed. The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell, such as, for example, a human or a viral promoter.

A suitable promoter may be heterologous with respect to the nucleic acid for which it controls the expression or alternatively can be endogenous to the native polynucleotide containing the coding sequence to be expressed. Additionally, the promoter is generally heterologous with respect to the recombinant vector sequences within which the construct promoter/coding sequence has been inserted.

Promoter regions can be selected from any desired gene using, for example, CAT (chloramphenicol transferase) vectors and more preferably pKK232-8 and pCM7 vectors.

Preferred bacterial promoters are the LacI, LacZ, the T3 or T7 bacteriophage RNA polymerase promoters, the gpt, lambda PR, PL and trp promoters (EP 0036776), the polyhedrin promoter, or the p10 protein promoter from baculovirus (Kit Novagen) (Smith et al., 1983; O'Reilly et al., 1992), the lambda PR promoter or also the trc promoter.

Eukaryotic promoters include CMV immediate early, HSV thymidine kinase, early and late SV40, LTRs from retrovirus, and mouse metallothionein-L. Selection of a convenient vector and promoter is well within the level of ordinary skill in the art.

The choice of a promoter is well within the ability of a person skilled in the field of genetic egineering. For example, one may refer to Sambrook et al. (1989) or Fuller et al. (1996).

Other Regulatory Elements

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

3. Selectable Markers

Such markers would confer an identifiable change to the cell permitting easy identification of cells containing the expression construct. The selectable marker genes for selection of transformed host cells are preferably dihydrofolate reductase or neomycin resistance for eukaryotic cell culture, TRP1 for *S. cerevisiae* or tetracycline, rifampicin or ampicillin resistance in *E. coli*, or levan saccharase for mycobacteria, this latter marker being a negative selection marker.

4. Preferred Vectors

Bacterial Vectors

As a representative but non-limiting example, useful expression vectors for bacterial use can comprise a selectable marker and a bacterial origin of replication derived from commercially available plasmids comprising genetic elements of pBR322 (ATCC 37017). Such commercial vectors include, for example, pKK223-3 (Pharmacia, Uppsala, Sweden), and GEMI (Promega Biotec, Madison, Wis., USA).

Large numbers of other suitable vectors are known to those of skill in the art, and commercially available, such as the following bacterial vectors: pQE70, pQE60, pQE-9 (Qiagen), pbs, pD10, phagescript, psiX174, pbluescript SK, pbsks, pNH8A, pNH16A, pNH18A, pNH46A (Stratagene); ptrc99a, pKK223-3, pKK233-3, pDR540, pRIT5 (Pharmacia); pWLNEO, pSV2CAT, pOG44, pXT1, pSG (Stratagene); pSVK3, pBPV, pMSG, pSVL (Pharmacia); pQE-30 (QIAexpress).

Bacteriophage Vectors

The P1 bacteriophage vector may contain large inserts ranging from about 80 to about 100 kb.

The construction of P1 bacteriophage vectors such as p158 or p158/neo8 are notably described by Sternberg (1992, 1994). Recombinant P1 clones comprising PAPAP nucleotide sequences may be designed for inserting large polynucleotides of more than 40 kb (Linton et al., 1993). To generate P1 DNA for transgenic experiments, a preferred protocol is the protocol described by McCormick et al. (1994). Briefly, *E. coli* (preferably strain NS3529) harboring the P1 plasmid are grown overnight in a suitable broth medium containing 25 µg/ml of kanamycin. The P1 DNA is prepared from the *E. coli* by alkaline lysis using the Qiagen Plasmid Maxi kit (Qiagen, Chatsworth, Calif., USA), according to the manufacturer's instructions. The P1 DNA is purified from the bacterial lysate on two Qiagen-tip 500 columns, using the washing and elution buffers contained in the kit. A phenol/chloroform extraction is then performed before precipitating the DNA with 70% ethanol. After solubilizing the DNA in TE (10 mM Tris-HCl, pH 7.4, 1 mM EDTA), the concentration of the DNA is assessed by spectrophotometry.

When the goal is to express a P1 clone comprising PAPAP nucleotide sequences in a transgenic animal, typically in transgenic mice, it is desirable to remove vector sequences from the P1 DNA fragment, for example by cleaving the P1 DNA at rare-cutting sites within the P1 polylinker (SfiI, NotI or SalI). The P1 insert is then purified from vector sequences on a pulsed-field agarose gel, using methods similar using methods similar to those originally reported for the isolation of DNA from YACs (Schedl et al., 1993a; Peterson et al., 1993). At this stage, the resulting purified insert DNA can be concentrated, if necessary, on a Millipore Ultrafree-MC Filter Unit (Millipore, Bedford, Mass., USA—30,000 molecular weight limit) and then dialyzed against microinjection buffer (10 mM Tris-HCl, pH 7.4; 250 µM EDTA) containing 100 mM NaCl, 30 µM spermine, 70 µM spermidine on a microdyalisis membrane (type VS, 0.025 µM from Millipore). The intactness of the purified P1 DNA insert is assessed by electrophoresis on 1% agarose (Sea Kem GTG; FMC Bio-products) pulse-field gel and staining with ethidium bromide.

Baculovirus Vectors

A suitable vector for the expression of the PAPAP polypeptide of SEQ ID NO: 2 or fragments or variants thereof is a baculovirus vector that can be propagated in insect cells and in insect cell lines. A specific suitable host vector system is the pVL1392/1393 baculovirus transfer vector (Pharmingen) that is used to transfect the SF9 cell line (ATCC No. CRL 1711) which is derived from *Spodoptera frugiperda*.

Other suitable vectors for the expression of the PAPAP polypeptide of SEQ ID NO: 2 or fragments or variants thereof in a baculovirus expression system include those described by Chai et al. (1993), Vlasak et al. (1983) and Lenhard et al. (1996).

Viral Vectors

In one specific embodiment, the vector is derived from an adenovirus. Preferred adenovirus vectors according to the invention are those described by Feldman and Steg (1996) or Ohno et al. (1994). Another preferred recombinant adenovirus according to this specific embodiment of the present invention is the human adenovirus type 2 or 5 (Ad 2 or Ad 5) or an adenovirus of animal origin (French patent application No. FR-93.05954).

Retrovirus vectors and adeno-associated virus vectors are generally understood to be the recombinant gene delivery systems of choice for the transfer of exogenous polynucleotides in vivo, particularly to mammals, including humans. These vectors provide efficient delivery of genes into cells, and the transferred nucleic acids are stably integrated into the chromosomal DNA of the host.

Particularly preferred retroviruses for the preparation or construction of retroviral in vitro or in vitro gene delivery vehicles of the present invention include retroviruses selected from the group consisting of Mink-Cell Focus Inducing Virus, Murine Sarcoma Virus, Reticuloendotheliosis virus and Rous Sarcoma virus. Particularly preferred Murine Leukemia Viruses include the 4070A and the 1504A viruses, Abelson (ATCC No VR-999), Friend (ATCC No VR-245), Gross (ATCC No VR-590), Rauscher (ATCC No VR-998) and Moloney Murine Leukemia Virus (ATCC No VR-190; PCT Application No WO 94/24298). Particularly preferred Rous Sarcoma Viruses include Bryan high titer (ATCC Nos VR-334, VR-657, VR-726, VR-659 and VR-728). Other preferred retroviral vectors are those described in Roth et al. (1996), PCT Application No WO 93/25234, PCT Application No WO 94/06920, Roux et al., 1989, Julan et al., 1992 and Neda et al., 1991.

Yet another viral vector system that is contemplated by the invention comprises the adeno-associated virus (AAV). The adeno-associated virus is a naturally occurring defective virus that requires another virus, such as an adenovirus or a herpes virus, as a helper virus for efficient replication and a productive life cycle (Muzyczka et al., 1992). It is also one of the few viruses that may integrate its DNA into non-dividing cells, and exhibits a high frequency of stable integration (Flotte et al., 1992; Samulski et al., 1989; McLaughlin et al., 1989). One advantageous feature of AAV derives from its reduced efficacy for transducing primary cells relative to transformed cells.

BAC Vectors

The bacterial artificial chromosome (BAC) cloning system (Shizuya et al., 1992) has been developed to stably maintain large fragments of genomic DNA (100-300 kb) in *E. coli*. A preferred BAC vector comprises a pBeloBAC 11 vector that has been described by Kim et al. (1996). BAC libraries are prepared with this vector using size-selected genomic DNA that has been partially digested using enzymes that permit ligation into either the Bam HI or HindIII sites in the vector. Flanking these cloning sites are T7 and SP6 RNA polymerase transcription initiation sites that can be used to generate end probes by either RNA transcription or PCR methods. After the construction of a BAC library in *E. coli*, BAC DNA is purified from the host cell as a supercoiled circle. Converting these circular molecules into a linear form precedes both size determination and introduction of the BACs into recipient cells. The cloning site is flanked by two Not I sites, permitting cloned segments to be excised from the vector by Not I digestion. Alternatively, the DNA insert contained in the pBeloBAC11 vector may be linearized by treatment of the BAC vector with the commercially available enzyme lambda terminase that leads to the cleavage at the unique cosN site, but this cleavage method results in a full length BAC clone containing both the insert DNA and the BAC sequences.

5. Delivery of the Recombinant Vectors

In order to effect expression of the polynucleotides and polynucleotide constructs of the invention, these constructs must be delivered into a cell. This delivery may be accomplished in vitro, as in laboratory procedures for transforming cell lines, or in vivo or ex vivo, as in the treatment of certain diseases states.

One mechanism is viral infection where the expression construct is encapsulated in an infectious viral particle.

Several non-viral methods for the transfer of polynucleotides into cultured mammalian cells are also contemplated by the present invention, and include, without being limited to, calcium phosphate precipitation (Graham et al., 1973; Chen et al., 1987), DEAE-dextran (Gopal, 1985), electroporation (Tur-Kaspa et al., 1986; Potter et al., 1984), direct microinjection (Harland et al., 1985), DNA-loaded liposomes (Nicolau et al., 1982; Fraley et al., 1979), and receptor-mediated transfection (Wu and Wu, 1987; 1988). Some of these techniques may be successfully adapted for in vivo or ex vivo use.

Once the expression polynucleotide has been delivered into the cell, it may be stably integrated into the genome of the recipient cell. This integration may be in the cognate location and orientation via homologous recombination (gene replacement) or it may be integrated in a random, non specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle.

One specific embodiment for a method for delivering a protein or peptide to the interior of a cell of a vertebrate in vivo comprises the step of introducing a preparation comprising a physiologically acceptable carrier and a naked polynucleotide operatively coding for the polypeptide of interest into the interstitial space of a tissue comprising the cell, whereby the naked polynucleotide is taken up into the interior of the cell and has a physiological effect. This is particularly applicable for transfer in vitro but it may be applied to in vivo as well.

Compositions for use in vitro and in vivo comprising a "naked" polynucleotide are described in PCT application No. WO 90/11092 (Vical Inc.) and also in PCT application No. WO 95/11307 (Institut Pasteur, INSERM, Université d'Ottawa) as well as in the articles of Tacson et al. (1996) and of Huygen et al. (1996).

In still another embodiment of the invention, the transfer of a naked polynucleotide of the invention, including a polynucleotide construct of the invention, into cells may be proceeded with a particle bombardment (biolistic), said particles being DNA-coated microprojectiles accelerated to a high velocity allowing them to pierce cell membranes and enter cells without killing them, such as described by Klein et al. (1987).

In a further embodiment, the polynucleotide of the invention may be entrapped in a liposome (Ghosh and Bacchawat, 1991; Wong et al., 1980; Nicolau et al., 1987).

In a specific embodiment, the invention provides a composition for the in vivo production of the PAPAP protein or polypeptide described herein. It comprises a naked polynucleotide operatively coding for this polypeptide, in solution in a physiologically acceptable carrier, and suitable for introduction into a tissue to cause cells of the tissue to express the said protein or polypeptide.

The amount of vector to be injected to the desired host organism varies according to the site of injection. As an indicative dose, it will be injected between 0.1 and 100 µg of the vector in an animal body, preferably a mammal body, for example a mouse body.

In another embodiment of the vector according to the invention, it may be introduced in vitro in a host cell, preferably in a host cell previously harvested from the animal to be treated and more preferably a somatic cell such as a muscle cell. In a subsequent step, the cell that has been transformed with the vector coding for the desired PAPAP polypeptide or the desired fragment thereof is reintroduced into the animal body in order to deliver the recombinant protein within the body either locally or systemically.

Cell Hosts

Another object of the invention comprises a host cell that has been transformed or transfected with one of the polynucleotides described herein, and in particular a polynucleotide either comprising a PAPAP regulatory polynucleotide or the coding sequence of the PAPAP polypeptide of SEQ ID NOs: 1 or 3, or a fragment or a variant thereof. Also included are host cells that are transformed (prokaryotic cells) or that are transfected (eukaryotic cells) with a recombinant vector such as one of those described above. More particularly, the cell hosts of the present invention can comprise any of the polynucleotides described in the "Genomic Sequences Of the PAPAP Gene" section, the "PAPAP cDNA Sequences" section, the "Coding Regions" section, the "Polynucleotide constructs" section, and the "Oligonucleotide Probes And Primers" section.

An additional recombinant cell host according to the invention comprises any of the vectors described herein, more particularly any of the vectors described in the "Recombinant Vectors" section.

Preferred host cells used as recipients for the expression vectors of the invention are the following:

a) Prokaryotic host cells: *Escherichia coli* strains (I.E.DH5-α: strain), *Bacillus subtilis, Salmonella typhimurium*, and strains from species like *Pseudomonas, Streptomyces* and *Staphylococcus*.

b) Eukaryotic host cells: HeLa cells (ATCC No. CCL2; No. CCL2.1; No. CCL2.2), Cv 1 cells (ATCC No. CCL70), COS cells (ATCC No. CRL1650; No. CRL 1651), Sf-9 cells (ATCC No. CRL1711), C127 cells (ATCC No. CRL-1804), 3T3 (ATCC No. CRL-6361), CHO (ATCC No. CCL-61), human kidney 293. (ATCC No. 45504; No. CRL-1573) and BHK (ECACC No. 84100501; No. 84111301).

c) Other Mammalian Host Cells.

The PAPAP gene expression in mammalian, and typically human, cells may be rendered defective, or alternatively it may be proceeded with the insertion of a PAPAP genomic or cDNA sequence with the replacement of the PAPAP gene counterpart in the genome of an animal cell by a PAPAP polynucleotide according to the invention. These genetic alterations may be generated by homologous recombination events using specific DNA constructs that have been previously described.

One kind of cell host that may be used is mammal zygotes, such as murine zygotes. For example, murine zygotes may undergo microinjection with a purified DNA molecule of interest, for example a purified DNA molecule that has previously been adjusted to a concentration range from 1 ng/ml—for BAC inserts-3 ng/µl—for P1 bacteriophage inserts—in 10 mM Tris-HCl, pH 7.4, 250 µM EDTA containing 100 mM NaCl, 30 µM spermine, and 70 µM spermidine. When the DNA to be microinjected has a large size, polyamines and high salt concentrations can be used in order to avoid mechanical breakage of this DNA, as described by Schedl et al (1993b).

Anyone of the polynucleotides of the invention, including the DNA constructs described herein, may be introduced in an embryonic stem (ES) cell line, preferably a mouse ES cell line. ES cell lines are derived from pluripotent, uncommitted cells of the inner cell mass of pre-implantation blastocysts. Preferred ES cell lines are the following: ES-E14TG2a (ATCC No. CRL-1821), ES-D3 (ATCC No. CRL1934 and No. CRL-11632), YS001 (ATCC No. CRL-11776), 36.5 (ATCC No. CRL-11116). To maintain ES cells in an uncommitted state, they are cultured in the presence of growth inhibited feeder cells which provide the appropriate signals to preserve this embryonic phenotype and serve as a matrix for ES cell adherence. Preferred feeder cells are primary embryonic fibroblasts that are established from tissue of day 13-day 14 embryos of virtually any mouse strain, that are maintained in culture, such as described by Abbondanzo et al. (1993) and are inhibited in growth by irradiation, such as described by Robertson (1987), or by the presence of an inhibitory concentration of LIF, such as described by Pease and Williams (1990).

The constructs in the host cells can be used in a conventional manner to produce the gene product encoded by the recombinant sequence.

Following transformation of a suitable host and growth of the host to an appropriate cell density, the selected promoter is induced by appropriate means, such as temperature shift or chemical induction, and cells are cultivated for an additional period.

Cells are typically harvested by centrifugation, disrupted by physical or chemical means, and the resulting crude extract retained for further purification.

Microbial cells employed in the expression of proteins can be disrupted by any convenient method, including freeze-thaw cycling, sonication, mechanical disruption, or use of cell lysing agents. Such methods are well known by the skill artisan.

PAPAP Gene Activation

The present invention also encompasses primary, secondary, and immortalized homologously recombinant host cells of vertebrate origin, preferably mammalian origin and particularly human origin, that have been engineered to: a) insert exogenous (heterologous) polynucleotides into the endogenous chromosomal DNA of a targeted gene, b) delete endogenous chromosomal DNA, and/or c) replace endogenous chromosomal DNA with exogenous polynucleotides. Insertions, deletions, and/or replacements of polynucleotide sequences may be to the coding sequences of the targeted gene and/or to regulatory regions, such as promoter and enhancer sequences, operably associated with the targeted gene.

The present invention further relates to a method of making a homologously recombinant host cell in vitro or in vivo, wherein the expression of a targeted gene not normally expressed in the cell is altered. Preferably the alteration causes expression of the targeted gene under normal growth conditions or under conditions suitable for producing the polypeptide encoded by the targeted gene. The method comprises the steps of: (a) transfecting the cell in vitro or in vivo with a polynucleotide construct, the polynucleotide construct comprising; (i) a targeting sequence; (ii) a regulatory sequence and/or a coding sequence; and (iii) an unpaired splice donor site, if necessary, thereby producing a transfected cell; and (b) maintaining the transfected cell in vitro or in vivo under conditions appropriate for homologous recombination.

The present invention further relates to a method of altering the expression of a targeted gene in a cell in vitro or in vivo wherein the gene is not normally expressed in the cell, comprising the steps of: (a) transfecting the cell in vitro or in vivo with a a polynucleotide construct, the a polynucleotide construct comprising: (i) a targeting sequence; (ii) a regulatory sequence and/or a coding sequence; and (iii) an unpaired splice donor site, if necessary, thereby producing a transfected cell; and (b) maintaining the transfected cell in vitro or in vivo under conditions appropriate for homologous recombination, thereby producing a homologously recombinant cell; and (c) maintaining the homologously recombinant cell in vitro or in vivo under conditions appropriate for expression of the gene.

The present invention further relates to a method of making a polypeptide of the present invention by altering the expression of a targeted endogenous gene in a cell in vitro or in vivo wherein the gene is not normally expressed in the cell, comprising the steps of: a) transfecting the cell in vitro with a a polynucleotide construct, the a polynucleotide construct comprising: (i) a targeting sequence; (ii) a regulatory sequence and/or a coding sequence; and (iii) an unpaired splice donor site, if necessary, thereby producing a transfected cell; (b) maintaining the transfected cell in vitro or in vivo under conditions appropriate for homologous recombination, thereby producing a homologously recombinant cell; and c) maintaining the homologously recombinant cell in vitro or in vivo under conditions appropriate for expression of the gene thereby making the polypeptide.

The present invention further relates to a polynucleotide construct which alters the expression of a targeted gene in a cell type in which the gene is not normally expressed. This occurs when the polynucleotide construct is inserted into the chromosomal DNA of the target cell, wherein the polynucleotide construct comprises: a) a targeting sequence; b) a regulatory sequence and/or coding sequence; and c) an unpaired splice-donor site, if necessary. Further included are polynucleotide constructs, as described above, wherein the construct further comprises a polynucleotide that encodes a polypeptide and which is in-frame with the targeted endogenous gene after homologous recombination with chromosomal DNA.

The compositions may be produced, and methods performed, by techniques known in the art, such as those described in U.S. Pat. Nos. 6,054,288; 6,048,729; 6,048,724; 6,048,524; 5,994,127; 5,968,502; 5,965,125; 5,869,239; 5,817,789; 5,783,385; 5,733,761; 5,641,670; 5,580,734; International Publication Nos: WO96/29411, WO 94/12650; and scientific articles including 1994; Koller et al., Proc. Natl. Acad. Sci. USA 86:8932-8935 (1989) (the disclosures of each of which are incorporated by reference in their entireties).

Transgenic Animals

The terms "transgenic animals" or "host animals" are used herein designate animals that have their genome genetically and artificially manipulated so as to include one of the nucleic acids according to the invention. Preferred animals are non-human mammals and include those belonging to a genus selected from *Mus* (e.g. mice), *Rattus* (e.g. rats) and *Oryctogalus* (e.g. rabbits) which have their genome artificially and genetically altered by the insertion of a nucleic acid according to the invention. In one embodiment, the invention encompasses non-human host mammals and animals comprising a recombinant vector of the invention or a PAPAP gene disrupted by homologous recombination with a knock out vector.

The transgenic animals of the invention all include within a plurality of their cells a cloned recombinant or synthetic DNA sequence, more specifically one of the purified or isolated nucleic acids comprising a PAPAP coding sequence, a PAPAP regulatory polynucleotide, a polynucleotide construct, or a DNA sequence encoding an antisense polynucleotide such as described in the present specification.

Generally, a transgenic animal according the present invention comprises any one of the polynucleotides, the recombinant vectors and the cell hosts described in the present invention. More particularly, the transgenic animals of the present invention can comprise any of the polynucleotides described in the "Genomic Sequences of the PAPAP Gene" section, the "PAPAP cDNA Sequences" section, the "Coding Regions" section, the "Polynucleotide constructs" section, the "Oligonucleotide Probes and Primers" section, the "Recombinant Vectors" section and the "Cell Hosts" section.

In a first preferred embodiment, these transgenic animals may be good experimental models in order to study biological processes and disorders such as learning, memory, the cell cycle, schizophrenia, bipolar disorder, or any other CaM-KII-related activity, as well as the diverse pathologies related to cell differentiation, in particular concerning the transgenic animals within the genome of which has been inserted one or several copies of a polynucleotide encoding a native PAPAP protein, or alternatively a mutant PAPAP protein.

In a second preferred embodiment, these transgenic animals may express a desired polypeptide of interest under the control of the regulatory polynucleotides of the PAPAP gene, leading to good yields in the synthesis of this protein of interest, and eventually a tissue specific expression of this protein of interest.

The design of the transgenic animals of the invention may be made according to the conventional techniques well known from the one skilled in the art. For more details regarding the production of transgenic animals, and specifically transgenic mice, it may be referred to U.S. Pat. Nos. 4,873,191, issued Oct. 10, 1989; 5,464,764 issued Nov. 7, 1995; and 5,789,215, issued Aug. 4, 1998; these documents being herein incorporated by reference to disclose methods producing transgenic mice.

Transgenic animals of the present invention are produced by the application of procedures which result in an animal with a genome that has incorporated exogenous genetic material. The procedure involves obtaining the genetic material, or a portion thereof, which encodes either a PAPAP coding sequence, a PAPAP regulatory polynucleotide or a DNA sequence encoding a PAPAP antisense polynucleotide such as described in the present specification.

A recombinant polynucleotide of the invention is inserted into an embryonic or ES stem cell line. The insertion is preferably made using electroporation, such as described by Thomas et al. (1987). The cells subjected to electroporation are screened (e.g. by selection via selectable markers, by PCR or by Southern blot analysis) to find positive cells which have integrated the exogenous recombinant polynucleotide into their genome, preferably via an homologous recombination event. An illustrative positive-negative selection procedure that may be used according to the invention is described by Mansour et al. (1988).

Then, the positive cells are isolated, cloned and injected into 3.5 days old blastocysts from mice, such as described by Bradley (1987). The blastocysts are then inserted into a female host animal and allowed to grow to term.

Alternatively, the positive ES cells are brought into contact with embryos at the 2.5 days old 8-16 cell stage (morulae) such as described by Wood et al. (1993) or by Nagy et al. (1993), the ES cells being internalized to colonize extensively the blastocyst including the cells which will give rise to the germ line.

The offspring of the female host are tested to determine which animals are transgenic e.g. include the inserted exogenous DNA sequence and which are wild-type.

Thus, the present invention also concerns a transgenic animal containing a nucleic acid, a recombinant expression vector or a recombinant host cell according to the invention.

Recombinant Cell Lines Derived from the Transgenic Animals of the Invention.

A further object of the invention comprises recombinant host cells obtained from a transgenic animal described herein. In one embodiment the invention encompasses cells derived from non-human host mammals and animals comprising a recombinant vector of the invention or a PAPAP gene disrupted by homologous recombination with a knock out vector.

Recombinant cell lines may be established in vitro from cells obtained from any tissue of a transgenic animal according to the invention, for example by transfection of primary cell cultures with vectors expressing one-genes such as SV40 large T antigen, as described by Chou (1989) and Shay et al. (1991).

Assays for Identification of Compounds for Treatment of Schizophrenia and Bipolar Disorder The present invention provides assays which may be used to test compounds for their ability to treat CNS disorders, and in particular, to ameliorate symptoms of a CNS disorder mediated by PAPAP. In preferred embodiments, compounds are tested for their ability to ameliorate symptoms of schizophrenia or bipolar disorder mediated by PAPAP. Compounds may also be tested for their ability to treat related disorders, including among others psychotic disorders, mood disorders, autism, substance dependence and alcoholism, mental retardation, and other psychiatric diseases including cognitive, anxiety, eating, impulse-control, memory, learning, and personality disorders, as defined with the Diagnosis and Statistical Manual of Mental Disorders fourth edition (DSM-IV) classification.

The present invention also provides cell and animal, including primate and rodent, models of schizophrenia, bipolar disorder, learning, cognitive, memory, and related disorders.

In one aspect, provided are non-cell based, cell based and animal based assays for the identification of such compounds that affect PAPAP activity. PAPAP activity may be affected by any mechanism; in certain embodiments, PAPAP activity is affected by modulating the level of PAPAP gene expression or the activity of the PAPAP gene product.

In one aspect, provided are non-cell based, cell based and animal based assays for the identification of such compounds that affect g34872 activity. G34872 activity may be affected by modulating the level of PAPAP gene expression or the activity of the PAPAP gene product. Preferably, assays for the identification of such compounds that affect g34872 activity are capable of detecting the interaction of PAPAP and g34872 polypeptides, or are capable of detecting the interaction of PAPAP and CaM-KII kinases.

The present methods allow the identification of compounds that affect PAPAP or g34872 activity directly or indirectly. The non-cell based, cell based and animal assays of the present invention may be used to identify compounds that act on an element of a PAPAP pathway other than PAPAP itself. These compounds can then be used as a therapeutic treatment to modulate PAPAP and other gene products involved in schizophrenia, bipolar disorder and related disorders.

Cell and Non-Cell Based Assays

In one aspect, cell based assays using recombinant or non-recombinant cells may be used to identify compounds which modulate PAPAP activity.

In one aspect, a cell based assay of the invention encompasses a method for identifying a test compound for the treatment of schizophrenia, bipolar disorder or related CNS disorder comprising (a) exposing a cell to a test compound at a concentration and time sufficient to ameliorate an endpoint related to schizophrenia, bipolar disorder or related CNS disorder, and (b) determining the level of PAPAP activity or PAPAP-g34872 interaction or complexes in a cell. PAPAP activity can be measured, for example, by assaying a cell for mRNA transcript level, PAPAP peptide expression, localization or protein activity. Protein activity can be measured in any of a large number of ways, such as by examining g34872 activity, CaM-KII activity, glutamate or NMDA receptor or associated neuronal activity activity, cell cycle progression, cell cycle regulated myosin-V activity, centrosome duplication, or any other activity associated with g34872 or with CaM-KII proteins. Examples of assays that may be used to assess such activities include Bayer et al. (2001) Nature 411: 801-5; Chang et al. (1998) PNAS 95:10890-5; Chang et al. (2001) Neuroscience 102:767-77; Chum et al. (2000) PNAS 97:5604-5609; Liu et al. (1996) PNAS 93:7332-7336; Karcher et al. (2001) Science 293:1317-1320; and Griffith et al. (1994) PNAS 91:10044-10048; the disclosures of each of which is incorporated herein in their entireties. Preferably the test compound is a compound capable of or suspected to be capable of ameliorating a symptom of schizophrenia, bipolar disorder or a related disorder. Test compounds capable of modulating PAPAP activity may be selected for use in developing medicaments. Such cell based assays are further described herein in the section titled "Method For Screening Ligands That Modulate The Expression Of The PAPAP Gene."

In another aspect, a cell based assay of the invention encompasses a method for identifying a compound for the treatment of schizophrenia or bipolar disorder comprising (a) exposing a cell to a level of PAPAP activity sufficient to cause a schizophrenia-related or bipolar disorder-related endpoint, and (b) exposing said cell to a test compound. A test compound can then be selected according to its ability to ameliorate said schizophrenia-related or bipolar disorder-related endpoints. PAPAP activity may be provided by any suitable method, including but not limited to providing a vector containing a PAPAP nucleotide sequence, treating said cell with a compound capable of increasing PAPAP expression and treating said cell with a PAPAP peptide. Preferably the test compound is a compound capable of or suspected to be capable of ameliorating a symptom of schizophrenia, bipolar disorder or a related disorder; alternatively, the test compound is suspected of exacerbating an endpoint schizophrenia, bipolar disorder or a related disorder. A test compound capable of ameliorating any detectable symptom or endpoint of a schizophrenia, bipolar disorder or a related disorder may be selected for use in developing medicaments. Suitable cell lines can be determined by the person skilled in the art; preferably a cell line or neuronal origin is used.

In another embodiment, the invention provides cell and non-cell based assays to PAPAP to determine whether PAPAP peptides bind to the cell surface, and to identify compounds for the treatment of schizophrenia, bipolar disorder and related disorders that interact with a PAPAP receptor. In one such embodiment, a PAPAP polynucleotide, or fragments thereof, is cloned into expression vectors such as those described herein. The proteins are purified by size, charge, immunochromatography or other techniques familiar to those skilled in the art. Following purification, the proteins are labeled using techniques known to those skilled in the art. The labeled proteins are incubated with cells or cell lines derived from a variety of organs or tissues to allow the proteins to bind to any receptor present on the cell surface. Following the incubation, the cells are washed to remove non-specifically bound protein. The labeled proteins are detected by autoradiography. Alternatively, unlabeled proteins may be incubated with the cells and detected with antibodies having a detectable label, such as a fluorescent molecule, attached thereto. Specificity of cell surface binding may be analyzed by conducting a competition analysis in which various amounts of unlabeled protein are incubated along with the labeled protein. The amount of labeled protein bound to the cell surface decreases as the amount of competitive unlabeled protein increases. As a control, various amounts of an unlabeled protein unrelated to the labeled protein is included in some binding reactions. The amount of labeled protein bound to the cell surface does not decrease in binding reactions containing increasing amounts of unrelated unlabeled protein, indicating that the protein encoded by the nucleic acid binds specifically to the cell surface. One example of such an assay has been demonstrated in Example 1, below. In one aspect, PAPAP binding may be used to detect and localize a g34872 or CaM-KII polypeptide.

In another embodiment, the present invention comprises non-cell based binding assays, wherein a PAPAP polypeptide is prepared and purified as in cell based binding assays described above. Following purification, the proteins are labeled and incubated with a cell membrane extract or isolate derived from any desired cells from any organs, tissue or combination of organs or tissues of interest to allow the PAPAP polypeptide to bind to any receptor present on a membrane. Following the incubation, the membranes are washed to remove non-specifically bound protein. The labeled proteins may be detected by autoradiography. Specificity of membrane binding of PAPAP may be analyzed by conducting a competition analysis in which various amounts of a test compound are incubated along with the labeled protein. Any desired test compound, including test polypeptides, can be incubated with the cells. The test compounds may be detected with antibodies having a detectable label, such as a fluorescent molecule, attached thereto. The amount of labeled PAPAP polypeptide bound to the cell surface decreases as the amount of competitive test compound increases. As a control, various amounts of an unlabeled protein or a compound unrelated to the test compound is included in some binding reactions. Test compounds capable of reducing the amount of PAPAP bound to cell membranes may be selected as a candidate therapeutic compound. In one aspect, PAPAP binding may be used to detect a g34872 polypeptide.

In preferred embodiments of the cell and non-cell based assays, said PAPAP peptide comprising a contiguous span of at least 4, 6 or 8 contiguous amino acids of SEQ ID NO: 2.

Said cell based assays may comprise cells of any suitable origin; particularly preferred cells are human cells, primate cells, non-human primate cells and mouse cells.

Animal Model Based Assay

Non-human animal based assays may also be used to identify compounds which modulate PAPAP activity, to study PAPAP as well as to study g34872 and the g34872 biological pathway. The invention encompasses animal models and animal based assays suitable, including non-transgenic or transgenic animals, including animals lacking the PAPAP gene or expressing conditionally a PAPAP gene, or containing a human or altered form of the PAPAP gene.

Thus, the present invention comprises treating an animal affected by schizophrenia or bipolar disorder or symptoms thereof with a test compound capable of directly or indirectly modulating PAPAP activity.

In one aspect, an animal based assay of the invention encompasses a method for identifying a test compound for the treatment of schizophrenia or bipolar disorder comprising (a) exposing an animal to a test compound at a concentration and time sufficient to ameliorate an endpoint related to schizophrenia or bipolar disorder, and (b) determining the level of PAPAP activity or PAPAP-g34872 interaction or complexes at a site in said animal. PAPAP activity can be measured in any suitable cell, tissue or site. Preferably the test compound is a compound capable of or suspected to be capable of ameliorating a symptom of schizophrenia, bipolar disorder or a related disorder. Optionally said test compound is capable or suspected to be capable of modulating PAPAP activity. Test compounds capable of modulating PAPAP activity may be selected for use in developing medicaments. Several examples of test compounds are given herein (eg. benzodiazepines, selective serontonin reuptake inhibitors, etc.).

In another aspect, an animal based assay of the invention encompasses a method for identifying a compound for the treatment of schizophrenia or bipolar disorder comprising (a) exposing an animal to a level of PAPAP activity sufficient to cause a schizophrenia-related or bipolar disorder-related symptom or endpoint, and (b) exposing said animal to a test compound. A test compound can then be selected according to its ability to ameliorate said schizophrenia-related or bipolar disorder-related endpoints. PAPAP activity may be provided by any suitable method, including but not limited to providing a vector containing a PAPAP nucleotide sequence, treating said animal with a compound capable of increasing PAPAP expression and treating said cell with a PAPAP peptide. Preferably, said animal is treated with a PAPAP peptide comprising a contiguous span of at least 4, 6 or preferably 8 contiguous amino acids of SEQ ID NOs: 2. Preferably the test compound is a compound capable of or suspected to be capable of ameliorating a symptom of schizophrenia, bipolar disorder or a related disorder; alternatively, the test compound is suspected of exacerbating a symptom of schizophrenia, bipolar disorder or a related disorder. A test compound capable of ameliorating any detectable symptom or endpoint of a schizophrenia, bipolar disorder or a related disorder may be selected for use in developing medicaments.

In another embodiment, the present invention provides a method of identifying a modulator of PAPAP activity in vivo, the method comprising administering to a non-human animal a test agent, and detecting a PAPAP-related behavior or property of said animal, wherein a detected change in said behavior or property indicates that said test agent is a modulator of PAPAP activity. Said PAPAP related behavior or property can be any property related to any aspect of PAPAP activity, or of the activities of any PAPAP interacting proteins, such as CaM-KII or g34872. For example, such behaviors or properties can include learning, memory, cognitive function, or any feature associated with schizophrenia, bipolar disorder, or any related disorders. Methods of measuring learning and memory in experimental animals are well known in the art.

In one embodiment, a mouse or other animal is treated with a PAPAP peptide, exposed to a test compound, and symptoms indicative of schizophrenia, bipolar disorder or a related disorder are assessed by observing stereotypy. In other embodiments, said symptoms are assessed by performing at least one test from the group consisting of home cage observation, neurological evaluation, stress-induced hypothermia, forced swim, PTZ seizure, locomotor activity, tail suspension, elevated plus maze, novel object recognition, prepulse inhibition, thermal pain, Y-maze, and metabolic chamber tests (Psychoscreen™ tests available from Psychogenics Inc.). Other tests are known in Crawley et al, Horm. Behav. 31(3): 197-211 (1997); Crawley, Brain Res 835(1):18-26 (1999) for example.

Any suitable test compound may be used with the screening methods of the invention. Examples of compounds that may be screened by the methods of the present invention include small organic or inorganic molecules, nucleic acids, including polynucleotides from random and directed polynucleotide libraries, peptides, including peptides derived from random and directed peptide libraries, soluble peptides, fusion peptides, and phosphopeptides, antibodies including polyclonal, monoclonal, chimeric, humanized, and anti-idiotypic antibodies, and single chain antibodies, FAb, F(ab')$_2$ and FAb expression library fragments, and epitope-binding fragments thereof. In certain aspects, a compound capable of ameliorating or exacerbating a symptom or endpoint of schizophrenia, bipolar disorder or a related disorder may include, by way of example, antipsychotic drugs in general, neuroleptics, atypical neuroleptics, antidepressants, anti-anxiety drugs, noradrenergic agonists and antagonists, dopaminergic agonists and antagonists, serotonin reuptake inhibitors, benzodiazepines.

In these assays, the test compound can be administered (e.g. IV, IP, 1M, orally, or otherwise), to the animal, for example, at a variety of dose levels. The effect of the compound on PAPAP expression is determined by comparing PAPAP levels, for example, in blood, or in a selected tissue, using Northern blots, immunoassays, PCR, etc., as described above. Any suitable animal may be used. Preferably, said animal is a primate, a non-human primate, a mammal, or a mouse. Humanized mice can also be used as test animals, that is mice in which the endogenous mouse protein is ablated (knocked out) and the homologous human protein added back by standard transgenic approaches. Such mice express only the human form of a protein. Humanized mice expressing just the human PAPAP can be used to study in vivo responses symptomatic of CNS disorders in response to potential agents regulating PAPAP protein or mRNA levels, or PAPAP-g34872 interactions or complexes. As an example, transgenic mice have been produced carrying the human apoE4 gene. They are then bred with a mouse line that lacks endogenous apoE, to produce an animal model carrying human proteins believed to be instrumental in development of Alzheimers pathology. Such transgenic animals are useful for dissecting the biochemical and physiological steps of disease, and for development of therapies for disease intervention (Loring, et al, Neurobiol. Aging 17:173 (1996) incorporated herein by reference in its entirety).

Methods for Screening Substances Interacting with a PAPAP Polypeptide

For the purpose of the present invention, a ligand means a molecule, such as a protein, a peptide, an antibody or any synthetic chemical compound capable of binding to the PAPAP protein or one of its fragments or variants or to modulate the expression of the polynucleotide coding for PAPAP or a fragment or variant thereof.

In the ligand screening method according to the present invention, a biological sample or a defined molecule to be tested as a putative ligand of the PAPAP protein is brought into contact with the corresponding purified PAPAP protein, for example the corresponding purified recombinant PAPAP protein produced by a recombinant cell host as described hereinbefore, in order to form a complex between this protein and the putative ligand molecule to be tested.

As an illustrative example, to study the interaction of the PAPAP protein, or a fragment comprising a contiguous span of at least 6 amino acids, preferably at least 8 to 10 amino acids, more preferably at least 12, 15, 20, 25, 30, 40, 50, or 100 amino acids of SEQ ID NO: 2, with drugs or small molecules, such as molecules generated through combinatorial chemistry approaches, the microdialysis coupled to HPLC method described by Wang et al. (1997) or the affinity capillary electrophoresis method described by Bush et al. (1997), the disclosures of which are incorporated by reference, can be used.

In further methods, peptides, drugs, fatty acids, lipoproteins, or small molecules which interact with the PAPAP protein, or a fragment comprising a contiguous span of at least 6 amino acids, preferably at least 8 to 10 amino acids, more preferably at least 12, 15, 20, 25, 30, 40, 50, or 100 amino acids of SEQ ID NO: 2, may be identified using assays such as the following. The molecule to be tested for binding is labeled with a detectable label, such as a fluorescent, radioactive, or enzymatic tag and placed in contact with immobilized PAPAP protein, or a fragment thereof under conditions which permit specific binding to occur. After removal of non-specifically bound molecules, bound molecules are detected using appropriate means.

Another object of the present invention comprises methods and kits for the screening of candidate substances that interact with PAPAP polypeptide.

The present invention pertains to methods for screening substances of interest that interact with a PAPAP protein or one fragment or variant thereof. By their capacity to bind covalently or non-covalently to a PAPAP protein or to a fragment or variant thereof, these substances or molecules may be advantageously used both in vitro and in vivo.

In vitro, said interacting molecules may be used as detection means in order to identify the presence of a PAPAP protein in a sample, preferably a biological sample.

A method for the screening of a candidate substance comprises the following steps:

a) providing a polypeptide comprising, consisting essentially of, or consisting of a PAPAP protein or a fragment comprising a contiguous span of at least 6 amino acids, preferably at least 8 to 10 amino acids, more preferably at least 12, 15, 20, 25, 30, 40, 50, or 100 amino acids of SEQ ID NO: 2;

b) obtaining a candidate substance;

c) bringing into contact said polypeptide with said candidate substance;

d) detecting the complexes formed between said polypeptide and said candidate substance.

In one embodiment, the invention relates to the use of PAPAP for the study of g34872 pathway in CNS disorders. Methods for screening for interacting substances may be used to detect interaction of PAPAP and g34872. Thus, the invention also comprises:

a) providing a polypeptide comprising, consisting essentially of, or consisting of a PAPAP protein or a fragment comprising a contiguous span of at least 6 amino acids, preferably at least 8 to 10 amino acids, more preferably at least 12, 15, 20, 25, 30, 40, 50, or 100 amino acids of SEQ ID NO: 2;

b) obtaining a g34872 polypeptide;

c) bringing into contact said PAPAP polypeptide with a g34872 polypeptide;

d) detecting the complexes formed between said PAPAP polypeptide and said g34872 polypeptide.

Preferably, said g34872 polypeptide comprises at least 4, 6 or preferably 8 contiguous amino acids of the amino acid sequence of SEQ ID NO: 5.

The invention further concerns a kit for the screening of a candidate substance interacting with the PAPAP polypeptide, wherein said kit comprises:

a) a PAPAP protein having an amino acid sequence selected from the group consisting of the amino acid sequences of SEQ ID NO: 2 or a peptide fragment comprising a contiguous span of at least 6 amino acids, preferably at least 8 to 10 amino acids, more preferably at least 12, 15, 20, 25, 30, 40, 50, or 100 amino acids of SEQ ID NO: 2;

b) optionally means useful to detect the complex formed between the PAPAP protein or a peptide fragment or a variant thereof and the candidate substance.

In a preferred embodiment of the kit described above, the detection means comprises a monoclonal or polyclonal antibodies directed against the PAPAP protein or a peptide fragment or a variant thereof.

Various candidate substances or molecules can be assayed for interaction with a PAPAP polypeptide. These substances or molecules include, without being limited to, natural or synthetic organic compounds or molecules of biological origin such as polypeptides. When the candidate substance or molecule comprises a polypeptide, this polypeptide may be the resulting expression product of a phage clone belonging to a phage-based random peptide library, or alternatively the polypeptide may be the resulting expression product of a cDNA library cloned in a vector suitable for performing a two-hybrid screening assay.

The invention also pertains to kits useful for performing the hereinbefore described screening method. Preferably, such kits comprise a PAPAP polypeptide or a fragment or a variant thereof, and optionally means useful to detect the complex formed between the PAPAP polypeptide or its fragment or variant and the candidate substance. In a preferred embodiment the detection means comprise a monoclonal or polyclonal antibodies directed against the corresponding PAPAP polypeptide or a fragment or a variant thereof.

A. Candidate Ligands Obtained from Random Peptide Libraries

In a particular embodiment of the screening method, the putative ligand is the expression product of a DNA insert contained in a phage vector (Parmley and Smith, 1988). Specifically, random peptide phages libraries are used. The random DNA inserts encode for peptides of 8 to 20 amino acids in length (Oldenburg K. R. et al., 1992; Valadon P., et al., 1996; Lucas A. H., 1994; Westerink M. A. J., 1995; Felici F. et al., 1991). According to this particular embodiment, the recombinant phages expressing a protein that binds to the immobilized PAPAP protein is retained and the complex formed between the PAPAP protein and the recombinant phage may be subsequently immunoprecipitated by a polyclonal or a monoclonal antibody directed against the PAPAP protein.

Once the ligand library in recombinant phages has been constructed, the phage population is brought into contact with the immobilized PAPAP protein. Then the preparation of complexes is washed in order to remove the non-specifically bound recombinant phages. The phages that bind specifically to the PAPAP protein are then eluted by a buffer (acid pH) or immunoprecipitated by the monoclonal antibody produced by the hybridoma anti-PAPAP, and this phage population is subsequently amplified by an over-infection of bacteria (for example *E. coli*). The selection step may be repeated several times, preferably 2-4 times, in order to select the more specific recombinant phage clones. The last step comprises characterizing the peptide produced by the selected recombinant phage clones either by expression in infected bacteria and isolation, expressing the phage insert in another host-vector system, or sequencing the insert contained in the selected recombinant phages.

B. Candidate Ligands Obtained by Competition Experiments.

Alternatively, peptides, drugs or small molecules which bind to the PAPAP protein, or a fragment comprising a contiguous span of at least 6 amino acids, preferably at least 8 to 10 amino acids, more preferably at least 12, 15, 20, 25, 30, 40, 50, or 100 amino acids of SEQ ID NO: 2, may be identified in competition experiments. In such assays, the PAPAP protein, or a fragment thereof, is immobilized to a surface, such as a plastic plate. Increasing amounts of the peptides, drugs or small molecules are placed in contact with the immobilized PAPAP protein, or a fragment thereof, in the presence of a detectable labeled known PAPAP protein ligand. For example, the PAPAP ligand may be detectably labeled with a fluorescent, radioactive, or enzymatic tag. The ability of the test molecule to bind the PAPAP protein, or a fragment thereof, is determined by measuring the amount of detectably labeled known ligand bound in the presence of the test molecule. A decrease in the amount of known ligand bound to the PAPAP protein, or a fragment thereof, when the test molecule is present indicated that the test molecule is able to bind to the PAPAP protein, or a fragment thereof.

C. Candidate Ligands Obtained by Affinity Chromatography.

Proteins or other molecules interacting with the PAPAP protein, or a fragment comprising a contiguous span of at least 6 amino acids, preferably at least 8 to 10 amino acids, more preferably at least 12, 15, 20, 25, 30, 40, 50, or 100 amino acids of SEQ ID NO: 2, can also be found using affinity columns which contain the PAPAP protein, or a fragment thereof. The PAPAP protein, or a fragment thereof, may be attached to the column using conventional techniques including chemical coupling to a suitable column matrix such as agarose, AFFI-GEL, or other matrices familiar to those of skill in art. In some embodiments of this method, the affinity column contains chimeric proteins in which the PAPAP protein, or a fragment thereof, is fused to glutathion S transferase (GST). A mixture of cellular proteins or pool of expressed proteins as described above is applied to the affinity column. Proteins or other molecules interacting with the PAPAP protein, or a fragment thereof, attached to the column can then be isolated and analyzed on 2-D electrophoresis gel as described in Ramunsen et al. (1997), the disclosure of which is incorporated by reference. Alternatively, the proteins retained on the affinity column can be purified by electrophoresis based methods and sequenced. The same method can be used to isolate antibodies, to screen phage display products, or to screen phage display human antibodies.

D. Candidate Ligands Obtained by Optical Biosensor Methods

Proteins interacting with the PAPAP protein, or a fragment comprising a contiguous span of at least 6 amino acids, preferably at least 8 to 10 amino acids, more preferably at least 12, 15, 20, 25, 30, 40, 50, or 100 amino acids of SEQ ID NO: 2, can also be screened by using an Optical Biosensor as described in Edwards and Leatherbarrow (1997) and also in Szabo et al. (1995), the disclosures of which are incorporated by reference. This technique permits the detection of interactions between molecules in real time, without the need of labeled molecules. This technique is based on the surface plasmon resonance (SPR) phenomenon. Briefly, the candidate ligand molecule to be tested is attached to a surface (such as a carboxymethyl dextran matrix). A light beam is directed towards the side of the surface that does not contain the sample to be tested and is reflected by said surface. The SPR phenomenon causes a decrease in the intensity of the reflected light with a specific association of angle and wavelength. The binding of candidate ligand molecules cause a change in the refraction index on the surface, which change is detected as a change in the SPR signal. For screening of candidate ligand molecules or substances that are able to interact with the PAPAP protein, or a fragment thereof, the PAPAP protein, or a fragment thereof, is immobilized onto a surface. This surface comprises one side of a cell through which flows the candidate molecule to be assayed. The binding of the candidate molecule on the PAPAP protein, or a fragment thereof, is detected as a change of the SPR signal. The candidate molecules tested may be proteins, peptides, carbohydrates, lipids, or small molecules generated by combinatorial chemistry. This technique may also be performed by immobilizing eukaryotic or prokaryotic cells or lipid vesicles exhibiting an endogenous or a recombinantly expressed PAPAP protein at their surface.

The main advantage of the method is that it allows the determination of the association rate between the PAPAP protein and molecules interacting with the PAPAP protein. It is thus possible to select specifically ligand molecules interacting with the PAPAP protein, or a fragment thereof, through strong or conversely weak association constants.

E. Candidate Ligands Obtained Through a Two-Hybrid Screening Assay.

The yeast two-hybrid system is designed to study protein-protein interactions in vivo (Fields and Song, 1989), and relies upon the fusion of a bait protein to the DNA binding domain of the yeast Gal4 protein. This technique is also described in the U.S. Pat. No. 5,667,973 and the U.S. Pat. No. 5,283,173 (Fields et al.) the technical teachings of both patents being herein incorporated by reference.

The general procedure of library screening by the two-hybrid assay may be performed as described by Harper et al. (1993) or as described by Cho et al. (1998) or also Fromont-Racine et al. (1997).

The bait protein or polypeptide comprises, consists essentially of, or consists of a PAPAP polypeptide or a fragment comprising a contiguous span of at least 6 amino acids, preferably at least 8 to 10 amino acids, more preferably at least 12, 15, 20, 25, 30, 40, 50, or 100 amino acids of SEQ ID NO: 2.

More precisely, the nucleotide sequence encoding the PAPAP polypeptide or a fragment or variant thereof is fused to a polynucleotide encoding the DNA binding domain of the GAL4 protein, the fused nucleotide sequence being inserted in a suitable expression vector, for example pAS2 or pM3.

Then, a human cDNA library is constructed in a specially designed vector, such that the human cDNA insert is fused to a nucleotide sequence in the vector that encodes the transcriptional domain of the GAL4 protein. Preferably, the vector used is the pACT vector. The polypeptides encoded by the nucleotide inserts of the human cDNA library are termed "pray" polypeptides.

A third vector contains a detectable marker gene, such as beta galactosidase gene or CAT gene that is placed under the control of a regulation sequence that is responsive to the binding of a complete Gal4 protein containing both the transcriptional activation domain and the DNA binding domain. For example, the vector pG5EC may be used.

Two different yeast strains are also used. As an illustrative but non limiting example the two different yeast strains may be the followings:

Y190, the phenotype of which is (MATa, Leu2-3, 112 ura3-12, trpl-901, his3-D200, ade2-101, gal4Dgal180D URA3 GAL-LacZ, LYS GAL-HIS3, cyh');

Y187, the phenotype of which is (MATa gal4 gal80 his3 trp1-901 ade2-101 ura3-52 leu2-3, –112 URA3 GAL-lacZmet⁻), which is the opposite mating type of Y190.

Briefly, 20 µg of pAS2/PAPAP and 20 µg of pACT-cDNA library are co-transformed into yeast strain Y190. The transformants are selected for growth on minimal media lacking histidine, leucine and tryptophan, but containing the histidine synthesis inhibitor 3-AT (50 mM). Positive colonies are screened for beta galactosidase by filter lift assay. The double positive colonies (His⁺, beta-gal⁺) are then grown on plates lacking histidine, leucine, but containing tryptophan and cycloheximide (10 mg/ml) to select for loss of pAS2/PAPAP plasmids bu retention of pACT-cDNA library plasmids. The resulting Y190 strains are mated with Y187 strains expressing PAPAP or non-related control proteins; such as cyclophilin B, lamin, or SNF1, as Gal4 fusions as described by Harper et al. (1993) and by Bram et al. (Bram R J et al., 1993), and screened for beta galactosidase by filter lift assay. Yeast clones that are beta gal—after mating with the control Gal4 fusions are considered false positives.

In another embodiment of the two-hybrid method according to the invention, interaction between the PAPAP or a fragment or variant thereof with cellular proteins may be assessed using the Matchmaker Two Hybrid System 2 (Catalog No. K1604-1, Clontech). As described in the manual accompanying the Matchmaker Two Hybrid System 2 (Catalog No. K1604-1, Clontech), the disclosure of which is incorporated herein by reference, nucleic acids encoding the PAPAP protein or a portion thereof, are inserted into an expression vector such that they are in frame with DNA encoding the DNA binding domain of the yeast transcriptional activator GAL4. A desired cDNA, preferably human cDNA, is inserted into a second expression vector such that they are in frame with DNA encoding the activation domain of GAL4. The two expression plasmids are transformed into yeast and the yeast are plated on selection medium which selects for expression of selectable markers on each of the expression vectors as well as GAL4 dependent expression of the HIS3 gene. Transformants capable of growing on medium lacking histidine are screened for GAL4 dependent lacZ expression. Those cells which are positive in both the histidine selection and the lacZ assay contain interaction between PAPAP and the protein or peptide encoded by the initially selected cDNA insert.

Method for Screening Substances Interacting with the Regulatory Sequences of the PAPAP Gene.

The present invention also concerns a method for screening substances or molecules that are able to interact with the regulatory sequences of the PAPAP gene, such as for example promoter or enhancer sequences.

Nucleic acids encoding proteins which are able to interact with the regulatory sequences of the PAPAP gene, more particularly a nucleotide sequence selected from the group consisting of the polynucleotides of the 5' and 3' regulatory region or a fragment or variant thereof, and preferably a variant comprising one of the biallelic markers of the invention, may be identified by using a one-hybrid system, such as that described in the booklet enclosed in the Matchmaker One-Hybrid System kit from Clontech (Catalog Ref. no K1603-1), the technical teachings of which are herein incorporated by reference. Briefly, the target nucleotide sequence is cloned upstream of a selectable reporter sequence and the resulting DNA construct is integrated in the yeast genome (*Saccharomyces cerevisiae*). The yeast cells containing the reporter sequence in their genome are then transformed with a library comprising fusion molecules between cDNAs encoding candidate proteins for binding onto the regulatory sequences of the PAPAP gene and sequences encoding the activator domain of a yeast transcription factor such as GAL4. The recombinant yeast cells are plated in a culture broth for selecting cells expressing the reporter sequence. The recombinant yeast cells thus selected contain a fusion protein that is able to bind onto the target regulatory sequence of the PAPAP gene. Then, the cDNAs encoding the fusion proteins are sequenced and may be cloned into expression or transcription vectors in vitro. The binding of the encoded polypeptides to the target regulatory sequences of the PAPAP gene may be confirmed by techniques familiar to the one skilled in the art, such as gel retardation assays or DNAse protection assays.

Gel retardation assays may also be performed independently in order to screen candidate molecules that are able to interact with the regulatory sequences of the PAPAP gene, such as described by Fried and Crothers (1981), Garner and Revzin (1981) and Dent and Latchman (1993), the teachings of these publications being herein incorporated by reference. These techniques are based on the principle according to which a DNA fragment which is bound to a protein migrates slower than the same unbound DNA fragment. Briefly, the target nucleotide sequence is labeled. Then the labeled target nucleotide sequence is brought into contact with either a total nuclear extract from cells containing transcription factors, or with different candidate molecules to be tested. The interaction between the target regulatory sequence of the PAPAP gene and the candidate molecule or the transcription factor is detected after gel or capillary electrophoresis through a retardation in the migration.

Method for Screening Ligands that Modulate the Expression of the PAPAP Gene.

Another subject of the present invention is a method for screening molecules that modulate the expression of the PAPAP protein. Such a screening method comprises the steps of:

a) cultivating a prokaryotic or an eukaryotic cell that has been transfected with a nucleotide sequence encoding the PAPAP protein or a variant or a fragment thereof, placed under the control of its own promoter;

b) bringing into contact the cultivated cell with a molecule to be tested;

c) quantifying the expression of the PAPAP protein or a variant or a fragment thereof.

In an embodiment, the nucleotide sequence encoding the PAPAP protein or a variant or a fragment thereof comprises an allele of at least one PAPAP-related biallelic markers, and the complements thereof.

Using DNA recombination techniques well known by the one skill in the art, the PAPAP protein encoding DNA sequence is inserted into an expression vector, downstream from its promoter sequence. As an illustrative example, the promoter sequence of the PAPAP gene is contained in the nucleic acid of the 5' regulatory region.

The quantification of the expression of the PAPAP protein may be realized either at the mRNA level or at the protein level. In the latter case, polyclonal or monoclonal antibodies may be used to quantify the amounts of the PAPAP protein that have been produced, for example in an ELISA or a RIA assay.

In a preferred embodiment, the quantification of the PAPAP mRNA is realized by a quantitative PCR amplification of the cDNA obtained by a reverse transcription of the total mRNA of the cultivated PAPAP-transfected host cell, using a pair of primers specific for PAPAP.

The present invention also concerns a method for screening substances or molecules that are able to increase, or in contrast to decrease, the level of expression of the PAPAP gene. Such a method may allow the one skilled in the art to select substances exerting a regulating effect on the expression level of the PAPAP gene and which may be useful as active ingredients included in pharmaceutical compositions for treating patients suffering from schizophrenia, bipolar disorder or related central nervous system disorders.

Thus, also part of the present invention is a method for screening of a candidate substance or molecule that modulated the expression of the PAPAP gene, this method comprises the following steps:

providing a recombinant cell host containing a nucleic acid, wherein said nucleic acid comprises a nucleotide sequence of the 5' regulatory region or a biologically active fragment or variant thereof located upstream a polynucleotide encoding a detectable protein;

obtaining a candidate substance; and determining the ability of the candidate substance to modulate the expression levels of the polynucleotide encoding the detectable protein.

In a further embodiment, the nucleic acid comprising the nucleotide sequence of the 5' regulatory region or a biologically active fragment or variant thereof also includes a 5'UTR region of the PAPAP cDNA of SEQ ID NO: 1, or one of its biologically active fragments or variants thereof.

Among the preferred polynucleotides encoding a detectable protein, there may be cited polynucleotides encoding beta galactosidase, green fluorescent protein (GFP) and chloramphenicol acetyl transferase (CAT).

The invention also pertains to kits useful for performing the herein described screening method. Preferably, such kits comprise a recombinant vector that allows the expression of a nucleotide sequence of the 5' regulatory region or a biologically active fragment or variant thereof located upstream and operably linked to a polynucleotide encoding a detectable protein or the PAPAP protein or a fragment or a variant thereof.

In another embodiment of a method for the screening of a candidate substance or molecule that modulates the expression of the PAPAP gene, wherein said method comprises the following steps:

a) providing a recombinant host cell containing a nucleic acid, wherein said nucleic acid comprises a 5'UTR sequence of the PAPAP cDNA of SEQ ID NO: 1, or one of its biologically active fragments or variants, the 5'UTR sequence or its biologically active fragment or variant being operably linked to a polynucleotide encoding a detectable protein;

b) obtaining a candidate substance; and c) determining the ability of the candidate substance to modulate the expression levels of the polynucleotide encoding the detectable protein.

In a specific embodiment of the above screening method, the nucleic acid that comprises a nucleotide sequence selected from the group consisting of the 5'UTR sequence of the PAPAP cDNA of SEQ ID NO: 1 or one of its biologically active fragments or variants, includes a promoter sequence which is endogenous with respect to the PAPAP 5'UTR sequence.

In another specific embodiment of the above screening method, the nucleic acid that comprises a nucleotide sequence selected from the group consisting of the 5'UTR sequence of the PAPAP cDNA of SEQ ID NO: 1 or one of its biologically active fragments or variants, includes a promoter sequence which is exogenous with respect to the PAPAP 5'UTR sequence defined therein.

In a further preferred embodiment, the nucleic acid comprising the 5'-UTR sequence of the PAPAP cDNA or SEQ ID NO: 1 or the biologically active fragments thereof includes a PAPAP-related biallelic marker, or the complements thereof.

The invention further comprises with a kit for the screening of a candidate substance modulating the expression of the PAPAP gene, wherein said kit comprises a recombinant vector that comprises a nucleic acid including a 5'UTR sequence of the PAPAP cDNA of SEQ ID NO: 1, or one of their biologically active fragments or variants, the 5'UTR sequence or its biologically active fragment or variant being operably linked to a polynucleotide encoding a detectable protein.

For the design of suitable recombinant vectors useful for performing the screening methods described above, it will be referred to the section of the present specification wherein the preferred recombinant vectors of the invention are detailed. Expression levels and patterns of PAPAP may be analyzed by solution hybridization with long probes as described in International Patent Application No. WO 97/05277, the entire contents of which are incorporated herein by reference. Briefly, the PAPAP cDNA or the PAPAP genomic DNA described above, or fragments thereof, is inserted at a cloning site immediately downstream of a bacteriophage (T3, T7 or SP6) RNA polymerase promoter to produce antisense RNA. Preferably, the PAPAP insert comprises at least 100 or more consecutive nucleotides of the genomic DNA sequence or the cDNA sequences. The plasmid is linearized and transcribed in the presence of ribonucleotides comprising modified ribonucleotides (i.e. biotin-UTP and DIG-UTP). An excess of this doubly labeled RNA is hybridized in solution with mRNA isolated from cells or tissues of interest. The hybridization is performed under standard stringent conditions (40-50° C. for 16 hours in an 80% formamide, 0.4 M NaCl buffer, pH 7-8). The unhybridized probe is removed by digestion with ribonucleases specific for single-stranded RNA (i.e. RNases CL3, T1, Phy M, U2 or A). The presence of the biotin-UTP modification enables capture of the hybrid on a microtitration plate coated with streptavidin. The presence of the DIG modification enables the hybrid to be detected and quantified by ELISA using an anti-DIG antibody coupled to alkaline phosphatase.

Quantitative analysis of PAPAP gene expression may also be performed using arrays. As used herein, the term array means a one dimensional, two dimensional, or multidimensional arrangement of a plurality of nucleic acids of sufficient length to permit specific detection of expression of mRNAs capable of hybridizing thereto. For example, the arrays may contain a plurality of nucleic acids derived from genes whose expression levels are to be assessed. The arrays may include the PAPAP genomic DNA, the PAPAP cDNA sequences or the sequences complementary thereto or fragments thereof, particularly those comprising at least one PAPAP related biallelic marker. Preferably, the fragments are at least 15 nucleotides in length. In other embodiments, the fragments are at least 25 nucleotides in length. In some embodiments, the fragments are at least 50 nucleotides in length. More preferably, the fragments are at least 100 nucleotides in length. In another preferred embodiment, the fragments are more than 100 nucleotides in length. In some embodiments the fragments may be more than 500 nucleotides in length.

For example, quantitative analysis of PAPAP gene expression may be performed with a complementary DNA microarray as described by Schena et al. (1995 and 1996). Full length PAPAP cDNAs or fragments thereof are amplified by PCR and arrayed from a 96-well microtiter plate onto silylated microscope slides using high-speed robotics. Printed arrays are incubated in a humid chamber to allow rehydration of the array elements and rinsed, once in 0.2% SDS for 1 min, twice in water for 1 min and once for 5 min in sodium borohydride solution. The arrays are submerged in water for 2 min at 95° C., transferred into 0.2% SDS for 1 min, rinsed twice with water, air dried and stored in the dark at 25° C.

Cell or tissue mRNA is isolated or commercially obtained and probes are prepared by a single round of reverse transcription. Probes are hybridized to 1 $cm^2$ microarrays under a 14×14 mm glass coverslip for 6-12 hours at 60° C. Arrays are washed for 5 min at 25° C. in low stringency wash buffer (1×SSC/0.2% SDS), then for 10 min at room temperature in high stringency wash buffer (0.1×SSC/0.2% SDS). Arrays are scanned in 0.1×SSC using a fluorescence laser scanning device fitted with a custom filter set. Accurate differential expression measurements are obtained by taking the average of the ratios of two independent hybridizations.

Quantitative analysis of PAPAP gene expression may also be performed with full length PAPAP cDNAs or fragments thereof in complementary DNA arrays as described by Pietu et al. (1996). The full length PAPAP cDNA or fragments thereof is PCR amplified and spotted on membranes. Then, mRNAs originating from various tissues or cells are labeled with radioactive nucleotides. After hybridization and washing in controlled conditions, the hybridized mRNAs are detected by phospho-imaging or autoradiography. Duplicate experiments are performed and a quantitative analysis of differentially expressed mRNAs is then performed.

Alternatively, expression analysis using the PAPAP genomic DNA, the PAPAP cDNA, or fragments thereof can be done through high density nucleotide arrays as described by Lockhart et al. (1996) and Sosnowsky et al. (1997). Oligonucleotides of 15-50 nucleotides from the sequences of the PAPAP genomic DNA, the PAPAP cDNA sequences, or the sequences complementary thereto, are synthesized directly on the chip (Lockhart et al., supra) or synthesized and then addressed to the chip (Sosnowski et al., supra). Preferably, the oligonucleotides are about 20 nucleotides in length.

PAPAP cDNA probes labeled with an appropriate compound, such as biotin, digoxigenin or fluorescent dye, are synthesized from the appropriate mRNA population and then randomly fragmented to an average size of 50 to 100 nucleotides. The said probes are then hybridized to the chip. After washing as described in Lockhart et al., supra and application of different electric fields (Sosnowsky et al., 1997)., the dyes or labeling compounds are detected and quantified. Duplicate hybridizations are performed. Comparative analysis of the intensity of the signal originating from cDNA probes on the same target oligonucleotide in different cDNA samples indicates a differential expression of PAPAP mRNA.

Methods for Inhibiting the Expression of a PAPAP Gene

Other therapeutic compositions according to the present invention comprise advantageously an oligonucleotide fragment of the nucleic sequence of PAPAP as an antisense tool or a triple helix tool that inhibits the expression of the corresponding PAPAP gene.

Antisense Approach

Preferred methods using antisense polynucleotide according to the present invention are the procedures described by Sczakiel et al. (1995).

Preferably, the antisense tools are chosen among the polynucleotides (15-200 bp long) that are complementary to the 5' end of the PAPAP mRNA. In another embodiment, a combination of different antisense polynucleotides complementary to different parts of the desired targeted gene are used.

Preferred antisense polynucleotides according to the present invention are complementary to a sequence of the mRNAs of PAPAP that contains either the translation initiation codon ATG or a splicing donor or acceptor site.

The antisense nucleic acids should have a length and melting temperature sufficient to permit formation of an intracellular duplex having sufficient stability to inhibit the expression of the PAPAP mRNA in the duplex. Strategies for designing antisense nucleic acids suitable for use in gene therapy are disclosed in Green et al., (1986) and Izant and Weintraub, (1984), the disclosures of which are incorporated herein by reference.

In some strategies, antisense molecules are obtained by reversing the orientation of the PAPAP coding region with respect to a promoter so as to transcribe the opposite strand from that which is normally transcribed in the cell. The antisense molecules may be transcribed using in vitro transcription systems such as those which employ T7 or SP6 polymerase to generate the transcript. Another approach involves transcription of PAPAP antisense nucleic acids in vivo by operably linking DNA containing the antisense sequence to a promoter in a suitable expression vector.

Alternatively, suitable antisense strategies are those described by Rossi et al. (1991), in the International Applications Nos. WO 94/23026, WO 95/04141, WO 92/18522 and in the European Patent Application No. EP 0 572 287 A2

An alternative to the antisense technology that is used according to the present invention comprises using ribozymes that will bind to a target sequence via their complementary polynucleotide tail and that will cleave the corresponding RNA by hydrolyzing its target site (namely "hammerhead ribozymes"). Briefly, the simplified cycle of a hammerhead ribozyme comprises (1) sequence specific binding to the target RNA via complementary antisense sequences; (2) site-specific hydrolysis of the cleavable motif of the target strand; and (3) release of cleavage products, which gives rise to another catalytic cycle. Indeed, the use of long-chain antisense polynucleotide (at least 30 bases long) or ribozymes with long antisense arms are advantageous. A preferred delivery system for antisense ribozyme is achieved by covalently linking these antisense ribozymes to lipophilic groups or to use liposomes as a convenient vector. Preferred antisense ribozymes according to the present invention are prepared as described by Sczakiel et al. (1995), the specific preparation procedures being referred to in said article being herein incorporated by reference.

Triple Helix Approach

The PAPAP genomic DNA may also be used to inhibit the expression of the PAPAP gene based on intracellular triple helix formation.

Triple helix oligonucleotides are used to inhibit transcription from a genome. They are particularly useful for studying alterations in cell activity when it is associated with a particular gene.

Similarly, a portion of the PAPAP genomic DNA can be used to study the effect of inhibiting PAPAP transcription within a cell. Traditionally, homopurine sequences were considered the most useful for triple helix strategies. However, homopyrimidine sequences can also inhibit gene expression. Such homopyrimidine oligonucleotides bind to the major groove at homopurine:homopyrimidine sequences. Thus, both types of sequences from the PAPAP genomic DNA are contemplated within the scope of this invention.

To carry out gene therapy strategies using the triple helix approach, the sequences of the PAPAP genomic DNA are first scanned to identify 10-mer to 20-mer homopyrimidine or homopurine stretches which could be used in triple-helix based strategies for inhibiting PAPAP expression. Following identification of candidate homopyrimidine or homopurine stretches, their efficiency in inhibiting PAPAP expression is assessed by introducing varying amounts of oligonucleotides containing the candidate sequences into tissue culture cells which express the PAPAP gene.

The oligonucleotides can be introduced into the cells using a variety of methods known to those skilled in the art, including but not limited to calcium phosphate precipitation, DEAE-Dextran, electroporation, liposome-mediated transfection or native uptake.

Treated cells are monitored for altered cell function or reduced PAPAP expression using techniques such as Northern blotting, RNase protection assays, or PCR based strategies to monitor the transcription levels of the PAPAP gene in cells which have been treated with the oligonucleotide.

The oligonucleotides which are effective in inhibiting gene expression in tissue culture cells may then be introduced in vivo using the techniques described above in the antisense approach at a dosage calculated based on the in vitro results, as described in antisense approach.

In some embodiments, the natural (beta) anomers of the oligonucleotide units can be replaced with alpha anomers to render the oligonucleotide more resistant to nucleases. Further, an intercalating agent such as ethidium bromide, or the like, can be attached to the 3☐ end of the alpha oligonucleotide to stabilize the triple helix. For information on the generation of oligonucleotides suitable for triple helix formation see Griffin et al. (1989), which is hereby incorporated by this reference.

Pharmaceutical Compositions and Formulations

PAPAP-Modulating Compounds

Using the methods disclosed herein, PAPAP polypeptides and polynucleotides, as well as compounds that selectively modulate PAPAP activity or modulate PAPAP-g34872 or PAPAP CaM-KII interaction in vitro and in vivo may be used in any of a variety of applications. The compounds identified by the process of the invention include, for example, antibodies having binding specificity for the PAPAP peptide. It is also expected that homologues of PAPAP may be useful for modulating PAPAP-mediated activity and the related physiological condition associated with schizophrenia or bipolar disorder. Generally, it is expected that assay methods of the present invention based on the role of PAPAP in central nervous system disorder may be used to identify compounds capable of intervening in the disease pathway.

Indications

In one embodiment, modulators that inhibit PAPAP expression or activity can be used to increase CaM-KII activity in a cell or an animal, thereby enhancing learning, memory, and cognitive function, as well as glutaminergic synaptic activity, providing a treatment for schizophrenia and bipolar disorder, and also cell cycle progression and cell cycle associated organelle transport. Such methods may be performed in a cell or animal deficient for CaM-KII activity, or in a cell or animal with normal levels but which would nevertheless benefit from an increase in the kinase activity. Alternatively, modulators that promote PAPAP expression or activity can be used to inhibit CaM-kII activity in a cell or an animal, which is useful for example to reduce the level of glutaminergic synaptic activity, and also to inhibit cell cycle progression, for example to inhibit the proliferation of a cancerous cell.

While PAPAP has demonstrated an association with schizophrenia and bipolar disorder, indications involving PAPAP may also include other central nervous system disorders. Nervous system disorders are expected to have complex genetic bases and often share certain symptoms. In particular, as described herein, indications may include schizophrenia and other psychotic disorders, neurodegenerative disorders, mood disorders, autism, substance dependence and alcoholism, mental retardation, and other psychiatric diseases including cognitive, anxiety, eating, impulse-control, and personality disorders, as defined with the Diagnosis and Statistical Manual of Mental Disorders fourth edition (DSM-IV) classification.

Pharmaceutical Formulations and Routes of Administration

The compounds identified using the methods of the present invention can be administered to a mammal, including a human patient, alone or in pharmaceutical compositions where they are mixed with suitable carriers or excipient(s) at therapeutically effective doses to treat or ameliorate schizophrenia or bipolar disorder related disorders. A therapeutically effective dose further refers to that amount of the compound sufficient to result in amelioration of symptoms as determined by the methods described herein. Preferably, a therapeutically effective dosage is suitable for continued periodic use or administration. Techniques for formulation and administration of the compounds of the instant application may be found in "Remington's Pharmaceutical Sciences," Mack Publishing Co., Easton, Pa., latest edition.

Routes of Administration

Suitable routes of administration include oral, rectal, transmucosal, or intestinal administration, parenteral delivery, including intramuscular, subcutaneous, intramedullary injections, as well as intrathecal, direct intraventricular, intravenous, intraperitoneal, intranasal or intraocular injections. A particularly useful method of administering compounds for treating central nervous system disease involves surgical implantation of a device for delivering the compound over an extended period of time, such as in intrathecal delivery involving infusion into the spinal fluid through an implanted pump (available from Medtronic, Inc., Minneapolis, Minn.). Sustained release formulations of the invented medicaments particularly are contemplated.

Composition/Formulation

Pharmaceutical compositions and medicaments for use in accordance with the present invention may be formulated in a conventional manner using one or more physiologically acceptable carriers comprising excipients and auxiliaries. Proper formulation is dependent upon the route of administration chosen.

For injection, the agents of the invention may be formulated in aqueous solutions, preferably in physiologically compatible buffers such as Hanks's solution, Ringer's solution, or physiological saline buffer such as a phosphate or bicarbonate buffer. For transmucosal administration, penetrants appropriate to the barrier to be permeated are used in the formulation. Such penetrants are generally known in the art.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable gaseous propellant, e.g., carbon dioxide. In the case of a pressurized aerosol the dosage unit may be determined by providing a valve to deliver a metered amount. Capsules and cartridges of, e.g., gelatin, for use in an inhaler or insufflator, may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in aqueous vehicles, and may contain formulatory agents such as suspending, stabilizing and/or dispersing agents.

Pharmaceutical formulations for parenteral administration include aqueous solutions of the active compounds in water-soluble form. Aqueous suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder or lyophilized form for constitution with a suitable vehicle, such as sterile pyrogen-free water, before use.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Additionally, the compounds may be delivered using a sustained-release system, such as semipermeable matrices of solid hydrophobic polymers containing the therapeutic agent. Various sustained release materials have been established and are well known by those skilled in the art. Sustained-release capsules may, depending on their chemical nature, release the compounds for a few weeks up to over 100 days.

Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Effective Dosage.

Pharmaceutical compositions suitable for use in the present invention include compositions wherein the active ingredients are contained in an effective amount to achieve their intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays, and a dose can be formulated in animal models. Such information can be used to more accurately determine useful doses in humans.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the LD50, (the dose lethal to 50% of the test population) and the ED50 (the dose therapeutically effective in 50% of the population). The dose ratio between toxic and therapeutic effects is the therapeutic index and it can be expressed as the ratio between LD50 and ED50. Compounds which exhibit high therapeutic indices are preferred.

The data obtained from these cell culture assays and animal studies can be used in formulating a range of dosage for use in human. The dosage of such compounds lies preferably within a range of circulating concentrations that include the ED50, with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, in "The Pharmacological Basis of Therapeutics", Ch. 1).

Prevention, Diagnosis and Treatment of Psychiatric and other Diseases

As described above, an aspect of the present invention relates to the preparation of a medicament for the treatment of psychiatric disease, in particular schizophrenia and bipolar disorder, as well as CaM-KII associated disorders, including disorders associated with learning and memory, such as Alzheimer's Disease, dementia, and other conditions. The present compounds can also be used to inhibit CaM-KII activity in cancer cells, thereby inhibiting the proliferation of the cells. The present invention thus embodies medicaments acting on PAPAP and/or comprising PAPAP polypeptides and/or PAPAP polynucleotides.

In preferred embodiments, medicaments of the invention act on PAPAP, either by acting directly on PAPAP, a subunit associated with a PAPAP complex, a PAPAP-g34872 complex, a PAPAP-CaM-KII complex, or indirectly, by acting on the PAPAP pathway. For example, the medicaments may modulate, and more preferably decrease the level of PAPAP activity which occurs in a cell or particular tissue, or increase or decrease the activity of the PAPAP protein. In certain embodiments, the invention thus comprises use of a compound capable of increasing or decreasing PAPAP expression or PAPAP protein activity in the preparation or manufacture of a medicament. Preferably, said compound is used for the treatment of a psychiatric disease, preferably for the treatment of schizophrenia or bipolar disorder. Preferably, said compound acts directly by binding to PAPAP, g34872, CaM-KII, or a PAPAP receptor. Said g34872 may be any g34872 polypeptide, including the polypeptide of SEQ ID NO: 5 or a polypeptide described in copending patent application Ser. No. 09/539,333 titled "Schizophrenia associated genes, proteins and biallelic markers", filed 30 Mar. 2000. Said Cam-KII can be any calcium-calmodulin kinase II, preferably CaM-kIT alpha or CaM-KII beta.

Such medicaments may also increase or decrease the activity of a compound analogous to PAPAP, a compound comprising an amino acid sequence having at least 25% amino acid identity to the sequence of SEQ ID NO: 2, a compound comprising an amino acid sequence having at least 50% amino acid identity to the sequence of SEQ ID NO: 2, and a compound comprising an amino acid sequence having at least 80% amino acid identity to the sequence of SEQ ID NO: 2.

Medicaments which increase or decrease the activity of these compounds in an individual may be used to ameliorate or prevent symptoms in individuals suffering from or predisposed to a psychiatric disease, as discussed herein, as well as any of the other neurological, cognitive, or cancer-related disorders discussed herein, or any other disorders treatable by inhibiting CaM-KII activity.

Alternatively, PAPAP activity may be increased or decreased by the expression of the genes encoding PAPAP or a PAPAP-modulating compound using gene therapy. Examples of vectors and promoters suitable for use in gene therapy are described above. PAPAP activity may also be increased or decreased by preparing an antibody which binds to a PAPAP peptide, a PAPAP receptor or a protein related thereto, as well as fragments of these proteins. Such antibodies may modulate the interaction between PAPAP and a PAPAP receptor or a protein related thereto. Antibodies and methods of obtaining them are further described herein.

As described above, the present invention provides cellular assays for identifying compounds for the treatment of psychiatric and other diseases. The assays are based on detection of PAPAP expression, measurement of PAPAP protein activity, or based on the determination of other suitable disease endpoints of schizophrenia, bipolar disorder, a related psychiatric disorder, or any of the disorders discussed herein. Compounds for the treatment of psychiatric disease include derivative proteins or peptides which are capable of inhibiting the activity of a wild type PAPAP protein, which may be identified by determining their ability to bind a wild type PAPAP protein. Compounds also include antibodies, and small molecules and drugs which may be obtained using a variety of synthetic approaches familiar to those skilled in the art, including combinatorial chemistry based techniques. Methods of identifying compounds and methods of preparing formulations and administering medicaments are further described herein.

PAPAP in Methods of Diagnosis or Detecting Predisposition to CNS disorders

Individuals affected by or predisposed to schizophrenia, bipolar disorder or a related disorder, or to any CaM-KII related disorder including memory and learning disorders, may express abnormal levels of PAPAP. Individuals having increased or decreased PAPAP activity in their plasma, body fluids, or body tissues may be at risk of developing schizophrenia, bipolar disorder or any of the other CNS or other disorders described herein by a common disease mechanism. In one aspect of the present invention is a method for determining whether an individual is at risk of suffering from or is currently suffering from such a disorder (e.g. schizophrenia, bipolar disorder or other psychotic disorders, mood disorders, autism, substance dependence or alcoholism, mental retardation, or other psychiatric diseases including cognitive, learning, memory, anxiety, eating, impulse-control, and personality disorders, as defined with the Diagnosis and Statistical Manual of Mental Disorders fourth edition (DSM-IV) classification, or any other described herein or linked to CaM-KII activity), comprising determining whether the individual has an abnormal level of PAPAP activity, including activity of the PAPAP protein and/or PAPAP mRNA expression, or abnormal level of PAPAP protein in plasma, body fluids, or body tissues. The level of PAPAP or analogous compounds in plasma, body fluids, or body tissues may be determined using a variety approaches. In particular, the level of PAPAP protein may be determined using for example using Western Blots or protein electrophoresis. Detection of PAPAP may also be carried out using an antibody directed against a PAPAP polypeptide of the invention. Detection of the specific binding to the antibody indicates the presence of a PAPAP polypeptide in the sample (e.g., ELISA). This could reflect a pathological state associated with PAPAP.

In another aspect, one or more PAPAP biallelic markers, polymorphisms or variants can also be used to develop diagnostics tests capable of identifying individuals who express a detectable trait as the result of a specific genotype or individuals whose genotype places them at risk of developing a detectable trait at a subsequent time. The trait analyzed using the present diagnostics may be used to diagnose any detectable trait, including predisposition to schizophrenia or bipolar disorder or a related disorder such as those described in the examples above, age of onset of detectable symptoms, a beneficial response to or side effects related to treatment against one of said disorders. Such a diagnosis can be useful in the monitoring, prognosis and/or prophylactic or curative therapy of the disorder. These diagnostic techniques are based on the knowledge of the PAPAP nucleic acid sequence and may employ a variety of methodologies to determine whether a test subject has a genotype associated with an increased risk of developing a detectable trait or whether the individual suffers from a detectable trait as a result of a particular mutation, including methods which enable the analysis of individual chromosomes for haplotyping, such as family studies, single sperm DNA analysis or somatic hybrids. These diagnostic techniques can involve the detection of specific alleles present within the PAPAP sequence, including in PAPAP regulatory sequences or generally in the human chromosome 13q33 region. More particularly, the invention concerns the detection of a nucleic acid comprising at least one of the nucleotide sequences of SEQ ID NOs: 1 or 3, or a fragment thereof or a complementary sequence thereto.

These methods involve obtaining a nucleic acid sample from the individual and, determining, whether the nucleic acid sample contains at least one allele or at least one biallelic marker haplotype, indicative of a risk of developing the trait or indicative that the individual expresses the trait as a result of possessing a particular PAPAP-related polymorphism or mutation (trait-causing allele).

The diagnostics may be based on a single biallelic marker or a on group of biallelic markers. In each of these methods, a nucleic acid sample is obtained from the test subject and the biallelic marker pattern of one or more of a biallelic marker of the invention is determined. In one embodiment, a PCR amplification is conducted on the nucleic acid sample to amplify regions in which polymorphisms associated with a detectable phenotype have been identified. The amplification products are sequenced to determine whether the individual possesses one or more PAPAP-related polymorphisms associated with a detectable phenotype. Alternatively, the nucleic acid sample is subjected to microsequencing reactions to determine whether the individual possesses one or more PAPAP-related polymorphisms associated with a detectable phenotype resulting from a mutation or a polymorphism in the human PAPAP gene. In another embodiment, the nucleic acid sample is contacted with one or more allele specific oligonucleotide probes which, specifically hybridize to one or more PAPAP-related alleles associated with a detectable phenotype. In another embodiment, the nucleic acid sample is contacted with a second oligonucleotide capable of producing an amplification product when used with the allele specific oligonucleotide in an amplification reaction. The presence of an amplification product in the amplification reaction indicates that the individual possesses one or more PAPAP-related alleles associated with a detectable phenotype. In a preferred embodiment, the detectable trait is schizophrenia or bipolar disorder. Diagnostic kits comprise any of the polynucleotides of the present invention. These diagnostic methods are extremely valuable as they can, in certain circumstances, be used to initiate preventive treatments or to allow an individual carrying a significant haplotype to foresee warning signs such as minor symptoms.

Diagnostics, which analyze and predict response to a drug or side effects to a drug, may be used to determine whether an individual should be treated with a particular drug. For example, if the diagnostic indicates a likelihood that an individual will respond positively to treatment with a particular drug, the drug may be administered to the individual. Conversely, if the diagnostic indicates that an individual is likely to respond negatively to treatment with a particular drug, an alternative course of treatment may be prescribed. A negative response may be defined as either the absence of an efficacious response or the presence of toxic side effects.

Clinical drug trials represent another application for the diagnostic methods of the present invention. One or more markers indicative of response to an agent acting against schizophrenia or to side effects to an agent acting against schizophrenia may be identified using the methods described above. Thereafter, potential participants in clinical trials of such an agent may be screened to identify those individuals most likely to respond favorably to the drug and exclude those likely to experience side effects. In that way, the effectiveness of drug treatment may be measured in individuals who respond positively to the drug, without lowering the measurement as a result of the inclusion of individuals who are unlikely to respond positively in the study and without risking undesirable safety problems.

Prevention and Management of Disease

Because of the risk of suicide for example, the detection of susceptibility to schizophrenia, bipolar disorder as well as other psychiatric disease in individuals is very important. Consequently, the invention concerns a method for the treatment of a disorder, including particularly CNS disorders such as schizophrenia, bipolar disorder, a cognitive, learning, or memory disorder, or any PAPAP related disorder related thereto comprising the following steps:

selecting an individual whose DNA comprises alleles of a PAPAP-related polymorphism, biallelic marker or of a group of biallelic markers, or who presents abnormal PAPAP mRNA expression or PAPAP protein activity associated with a CNS disorder;

following up said individual for the appearance (and optionally the development) of the symptoms related to said disorder; and administering a treatment acting against the disorder or against symptoms thereof to said individual at an appropriate stage of the disease.

Another embodiment of the present invention comprises a method for the treatment of any of the herein-described disorders comprising the following steps:

selecting an individual whose DNA comprises alleles of a PAPAP-related polymorphism, biallelic marker or of a group of biallelic markers, or who presents abnormal PAPAP mRNA expression or PAPAP protein activity associated with a PAPAP-related disorder;

administering a preventive treatment of said disorder to said individual.

In a further embodiment, the present invention concerns a method for the treatment of any of the herein-described disorders comprising the following steps:

selecting an individual whose DNA comprises alleles of a PAPAP-related polymorphism, biallelic marker or of a group of biallelic markers, or who presents abnormal PAPAP mRNA expression or PAPAP protein activity associated with a disorder;

administering a preventive treatment of said disorder to said individual;

following up said individual for the appearance and the development of symptoms of said disorder; and optionally administering a treatment acting against said disorder or against symptoms thereof to said individual at the appropriate stage of the disease.

For use in the determination of the course of treatment of an individual suffering from disease, the present invention also concerns a method for the treatment of any of the herein-described disorders comprising the following steps:

selecting an individual suffering from schizophrenia or bipolar disorder whose DNA comprises alleles of a PAPAP-related polymorphism, biallelic marker or of a group of biallelic markers, or who presents abnormal PAPAP mRNA expression or PAPAP protein activity associated with the gravity of a PAPAP-related disorder or of the symptoms thereof, and administering a treatment acting against said disorder or symptoms thereof to said individual.

The invention also concerns a method for the treatment of a PAPAP-related disorder in a selected population of individuals. The method comprises:

selecting an individual suffering from a PAPAP-related disorder and whose DNA comprises alleles of a PAPAP-related polymorphism, biallelic marker or of a group of biallelic markers, or who presents abnormal PAPAP mRNA expression or PAPAP protein activity associated with a positive response to treatment with an effective amount of a medicament acting against said disorder or symptoms thereof, and/or whose DNA does not comprise alleles of a PAPAP-related polymorphism, biallelic marker or of a group of biallelic markers, or who presents abnormal PAPAP mRNA expression or PAPAP protein activity associated with a negative response to treatment with said medicament; and administering at suitable intervals an effective amount of said medicament to said selected individual.

In the context of the present invention, a "positive response" to a medicament can be defined as comprising a reduction of the symptoms related to the disease. In the context of the present invention, a "negative response" to a medicament can be defined as comprising either a lack of positive response to the medicament which does not lead to a symptom reduction or which leads to a side-effect observed following administration of the medicament.

Preferred CNS disorders in the methods of the invention are schizophrenia and bipolar disorder. However, the present invention also comprises any of the prevention, diagnostic, prognosis and treatment methods described herein for any of the herein-described disorders. By way of example, related disorders may comprise learning disorders, cognitive disorders, memory disorders, psychotic disorders, mood disorders, autism, substance dependence and alcoholism, mental retardation, and other psychiatric diseases including anxiety, eating, impulse-control, and personality disorders, as defined with the Diagnosis and Statistical Manual of Mental Disorders fourth edition (DSM-IV) classification.

The invention also relates to a method of determining whether a subject is likely to respond positively to treatment with a medicament. The method comprises identifying a first population of individuals who respond positively to said medicament and a second population of individuals who respond negatively to said medicament. One or more biallelic markers is identified in the first population which is associated with a positive response to said medicament or one or more biallelic markers is identified in the second population which is associated with a negative response to said medicament. The biallelic markers may be identified using the techniques described herein.

A DNA sample is then obtained from the subject to be tested. The DNA sample is analyzed to determine whether it comprises alleles of one or more biallelic markers associated with a positive response to treatment with the medicament and/or alleles of one or more biallelic markers associated with a negative response to treatment with the medicament.

In some embodiments, the medicament may be administered to the subject in a clinical trial if the DNA sample contains alleles of one or more biallelic markers associated with a positive response to treatment with the medicament and/or if the DNA sample lacks alleles of one or more biallelic markers associated with a negative response to treatment with the medicament. In preferred embodiments, the medicament is a drug acting against schizophrenia or bipolar disorder.

Using the method of the present invention, the evaluation of drug efficacy may be conducted in a population of individuals likely to respond favorably to the medicament.

Another aspect of the invention is a method of using a medicament comprising obtaining a DNA sample from a subject, determining whether the DNA sample contains alleles of one or more biallelic markers associated with a positive response to the medicament and/or whether the DNA sample contains alleles of one or more biallelic markers associated with a negative response to the medicament, and administering the medicament to the subject if the DNA sample contains alleles of one or more biallelic markers associated with a positive response to the medicament and/or if the DNA sample lacks alleles of one or more biallelic markers associated with a negative response to the medicament.

The invention also concerns a method for the clinical testing of a medicament, preferably a medicament acting against schizophrenia or bipolar disorder or symptoms thereof, but also possible with any medicament acting against any of the herein-described disorders or symptoms. The method comprises the following steps:
  administering a medicament, preferably a medicament susceptible of acting against schizophrenia or or bipolar disorder or symptoms thereof to a heterogeneous population of individuals,
  identifying a first population of individuals who respond positively to said medicament and a second population of individuals who respond negatively to said medicament,
  identifying biallelic markers in said first population which are associated with a positive response to said medicament,
  selecting individuals whose DNA comprises biallelic markers associated with a positive response to said medicament, and
  administering said medicament to said individuals.

Such methods are deemed to be extremely useful to increase the benefit/risk ratio resulting from the administration of medicaments which may cause undesirable side effects and/or be inefficacious to a portion of the patient population to which it is normally administered.

Once an individual has been diagnosed as suffering from any of the herein-described disorders, preferably schizophrenia or bipolar disorder, selection tests are carried out to determine whether the DNA of this individual comprises alleles of a biallelic marker or of a group of biallelic markers associated with a positive response to treatment or with a negative response to treatment which may include either side effects or unresponsiveness.

The selection of the patient to be treated using the method of the present invention can be carried out through the detection methods described above. The individuals which are to be selected are preferably those whose DNA does not comprise alleles of a biallelic marker or of a group of biallelic markers associated with a negative response to treatment. The knowledge of an individual's genetic predisposition to unresponsiveness or side effects to particular medicaments allows the clinician to direct treatment toward appropriate drugs against schizophrenia or bipolar disorder or symptoms thereof.

Once the patient's genetic predispositions have been determined, the clinician can select appropriate treatment for which negative response, particularly side effects, has not been reported or has been reported only marginally for the patient.

Throughout this application, various publications, patents and published patent applications are cited. The disclosures of these publications, patents and published patent specification referenced in this application are hereby incorporated by reference into the present disclosure to more fully describe the sate of the art to which this invention pertains.

EXAMPLES

Example 1

In Situ Receptor Binding Assay (Cell staining)

AP Fusion Construct

An in-frame fusion of a cDNA sequence encoding the PAP peptide amino acid sequence (SEQ ID NO: 5) with the C-terminus of secreted alkaline phosphatase (AP) was created in a pAPtag expression vector. The nucleotide and amino acid sequence of the (fusion) protein sequence inserted in the vector are shown in SEQ ID NOs: 4 and 6 respectively.

This vector contains a secretion signal sequence located upstream of the insert which directs the fusion protein to be secreted into the media. Media containing the fusion protein can be collected, assayed for AP activity, and used in the in situ receptor/ligand assay.

The AP fusion protein was then transfected into 293T cells and stable transfectants were selected by conference to Zeocin resistance. Media from the cells containing the stable transfectants was collected every 3 days and assayed for AP activity. This AP-fusion containing media is subsequently used for the in situ receptor binding assay, as follows below.

A human brain cDNA library was constructed using the Stratagene cDNA synthesis kit. The cDNA was cloned into the mammalian expression vector pMT21-neo (GenHunter). Plasmid DNA was obtained from pools of ~1000 colonies using the QiaPrep Spin Miniprep kit (Qiagen). These pools of DNA were then transiently transfected into COS-1 cells as follows. Two micrograms of DNA from each pool of human brain cDNAs was diluted into 200 ul of serum-free medium (DMEM medium from Gibco-BRL with no additives). The DNA was complexed to the PLUS reagent by adding 12 ul of (mixed prior to use) PLUS reagent to the DNA in serum-free medium. 200 ul of the DNA-PLUS-Lipofectamine reagent complexes was added to wells containing Cos-1 cells plated at $0.25 \times 10^5$ cells per well in 6 well dishes (35 mm) the day prior to transfection (in complete medium containing no antibiotics). Previous to the addition of the DNA/lipofectamine/PLUS complex, the complete medium was removed from the cells and replaced with 800 ul serum-free medium. Cells were incubated at 37 degrees C. at 5% $CO_2$ for 3 hours; then the medium in each well was replaced with 2 ml of complete medium.

Receptor Cloning of Receptor/Ligand

The secreted AP fusion protein was used as a probe to clone PAPAP by an expression cloning strategy.

Two days after transfection, cell staining was begun. Culture medium was removed from cells in the 6 well dishes. The attached cells were washed once with 2 ml of HBHA wash buffer ((50 ml of 10×HBSS (1×), 0.25 grams of BSA (0.5 mg/ml), 10 ml of 1M HEPES pH 7.5 (20 mM), brought to 500 ml with dH$_2$O)), and incubated for 90 minutes at room temperature with 2 ml of PAP-AP fusion protein containing medium, or AP containing medium (as a negative control). The medium was removed and the sample was washed at least 5 times with 2 ml of HBHA buffer over a 10 minute period. The HBHA buffer was completely removed, and cells were fixed for 30 seconds with 2 ml of fixing reagent (60% acetone, 3% formaldehye, 20 mM HEPES pH 7.5). The fixing reagent was immediately removed, and the sample was washed twice using 2 ml of HS buffer per well ((15 ml 5M NaCl (150 mM), 10 ml 1 M HEPES pH 7.5 (20 mM), brought to 500 ml with dH$_2$O)). The sample was incubated in HS buffer at 65 degrees C. for 100 minutes to heat inactivate the endogenous AP. The HS buffer was removed, and the cell surface bound AP activity was stained with 1 ml of AP assay reagent (50 ml 1 M Tris-HCl pH 9.5 (100 mM), 10 ml 5 M NaCl (100 mM), 2.5 ml 1M MgCl$_2$ (5 mM) brought to 500 ml, to which was added NBT to a final concentration of 0.33 mg/ml and BCIP to a final concentration of 0.17 mg/ml.).

As a positive clone was detected, the assay was repeated using smaller pools of cDNAs until a single clone (the PAPAP nucleic acid) was identified.

Example 2

Preparation of Antibody Compositions to the PAPAP Protein

Substantially pure protein or polypeptide is isolated from transfected or transformed cells containing an expression vector encoding the PAPAP protein or a portion thereof. The concentration of protein in the final preparation is adjusted, for example, by concentration on an Amicon filter device, to the level of a few micrograms/ml. Monoclonal or polyclonal antibody to the protein can then be prepared as follows:

A. Monoclonal Antibody Production by Hybridoma Fusion

Monoclonal antibody to epitopes in the PAPAP protein or a portion thereof can be prepared from murine hybridomas according to the classical method of Kohler, G. and Milstein, C., (1975) or derivative methods thereof. Also see Harlow, E., and D. Lane. 1988.

Briefly, a mouse is repetitively inoculated with a few micrograms of the PAPAP protein or a portion thereof over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, (1980), and derivative methods thereof. Selected positive clones can be expanded and their monoclonal antibody product harvested for use. Detailed procedures for monoclonal antibody production are described in Davis, L. et al. Basic Methods in Molecular Biology Elsevier, N.Y. Section 21-2.

B. Polyclonal Antibody Production by Immunization

Polyclonal antiserum containing antibodies to heterogeneous epitopes in the PAPAP protein or a portion thereof can be prepared by immunizing suitable non-human animal with the PAPAP protein or a portion thereof, which can be unmodified or modified to enhance immunogenicity. A suitable non-human animal is preferably a non-human mammal is selected, usually a mouse, rat, rabbit, goat, or horse. Alternatively, a crude preparation which has been enriched for PAPAP concentration can be used to generate antibodies. Such proteins, fragments or preparations are introduced into the non-human mammal in the presence of an appropriate adjuvant (e.g. aluminum hydroxide, RIBI, etc.) which is known in the art. In addition the protein, fragment or preparation can be pretreated with an agent which will increase antigenicity, such agents are known in the art and include, for example, methylated bovine serum albumin (mBSA), bovine serum albumin (BSA), Hepatitis B surface antigen, and keyhole limpet hemocyanin (KLH). Serum from the immunized animal is collected, treated and tested according to known procedures. If the serum contains polyclonal antibodies to undesired epitopes, the polyclonal antibodies can be purified by immunoaffinity chromatography.

Effective polyclonal antibody production is affected by many factors related both to the antigen and the host species. Also, host animals vary in response to site of inoculations and dose, with both inadequate or excessive doses of antigen resulting in low titer antisera. Small doses (ng level) of antigen administered at multiple intradermal sites appears to be most reliable. Techniques for producing and processing polyclonal antisera are known in the art, see for example, Mayer and Walker (1987). An effective immunization protocol for rabbits can be found in Vaitukaitis, J. et al. (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., (1973). Plateau concentration of antibody is usually in the range of 0.1 to 0.2 mg/ml of serum (about 12 □M). Affinity of the antisera for the antigen is determined by preparing competitive binding curves, as described, for example, by Fisher, D., (1980).

Antibody preparations prepared according to either the monoclonal or the polyclonal protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

While the preferred embodiment of the invention has been illustrated and described, it will be appreciated that various changes can be made therein by the one skilled in the art without departing from the spirit and scope of the invention.

REFERENCES

Abbondanzo S J et al., 1993, Methods in Enzymology, Academic Press, New York, pp 803-823
Ajioka R. S. et al., Am. J. Hum. Genet., 60:1439-1447, 1997
Altschul et al., 1990, J. Mol. Biol. 215(3):403-410
Altschul et al., 1993, Nature Genetics 3:266-272
Altschul et al., 1997, Nuc. Acids Res. 25:3389-3402
Ames, R. S. et al. J. Immunol. Methods 184:177-186 (1995)
Anton M. et al., 1995, J. Virol., 69: 4600-4606
Araki K et al. (1995) Proc. Natl. Acad. Sci. USA. 92(1):160-4.
Ashkenazi, A. et al. PNAS 88:10535-10539 (1991)
Aszódi et al., Proteins:Structure, Function, and Genetics, Supplement 1:38-42 (1997)

Ausubel et al. (1989) Current Protocols in Molecular Biology, Green Publishing Associates and Wiley Interscience, N.Y.
Bartunek, P. et al. Cytokine 8(1):14-20 (1996)
Baubonis W. (1993) Nucleic Acids Res. 21(9):2025-9.
Beaucage et al., Tetrahedron Lett 1981, 22: 1859-1862
Better, M. et al. Science 240:1041-1043 (1988)
Bradley A., 1987, Production and analysis of chimaeric mice. In: E. J. Robertson (Ed.), Teratocarcinomas and embryonic stem cells: A practical approach. IRL Press, Oxford, pp. 113.
Bram R J et al., 1993, Mol. Cell. Biol., 13: 4760-4769
Brinkman U. et al. J. Immunol. Methods 182:41-50 (1995)
Brown E L, Belagaje R, Ryan M J, Khorana H G, Methods Enzymol 1979; 68:109-151
Brutlag et al. Comp. App. Biosci. 6:237-245, 1990
Burton, D. R. et al. Advances in Immunology 57:191-280 (1994)
Bush et al., 1997, J. Chromatogr., 777: 311-328.
Carlson, N. G. et al. J. Biol. Chem. 272(17):11295-11301 (1997)
Chai H. et al. (1993) Biotechnol. Appl. Biochem. 18:259-273.
Chee et al. (1996) Science. 274:610-614.
Chen and Kwok Nucleic Acids Research 25:347-353 1997
Chen et al. (1987) Mol. Cell. Biol. 7:2745-2752.
Chen et al. Proc. Natl. Acad. Sci. USA 94/20 10756-10761, 1997
Chen, Z. et al. Cancer Res. 58(16): 3668-3678 (1998)
Cho R J et al., 1998, Proc. Natl. Acad. Sci. USA, 95(7): 3752-3757.
Chou J. Y., 1989, Mol. Endocrinol., 3: 1511-1514.
Clark A. G. (1990) Mol. Biol. Evol. 7:111-122.
Coles R, Caswell R, Rubinsztein D C, Hum Mol Genet. 1998; 7:791-800
Compton J. (1991) Nature. 350(6313):91-92.
Davis L. G., M. D. Dibner, and J. F. Battey, Basic Methods in Molecular Biology, ed., Elsevier Press, NY, 1986
Deng, B. et al. Blood 92(6): 1981-1988 (1998)
Dent D S & Latchman D S (1993) The DNA mobility shift assay. In: Transcription Factors: A Practical Approach (Latchman D S, ed.) pp 1-26. Oxford: IRL Press
Eckner R. et al. (1991) EMBO J. 10:3513-3522.
Edwards et Leatherbarrow, Analytical Biochemistry, 246, 1-6 (1997)
Engvall, E., Meth. Enzymol. 70:419 (1980)
Feldman and Steg, 1996, Medecine/Sciences, synthese, 12:47-55
Felici F., 1991, J. Mol. Biol., Vol. 222:301-310
Fell, H. P. et al. J. Immunol. 146:2446-2452 (1991)
Fields and Song, 1989, Nature, 340: 245-246
Fisher, D., Chap. 42 in: Manual of Clinical Immunology, 2d Ed. (Rose and Friedman, Eds.) Amer. Soc. For Microbiol., Washington, D.C. (1980)
Flotte et al. (1992) Am. J. Respir. Cell Mol. Biol. 7:349-356.
Fodor et al. (1991) Science 251:767-777.
Fraley et al. (1979) Proc. Natl. Acad. Sci. USA. 76:3348-3352.
Fried M, Crothers D M, Nucleic Acids Res 1981; 9:6505-6525
Fromont-Racine M. et al., 1997, Nature Genetics, 16(3): 277-282.
Fuller S. A. et al. (1996) Immunology in Current Protocols in Molecular Biology, Ausubel et al. Eds, John Wiley & Sons, Inc., USA.
Furth P. A. et al. (1994) Proc. Natl. Acad. Sci. USA. 91:9302-9306.
Garner M M, Revzin A, Nucleic Acids Res 1981; 9:3047-3060
Geysen H. Mario et al. 1984. Proc. Natl. Acad. Sci. U.S.A. 81:3998-4002
Ghosh and Bacchawat, 1991, Targeting of liposomes to hepatocytes, IN: Liver Diseases, Targeted diagnosis and therapy using specific receptors and ligands. Wu et al. Eds., Marcel Dekeker, New York, pp. 87-104.
Gillies, S. D. et al. J. Immunol. Methods 125:191-202 (1989)
Gillies, S. O. et al. PNAS 89:1428-1432 (1992)
Gonnet et al., 1992, Science 256:1443-1445
Gopal (1985) Mol. Cell. Biol., 5:1188-1190.
Gossen M. et al. (1992) Proc. Natl. Acad. Sci. USA. 89:5547-5551.
Gossen M. et al. (1995) Science. 268:1766-1769.
Graham et al. (1973) Virology 52:456-457.
Green et al., Ann. Rev. Biochem. 55:569-597 (1986)
Greenspan and Bona, FASEB J. 7(5):437-444 (1989)
Griffin et al. Science 245:967-971 (1989)
Grompe, M. (1993) Nature Genetics. 5:111-117.
Grompe, M. et al. (1989) Proc. Natl. Acad. Sci. U.S.A. 86:5855-5892.
Gu H. et al. (1993) Cell 73:1155-1164.
Gu H. et al. (1994) Science 265:103-106.
Guatelli J C et al. Proc. Natl. Acad. Sci. USA. 35:273-286.
Hacia J G, Brody L C, Chee M S, Fodor S P, Collins F S, Nat Genet. 1996; 14(4): 441-447
Hall L. A. and Smirnov I. P. (1997) Genome Research, 7:378-388.
Hames B. D. and Higgins S. J. (1985) Nucleic Acid Hybridization: A Practical Approach. Hames and Higgins Ed., IRL Press, Oxford.
Harju L, Weber T, Alexandrova L, Lukin M, Ranki M, Jalanko A, Clin Chem 1993; 39(1 IPt 1):2282-2287
Harland et al. (1985) J. Cell. Biol. 101:1094-1095.
Harlow, E., and D. Lane. 1988. Antibodies A Laboratory Manual. Cold Spring Harbor Laboratory. pp. 53-242
Harper J W et al., 1993, Cell, 75: 805-816
Hammerling, et al., in: MONOCLONAL ANTIBODIES AND T-CELL HYBRIDOMAS 563-681 (Elsevier, N.Y., 1981)
Harrop, J. A. et al. J. Immunol. 161(4): 1786-1794 (1998)
Hawley M. E. et al. (1994) Am. J. Phys. Anthropol. 18:104.
Henikoff and Henikoff, 1993, Proteins 17:49-61
Higgins et al., 1996, Methods Enzymol. 266:383-402
Hillier L. and Green P. Methods Appl., 1991, 1: 124-8.
Hoess et al. (1986) Nucleic Acids Res. 14:2287-2300.
Huang L. et al. (1996) Cancer Res 56(5):1137-1141.
Huston et al. Methods in Enzymology 203:46-88 (1991)
Huygen et al. (1996) Nature Medicine. 2(8):893-898.
Izant J G, Weintraub H, Cell 1984 April; 36(4):1007-15
Julan et al. (1992) J. Gen. Virol. 73:3251-3255.
Kanegae Y. et al., Nucl. Acids Res. 23:3816-3821 (1995).
Karlin and Altschul, 1990, Proc. Natl. Acad. Sci. USA 87:2267-2268
Kettleborough, C. A. et al. Eur. J. Immunol. 24:952-958 (1994)
Khoury J. et al., Fundamentals of Genetic Epidemiology, Oxford University Press, NY, 1993
Kim U-J. et al. (1996) Genomics 34:213-218.
Klein et al. (1987) Nature. 327:70-73.
Kohler, G. and Milstein, C., Nature 256:495 (1975)
Koller et al. (1992) Annu. Rev. Immunol. 10:705-730.
Kozal M J, Shah N, Shen N, Yang R, Fucini R, Merigan T C, Richman D D, Morris D, Hubbell E, Chee M, Gingeras T R, Nat Med 1996; 2(7):753-759
Landegren U. et al. (1998) Genome Research, 8:769-776.

Lange K. (1997) Mathematical and Statistical Methods for Genetic Analysis. Springer, New York.
Lenhard T. et al. (1996) Gene. 169:187-190.
Liautard, J. et al. Cytokinde 9(4):233-241 (1997)
Linton M. F. et al. (1993) J. Clin. Invest. 92:3029-3037.
Liu Z. et al. (1994) Proc. Natl. Acad. Sci. USA. 91: 4528-4262.
Livak et al., Nature Genetics, 9:341-342, 1995
Livak K J, Hainer J W, Hum Mutat 1994; 3(4):379-385
Lockhart et al. Nature Biotechnology 14: 1675-1680, 1996
Lucas A. H., 1994, In: Development and Clinical Uses of Haempophilus b Conjugate;
Mansour S. L. et al. (1988) Nature. 336:348-352.
Marshall R. L. et al. (1994) PCR Methods and Applications. 4:80-84.
McCormick et al. (1994) Genet. Anal. Tech. Appl. 1:158-164.
McLaughlin B. A. et al. (1996) Am. J. Hum. Genet. 59:561-569.
Morton N. E., Am. J. Hum. Genet., 7:277-318, 1955
Morrison, Science 229:1202 (1985)
Muller, Y. A. et al. Structure 6(9):1153-1167 (1998)
Mullinax, R. L. et al. BioTechniques 12(6):864-869 (1992)
Muzyczka et al. (1992) Curr. Topics in Micro. and Immunol. 158:97-129.
Nada S. et al. (1993) Cell 73:1125-1135.
Nagy A. et al., 1993, Proc. Natl. Acad. Sci. USA, 90: 8424-8428.
Naramura, M. et al. Immunol. Lett. 39:91-99 (1994)
Narang S A, Hsiung H M, Brousseau R, Methods Enzymol 1979; 68:90-98
Neda et al. (1991) J. Biol. Chem. 266:14143-14146.
Newton et al. (1989) Nucleic Acids Res. 17:2503-2516.
Nickerson D. A. et al. (1990) Proc. Natl. Acad. Sci. U.S.A. 87:8923-8927.
Nicolau C. et al., 1987, Methods Enzymol., 149:157-76.
Nicolau et al. (1982) Biochim. Biophys. Acta. 721:185-190.
Nissinoff, J. Immunol. 147(8): 2429-2438 (1991).
Nyren P, Pettersson B, Uhlen M, Anal Biochem 1993; 208 (1):171-175
Oi et al., BioTechniques 4:214 (1986)
O'Reilly et al. (1992) Baculovirus Expression Vectors: A Laboratory Manual. W. H. Freeman and Co., New York.
Ohno et al. (1994) Science. 265:781-784.
Oldenburg K. R. et al., 1992, Proc. Natl. Acad. Sci., 89:5393-5397.
Orita et al. (1989) Proc. Natl. Acad. Sci. U.S.A. 86: 2776-2770.
Ouchterlony, O. et al., Chap. 19 in: Handbook of Experimental Immunology D. Wier (ed) Blackwell (1973)
Padlan E. A., Molecular Immunology 28 (4/5): 489-498 (1991)
Parmley and Smith, Gene, 1988, 73:305-318
Pastinen et al., Genome Research 1997; 7:606-614
Pearson and Lipman, 1988, Proc. Natl. Acad. Sci. USA 85(8): 2444-2448
Pease S. ans William R. S., 1990, Exp. Cell. Res., 190: 209-211.
Persic, L. et al. Gene 187 9-18 (1997)
Perlin et al. (1994) Am. J. Hurn. Genet. 55:777-787.
Peterson et al., 1993, Proc. Natl. Acad. Sci. USA, 90: 7593-7597.
Pietu et al. Genome Research 6:492-503, 1996
Pitard, V. et al. J. Immunol. Methods 205(2):177-190 (1997)
Potter et al. (1984) Proc. Natl. Acad. Sci. U.S.A. 81(22): 7161-7165.
Prat, M. et al. J. Cell. Sci. 111 (Pt2): 237-247 (1998)
Ramunsen et al., 1997, Electrophoresis, 18: 588-598.
Reid L. H. et al. (1990) Proc. Natl. Acad. Sci. U.S.A. 87:4299-4303.
Robertson E., 1987, Embryo-derived stem cell lines. In: E. J. Robertson Ed. Teratocarcinomas and embrionic stem cells: a practical approach. IRL Press, Oxford, pp. 71.
Roguska M. A. et al. PNAS 91:969-973), (1994)
Rossi et al., Pharmacol. Ther. 50:245-254, (1991)
Roth J. A. et al. (1996) Nature Medicine. 2(9):985-991.
Roux et al. (1989) Proc. Natl. Acad. Sci. U.S.A. 86:9079-9083.
Ruano et al. (1990) Proc. Natl. Acad. Sci. U.S.A. 87:6296-6300.
Sambrook, J., Fritsch, E. F., and T. Maniatis. (1989) Molecular Cloning: A Laboratory Manual. 2ed. Cold Spring Harbor Laboratory, Cold Spring Harbor, N.Y.
Samson M, et al. (1996) Nature, 382(6593):722-725.
Samulski et al. (1989) J. Virol. 63:3822-3828.
Sanchez-Pescador R. (1988) J. Clin. Microbiol. 26(10):1934-1938.
Sarkar, G. and Sommer S. S. (1991) Biotechniques.
Sauer B. et al. (1988) Proc. Natl. Acad. Sci. U.S.A. 85:5166-5170.
Sawai, H. et al. AJRI 34:26-34 (1995)
Schaid D. J. et al., Genet. Epidemiol., 13:423-450, 1996
Schedl A. et al., 1993a, Nature, 362: 258-261.
Schedl et al., 1993b, Nucleic Acids Res., 21: 4783-4787.
Schena et al. Science 270:467-470, 1995
Schena et al., 1996, Proc Natl Acad Sci USA, 93(20): 10614-10619.
Schneider et al. (1997) Arlequin: A Software For Population Genetics Data Analysis. University of Geneva.
Schwartz and Dayhoff, eds., 1978, Matrices for Detecting Distance Relationships: Atlas of Protein Sequence and Structure, Washington: National Biomedical Research Foundation Sczakiel G. et al. (1995) Trends Microbiol. 3(6):213-217.
Shay J. W. et al., 1991, Biochem. Biophys. Acta, 1072: 1-7.
Sheffield, V. C. et al. (1991) Proc. Natl. Acad. Sci. U.S.A. 49:699-706.
Shizuya et al. (1992) Proc. Natl. Acad. Sci. U.S.A. 89:8794-8797.
Shoemaker D D, et al., Nat Genet. 1996; 14(4):450-456
Shu, L. et al. PNAS 90:7995-7999 (1993)
Skerra, A. et al. Science 240:1038-1040. (1988)
Smith (1957) Ann. Hum. Genet. 21:254-276.
Smith et al. (1983) Mol. Cell. Biol. 3:2156-2165.
Sosnowski R G, et al., Proc Natl Acad Sci USA 1997; 94: 1119-1123
Sowdhamini et al., Protein Engineering 10:207, 215 (1997)
Spielmann S, and Ewens W. J., Am. J. Hum. Genet., 62:450-458, 1998
Spielmann S. et al., Am. J. Hum. Genet., 52:506-516, 1993
Sternberg N. L. (1992) Trends Genet. 8:1-16.
Sternberg N. L. (1994) Mamm. Genome. 5:397-404.
Stryer, L., Biochemistry, 4th edition, 1995
Studnicka G. M. et al. Protein Engineering 7(6):805-814 (1994)
Syvanen A C, Clin Chim Acta 1994; 226(2):225-236
Szabo A. et al. Curr Opin Struct Biol 5, 699-705 (1995)
Tacson et al. (1996) Nature Medicine. 2(8):888-892.
Taryman, R. E. et al. Neuron 14(4):755-762 (1995)
Te Riele et al. (1990) Nature. 348:649-651.
Terwilliger J. D. and Ott J., Handbook of Human Genetic Linkage, John Hoplins University Press, London, 1994
Thomas K. R. et al. (1986) Cell. 44:419-428.
Thomas K. R. et al. (1987) Cell. 51:503-512.
Thompson et al., 1994, Nucleic Acids Res. 22(2):4673-4680

Tur-Kaspa et al. (1986) Mol. Cell. Biol. 6:716-718.
Tyagi et al. (1998) Nature Biotechnology. 16:49-53.
Urdea M. S. (1988) Nucleic Acids Research. 11:4937-4957.
Urdea M. S. et al. (1991) Nucleic Acids Symp. Ser. 24:197-200.
Vaitukaitis, J. et al. J. Clin. Endocrinol. Metab. 33:988-991 (1971)
Valadon P., et al., 1996, J. Mol. Biol., 261:11-22.
Van der Lugt et al. (1991) Gene. 105:263-267.
Vil, H. et al. PNAS 89:11337-11341 (1992)
Vlasak R. et al. (1983) Eur. J. Biochem. 135:123-126.
Wabiko et al. (1986) DNA.5(4):305-314.
Walker et al. (1996) Clin. Chem. 42:9-13.
Wang et al., 1997, Chromatographia, 44: 205-208.
Westerink M. A. J., 1995, Proc. Natl. Acad. Sci., 92:4021-4025
White, M. B. et al. (1992) Genomics. 12:301-306.
White, M. B. et al. (1997) Genomics. 12:301-306.
Wong et al. (1980) Gene. 10:87-94.
Wood S. A. et al., 1993, Proc. Natl. Acad. Sci. USA, 90: 4582-4585.
Wu and Wu (1987) J. Biol. Chem. 262:4429-4432.
Wu and Wu (1988) Biochemistry. 27:887-892.
Wu et al. (1989) Proc. Natl. Acad. Sci. U.S.A. 86:2757.
Yagi T. et al. (1990) Proc. Natl. Acad. Sci. U.S.A. 87:9918-9922.
Yoon, D. Y. et al. J. Immunol. 160(7): 3170-3179 (1998)
Zhao et al., Am. J. Hum. Genet., 63:225-240, 1998
Zheng, X. X. et al. J. Immunol. 154:5590-5600 (1995)
Zhu, Z. et al. Cancer Res. 58(15): 3209-3214 (1998)
Zou Y. R. et al. (1994) Curr. Biol. 4:1099-1103.

What is claimed:

1. An isolated polypeptide comprising:
   a) SEQ ID NO:2;
   b) a polypeptide that is at least 95% identical to the amino acid sequence of SEQ ID NO:2 and binds to the polypeptide g34872 or binds to a calcium/calmodulin-dependent kinase II (CaM-KII); or
   c) a fusion protein comprising a heterologous polypeptide fused to:
      i) SEQ ID NO:2; or
      ii) a polypeptide that is at least 95% identical to the amino acid sequence of SEQ ID NO:2 and binds to the polypeptide g34872 or binds to a calcium/calmodulin-dependent kinase II (CaM-KII).

2. The isolated polypeptide of claim 1, further comprising a label.

3. The isolated polypeptide of claim 1, wherein said polypeptide is bound to a solid support.

4. The isolated polypeptide of claim 1, wherein said polypeptide comprises SEQ ID NO:2.

5. The isolated polypeptide of claim 1, wherein said polypeptide is at least 95% identical to the amino acid sequence of SEQ ID NO:2 and binds to the polypeptide g34872 or binds to a calcium/calmodulin-dependent kinase II (CaM-KII).

6. The isolated polypeptide of claim 1, wherein said polypeptide is a fusion protein comprising a heterologous polypeptide fused to SEQ ID NO:2.

7. The isolated polypeptide of claim 1, wherein said polypeptide is a fusion protein comprising a heterologous polypeptide fused to a polypeptide that is at least 95% identical to the amino acid sequence of SEQ ID NO:2 and binds to the polypeptide g34872 or binds to a calcium/calmodulin-dependent kinase II (CaM-KIT).

8. The isolated polypeptide of claim 2, wherein said polypeptide comprises SEQ ID NO:2.

9. The isolated polypeptide of claim 2, wherein said polypeptide is at least 95% identical to the amino acid sequence of SEQ ID NO:2 and binds to the polypeptide g34872 or binds to a calcium/calmodulin-dependent kinase II (CaM-KII).

10. The isolated polypeptide of claim 3, wherein said polypeptide comprises SEQ ID NO:2.

11. The isolated polypeptide of claim 3, wherein said polypeptide is at least 95% identical to the amino acid sequence of SEQ ID NO:2 and binds to the polypeptide g34872 or binds to a calcium/calmodulin-dependent kinase II (CaM-KII).

12. A composition comprising a carrier and a polypeptide comprising:
   a) SEQ ID NO:2;
   b) a polypeptide that is at least 95% identical to the amino acid sequence of SEQ ID NO:2 and binds to the polypeptide g34872 or binds to a calcium/calmodulin-dependent kinase II (CaM-KII); or
   c) a fusion protein comprising a heterologous polypeptide fused to:
      i) SEQ ID NO:2; or
      ii) a polypeptide that is at least 95% identical to the amino acid sequence of SEQ ID NO:2 and binds to the polypeptide g34872 or binds to a calcium/calmodulin-dependent kinase II (CaM-KII).

13. The composition of claim 12, wherein said polypeptide comprises SEQ ID NO:2.

14. The composition of claim 12, wherein said polypeptide is at least 95% identical to the amino acid sequence of SEQ ID NO:2 and binds to the polypeptide g34872 or binds to a calcium/calmodulin-dependent kinase II (CaM-KII).

15. The composition of claim 12, wherein said polypeptide is a fusion protein comprising a heterologous polypeptide fused to SEQ ID NO:2.

16. The composition of claim 12, wherein said polypeptide is a fusion protein comprising a heterologous polypeptide fused to a polypeptide that is at least 95% identical to the amino acid sequence of SEQ ID NO:2 and binds to the polypeptide g34872 or binds to a calcium/calmodulin-dependent kinase II (CaM-KII).

* * * * *